United States Patent [19]

Gubin et al.

[11] Patent Number: 4,994,474
[45] Date of Patent: Feb. 19, 1991

[54] ALKYL- OR ARLY-AMINOALKOXY-BENZENE-SULFONYL INDOLES

[75] Inventors: Jean Gubin; Pierre Chatelain, both of Brussels; Henri Inion, Wemmel, all of Belgium

[73] Assignee: Sanofi, Paris, France

[21] Appl. No.: 306,499

[22] Filed: Feb. 6, 1989

Related U.S. Application Data

[63] Continuation-in-part of Ser. No. 82,554, Aug. 7, 1987, Pat. No. 4,957,925, which is a continuation-in-part of Ser. No. 6,233, Jan. 23, 1987, abandoned.

[30] Foreign Application Priority Data

Feb. 14, 1986 [FR] France ................. 8602045

[51] Int. Cl.$^5$ ................. A61K 31/40; A61K 31/45
[52] U.S. Cl. ................. 514/339; 514/418; 548/484; 548/486; 548/186; 548/190; 548/245; 548/247; 548/326; 548/342; 546/273; 546/121; 546/153; 546/301; 544/224; 544/236; 544/310; 549/462
[58] Field of Search ............ 548/484, 486; 514/418, 514/339; 546/273

[56] References Cited

U.S. PATENT DOCUMENTS

| | | | |
|---|---|---|---|
| 3,502,667 | 3/1970 | Nakanishi | 548/484 |
| 3,825,558 | 7/1974 | Seemann | 548/486 |
| 3,859,305 | 1/1975 | Posselt | 548/484 |
| 3,860,609 | 1/1975 | Lundt | 548/484 |
| 4,103,012 | 7/1978 | Gubin et al. | 544/362 |
| 4,117,128 | 9/1978 | Brenner | 514/212 |
| 4,128,552 | 12/1978 | Wise et al. | |
| 4,220,645 | 9/1980 | Chibret | |
| 4,654,360 | 3/1987 | Greenhouse | 548/484 |
| 4,675,405 | 6/1987 | Musser et al. | 548/486 |
| 4,826,847 | 5/1989 | Michel | 514/418 |
| 4,851,406 | 7/1989 | Mertens et al. | 514/339 |
| 4,873,259 | 10/1989 | Summers et al. | 514/418 |

FOREIGN PATENT DOCUMENTS

| | | |
|---|---|---|
| 0121197 | 10/1984 | European Pat. Off. |
| 0302792 | 2/1989 | European Pat. Off. |
| 0302793 | 2/1989 | European Pat. Off. |
| 2341578 | 9/1977 | France |
| 2400515 | 3/1979 | France |
| 2594438 | 8/1987 | France |

OTHER PUBLICATIONS

Gubin et al., Eur. J. Med. Chem., 12, 1977, 345-50.
Truce et al., J. Org. Chem., 35, 12, 1970, 4217.
van Leusen et al, Tetrahedron Letters, vol. 23, 2373-4 (1972).
Oldenziel et al, Tetrahedron Letters, vol. 27, 2777-8 (1972).
Frehel et al, Heterocycles, vol. 22, No. 5, 1984, pp. 1235-1247.

(List continued on next page.)

Primary Examiner—Donald G. Daus
Attorney, Agent, or Firm—Bacon & Thomas

[57] ABSTRACT

The present invention relates to aminoalkoxyphenyl derivatives of formula:

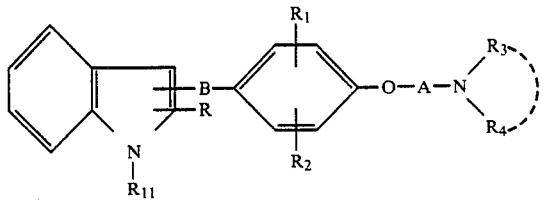

and its N-oxide and pharmaceutically acceptable salts, in which:

B represents a —S—, —SO— or —SO$_2$— group,

R$_1$ and R$_2$, which are identical or different, each denote hydrogen, a methyl or ethyl radial or a halogen atom, A denotes a straight-or branched-alkylene radical having from 2 to 5 carbon atoms or a 2-hydroxypropylene radial in which the hydroxy is optionally substituted by a lower alkyl radical, R$_3$ denotes an alkkyl radical or a radical of formula:

—Alk—Ar in which Alk denotes a single bond or a linear-or branched-alkylene radical having from 1 to 5 carbon atoms and Ar denotes a pyridyl, phenyl, 2,3-methylenedioxyphenyl or 3,4-methylenedioxyphenyl radical or a phenyl group substituted with one or more substituents, which may be identical or different, selected from halogen atoms, lower alkyl group or lower alkoxy groups, R$_{11}$ denotes hydrogen or a lower alkyl, phenyl, diphenylmethyl, benzyl or halogenobenzyl radical, R$_4$ denotes hydrogen or an alkyl radical, or R$_3$ and R$_4$ when taken together denote an alkylene or alkenylene radical having from 3 to 6 carbon atoms and optionally substituted with a phenyl radical or optionally interrupted by —O—, —N= or —N—R$_{11}$, R represent hydrogen, an alkyl radical, a cycloalkyl radical, a benzyl radical or a phenyl radical optionally substituted with one or more substituents, which may be identical or different, selected from halogen atoms and from lower alkyl, lower alkoxy or nitro groups, are described. The compounds of the invention possess exceptional pharmacological properties, especially calcium transport inhibitory properties, as well as bradycardic, hypotensive and antiadrenergic properties.

14 Claims, No Drawings

OTHER PUBLICATIONS

Renzi et al, Gazzetta Chimica Italiana, 1968, vol. 98, pp. 656–666.
Takahashi et al, J. Heterocyclic Chem., 23, 1363 (1986).
Alford et al., D. Chem. Soc, 1953, 609–12.
Bragg, J. Chem. Soc. 1962, 2627–9.
Ruggli et al, Helv. Chem. Acta. 18, 253 (1935).
Charlier, Bruxelles–Medical, 9, Sep. 1969.
Inion et al., Eur. J. Med. Chem., 12, 5, 1977, 483.
Gubin et al., L'Ingenieur Chimiste, Mar. 1977.
Goldenberg et al., Chimie Therapeutique, Sep.–Oct. 1972, vol. 7, No. 5, 369–77.
Augstein et al, Cardiovascular Effects, vol. 8, 356–67 (1965).

ALKYL- OR ARLY-AMINOALKOXY-BENZENE-SULFONYL INDOLES

CROSS REFERENCE TO RELATED APPLICATIONS

This application is a continuation-in-part application of co-pending application Ser. No. 82,554, filed Aug. 7, 1987, now U.S. Pat. No. 4,957,925 which is a continuation-in-part of application Ser. No. 006,233 now abandoned.

The present invention relates to new carbocyclic or heterocyclic derivatives and to a process for preparing them.

More particularly, the invention relates to the novel aminoalkoxyphenyl derivatives represented by the general formula:

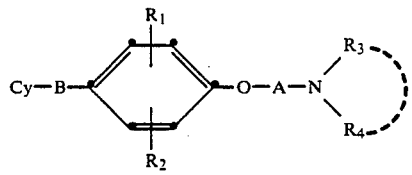

I in which:

B represents a —S—, —SO— or —SO$_2$— group, $R_1$ and $R_2$, which are identical or different, each denote hydrogen, a methyl or ethyl radical or a halogen such as chlorine, bromine or iodine, A denotes a straight- or branched-alkylene radical having from 2 to 5 carbon atoms or a 2-hydroxypropylene radical in which the hydroxy is optionally substituted by a lower alkyl radical, $R_3$ denotes an alkyl radical or a radical of formula —Alk—Ar in which Alk denotes a single bond or a linear- or branched-alkylene radical having from 1 to 5 carbon atoms and Ar denotes a pyridyl, phenyl, 2,3-methylenedioxyphenyl or 3,4-methylenedioxyphenyl radical or a phenyl group substituted with one or more substituents, which may be identical or different, selected from halogen atoms, lower alkyl groups or lower alkoxy groups, $R_4$ denotes hydrogen or an alkyl radical, or $R_3$ and $R_4$ when taken together, denote an alkylene or alkenylene radical having from 3 to 6 carbon atoms and optionally substituted with a phenyl radical or optionally interrupted by —O—, —N= or $-\overset{|}{N}-R_{11}$, $R_{11}$ denoting hydrogen or a lower alkyl, phenyl, diphenylmethyl, benzyl or halogenobenzyl radical, Cy represents a group of formula:

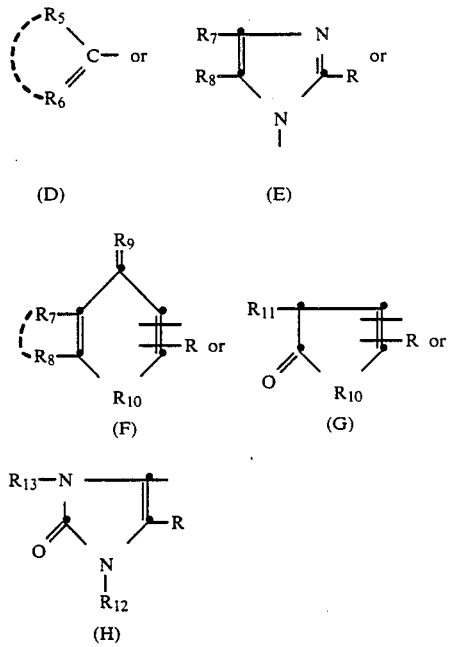

R represents hydrogen, an alkyl radical, a cycloalkyl radical, a benzyl radical or a phenyl radical optionally substituted with one or more substituents, which may be identical or different, selected from halogen atoms, for example fluorine, chlorine, bromine atoms and from lower alkyl, lower alkoxy or nitro groups, $R_5$ and $R_6$ are taken together with the carbon atom to which they are attached to form:

an optionally aromatic mono- or di-cyclic carbocyclic group having from 5 to 10 carbon atoms and optionally substituted by a R group in the α-position with respect to the methyne group, an optionally aromatic 5-membered heterocyclic group, the heteroatoms or heterogroups being selected from the groups O, S, N, $-\overset{|}{N}-R$; O and N; O and $-\overset{|}{N}-R_{11}$; S and N;

S and $-\overset{|}{N}-R_{11}$; N and N; N and $-\overset{|}{N}-R_{11}$, the heterocyclic group being optionally substituted by a R group in the α-position with respect to the methyne group and optionally substituted by one or two groups selected from lower alkyl and phenyl groups, an optionally aromatic 6- to 10-membered mono- or di-cyclic heterocyclic group, the heteroatoms or heterogroups being selected from the groups O, S, N, $-\overset{|}{N}-R$; O and N; O and $-\overset{|}{N}-R_{11}$; S and N;

S and $-\overset{|}{N}-R_{11}$; N and N; N and $-\overset{|}{N}-R_{11}$, the heterocyclic group being optionally substituted by a R group in the α-position with respect to the methyne group, R₇ and R₈, which are the same or different, each represent hydrogen, a lower alkyl radical or a phenyl radical or when they are taken together with the carbon atoms to which they are attached represent an optionally aromatic 6-membered carbocyclic ring, R₉ represents oxygen or sulphur R₁₀ represents oxygen, sulphur or a group

R₁₂ and R₁₃, which are identical or different, each represent hydrogen, a lower alkyl radical or a benzoyl radical with the proviso that when Cy represents a benzo[b]furyl or benzo[b]thienyl group and B represents a —SO₂— group, R₃ represents a radical —Alk—Ar and with the proviso that Cy does not represent 1-indolizinyl radical.

In the present context, both in the description and in the claims, the following meaning attaches to the terms stated above:

"alkyl" denotes straight- or branched-saturated aliphatic hydrocarbon residues having up to 8 carbon atoms, such as methyl, ethyl, n-propyl, isopropyl, n-butyl, isobutyl, tert-butyl, n-pentyl, neopentyl, n-hexyl, n-heptyl or n-octyl, "lower alkyl" denotes saturated aliphatic hydrocarbon residues having up to 4 carbon atoms, such as methyl, ethyl, n-propyl, isopropyl, n-butyl, isobutyl, tert-butyl or 1-methylpropyl, "lower alkoxy" denotes a hydroxy group substituted with a lower alkyl group as defined above, "cycloalkyl" denotes an alicyclic ring having from 3 to 6 carbon atoms.

Thus, taking into account the meanings given above:

R can denote, in particular, a methyl, ethyl, n-propyl, isopropyl, n-butyl, isobutyl, tert-butyl, 1-methylpropyl, n-pentyl, neopentyl, phenyl, monofluoro-, monochloro- or monobromophenyl, difluoro-, dichloro- or dibromophenyl, monomethyl- or dimethylphenyl, or monomethoxy- or dimethoxyphenyl radical, a methylphenyl radical substituted with a halogen atom or a cyclopropyl radical, A can denote, in particular, a 1,2-ethylene, 1,3-propylene, 2-methyl-1,3-propylene, 1,4-tetramethylene or 1,5-pentamethylene chain, R₃ can denote, in particular, a methyl, ethyl, n-propyl, isopropyl, n-butyl, isobutyl, tert-butyl, 1-methylpropyl, n-pentyl, n-hexyl, n-heptyl, n-octyl, phenyl, benzyl or phenethyl radical, a methoxyphenyl or a dimethoxyphenethyl, for example 3,4-dimethoxyphenethyl radical, a dimethylphenethyl, dimethoxyphenyl, dimethoxybenzyl or pyridylethyl radical or a phenethyl radical substituted in the aromatic portion, with methyl and methoxy radicals, R₄ can denote, in particular, a methyl, ethyl, n-propyl, isopropyl, n-butyl, isobutyl, tert-butyl, n-pentyl, neopentyl, n-hexyl, n-heptyl or n-octyl radical, R₃ and R₄, taken together, can denote, in particular, a 1,4-tetramethylene, 1,5-pentamethylene, 3-oxo-1,5-pentamethylene, 3-aza-1,5-pentamethylene, 3-methyl-aza-1,5-pentamethylene, 3-aza-1,5-pentamethylene, 3-phenylaza-1,5-pentamethylene or —CH=CH—N=CH— radical, so that R₃ and R₄, taken with the nitrogen atom to which they are attached, can denote, in particular, pyrrolidinyl, piperidyl, morpholinyl, piperazinyl, 4-methylpiperazinyl, 4-phenylpiperazinyl or 1H-imidazolyl radical.

Cy can denote, in particular, a phenyl, cyclohexenyl, indenyl, naphthyl, dihydronaphthyl, pyridyl, dihydropyridyl, furyl, dihydrofuryl, thienyl, dihydrothienyl, pyrrolyl, dihydropyrrolyl, pyrazolyl, imidazolyl, pyrimidyl, pyrazinyl, pyridazinyl, oxazolyl, isoxazolyl, thiazolyl, benzofuryl, benzothienyl, indolyl, benzimidazolyl, benzoxazolyl, quinolinyl, benzisoxazolyl, cinnolinyl, quinoxalinyl, quinazolinyl, indolizin-3-yl, thienopyridyl, tetrahydrothienopyridyl, pyrrolopyridyl, pyrazolopyridyl, pyrrolopyridazinyl, imidazopyridyl, dihydrofuranonyl, imidazolinonyl, chromonyl radical.

A particular valuable class of compounds of formula (1) are those in which Cy represents an indolizin-3-yl group.

Another class of compounds are those in which R₁ and R₂ each are hydrogen.

Another class of compounds of formula (1) are those in which R₃ represents a group of formula —Alk—Ar.

A particular class of useful compounds of formula (1) are those in which R₃ represents hydrogen and R₄ represents tert-butyl or R₃ and R₄ each represent n-propyl or n-butyl.

Particularly useful compounds of formula (1) are those in which the chain

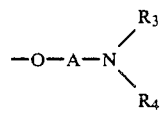

represents a [N-methyl-N-(3,4-dimethoxy-β-phenethyl)amino]propyloxy group.

Other valuable compounds of formula (1) are those in which R represents an isopropyl or cyclopropyl group.

The invention also relates to the pharmaceutically acceptable salts of the compounds of formula (1) formed with an organic or inorganic acid.

As examples of organic salts of this type, there may be mentioned the oxalate, maleate, fumarate, methanesulphonate, benzoate, ascorbate, pamoate, succinate, hexamate, bismethylenesalicylate, ethanedisulphonate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulphonate and theophyllineacetate, as well as the salts formed with an amino acid such as the lysine or histidine salt.

As examples of inorganic salts of this type, the hydrochloride, hydrobromide, sulphate, sulphamate, phosphate and nitrate may be mentioned.

Another object of the invention relates to the N-oxide derivatives of the compounds of formula (1).

The compounds of formula (1) can exist, in some cases, in the form of optical isomers, in particular as a result of the asymmetric carbon present when A represents a 2-hydroxypropylene chain.

The invention relates, at the same time, to all the isomers of the compounds of formula (1), the isomers being considered in the dextrorotatory or laevorotatory form, or in the form of a mixture, for example in the form of a racemic mixture.

It has been found that the aminoalkoxyphenyl derivatives of the invention possess exceptional pharmacological properties, especially calcium transport inhibitory properties, as well as bradycardic, hypotensive and antiadrenergic properties.

From this viewpoint, the preferred compounds of the invention are those in which B represents a —$SO_2$— group.

These properties are capable of making the compounds in question very useful on the treatment of certain pathological syndromes of the cardiovascular system, especially in the treatment of angina pectoris, hypertension, arrhythmia and cerebral circulatory insufficiency.

In the antitumour field, the compounds of the invention may be useful as potentiators of anticancer drugs.

Consequently, the invention also relates to pharmaceutical or veterinary compositions containing, as active principle, at least one aminoalkoxyphenyl derivative of formula (1) or a pharmaceutically acceptable salt of this derivative, or an N-oxide derivative thereof, in combination with a pharmaceutical vehicle or a suitable excipient.

Another object of the invention relates to a method for treating pathological syndromes of the cardiovascular system especially angina pectoris, hypertension, arrhythmia and cerebral vascular insufficiency in a host in need of such treatment comprising the administration to this host of an effective dose of an aminoalkoxyphenyl derivative of the invention.

Depending on the administration route selected, the daily dosage for a human being weighing 60 kg will be between 2 and 500 mg of active principle.

The compounds of formula I can be obtained:

I. When B represents a —S— or —$SO_2$— group and A represents an alkylene radical, by condensing, in the presence of an acid acceptor and in a polar solvent such as dimethylsulphoxide or an alcohol, for example butanol, or a ketone such as methyl ethyl ketone, or a nonpolar solvent such as an aromatic hydrocarbon, for example benzene, toluene or xylene, a 4-alkoxyphenyl derivative of general formula:

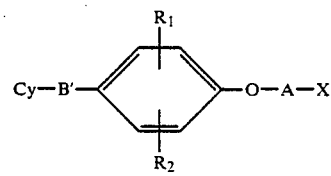

(2)

in which B' represents a —S— or —$SO_2$— group, Cy, $R_1$ and $R_2$ have the same meaning as above, A represents an alkylene radical as defined in the formula I and X represents a halogen atom, preferably bromine, or an alkylsulphonyloxy group having from 1 to 4 carbon atoms such as for example, methanesulphonyloxy, or an arylsulphonyloxy group having from 6 to 10 carbon atoms, such as benzenesulphonyloxy or p-toluenesulphonyloxy, with an amine of general formula:

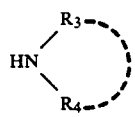

(3)

in which $R_3$ and $R_4$ have the same meaning as above to form the desired aminoalkoxyphenyl derivative of formula (1) in the form of a free base.

In general, the condensation in question is performed at a temperature between room-temperature and the refluxing-temperature of the medium, the acid acceptor being, for example, an alkali metal carbonate or hydroxide or an excess of amine of formula (3).

The compounds of formula (2) in question can be obtained:

(a) when X is a halogen, by condensation of a 4-hydroxyphenyl derivative of general formula:

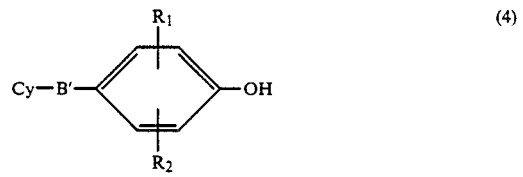

(4)

in which Cy, B', $R_1$ and $R_2$ have the same meaning as above, with a dihaloalkane of general formula

Hal—A—Hal    (5)

in which A denotes an alkylene radical as defined in the formula (1) and Hal denotes a halogen atom, preferably bromine, this reaction being performed under reflux in a solvent such as methyl ethyl ketone or N,N-dimethylformamide and in the presence of a basic agent such as an alkali metal carbonate, for example potassium carbonate, an alkali metal hydride such as sodium hydride, an alkali metal hydroxide, for example sodium or potassium hydroxide, or an alkali metal alcoholate, for example sodium methylate or ethylate, (b) when X denotes an alkylsulphonyloxy or arylsulphonyloxy group, by condensation of a halide of general formula:

Hal—W in which Hal has the same meaning as above and W denotes an alkylsulphonyl radical having from 1 to 4 carbon atoms, for example methanesulphonyl, or an arylsulphonyl radical having from 6 to 10 carbon atoms, for example benzenesulphonyl or p-toluenesulphonyl, in a solvent which is an acid acceptor, for example pyridine, with a 4-hydroxyalkoxy derivative of general formula:

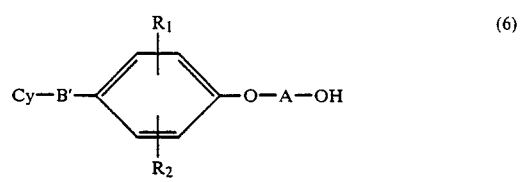

(6)

in which Cy, B', $R_1$ and $R_2$ have the same meaning as above and A denotes an alkylene radical as defined in formula (1).

As regards the compounds of formula (6), these can be prepared by condensing, in a suitable solvent such as N,N-dimethylformamide and in the presence of a basic agent such as an alkali metal carbonate, for example potassium carbonate, an alkali metal hydroxide such as sodium or potassium hydroxide, an alkali metal hydride such as sodium hydride or an alkali metal alcoholate, for example sodium methylate or ethylate, a 4-hydroxyphenyl derivative of formula (4) above with a halogenated alcohol of general formula:

   (7)

in which A denotes an alkylene radical as defined in the and Hal has the same meaning as above.

Compounds of formula (4) are known products, for instance those compounds in which Cy represents a benzofuryl or benzothienyl group and B' represents a —$SO_2$— group. These compounds are disclosed in U.S. Pat. No. 4,117,128.

The other compounds of can be prepared in a general procedure, by adapting to the desired compound the method described in the aforesaid U.S. patent or the methods described hereunder.

In most cases, those compounds of can be obtained by fixing a 4-O-protected benzenesulphonyl or phenylthio chain to the required carbocycle or heterocycle using a Friedel-Crafts reaction and deprotecting the oxygen in the 4-position of the benzenesulphonyl or phenylthio group by means of classical procedures to regenerate the OH group.

Hereunder are examples of methods commonly used for preparing derivatives of formula (4):

(a) Compounds of formula (4) in which Cy represents a group (D)

(1) The compounds of formula (4) in which Cy represents a 2-R-indolizin-3-yl group can be prepared by reacting an indolizine derivative of general formula:

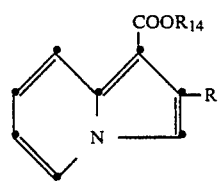   (8)

in which R has the same meaning as above and $R_{14}$ represents a lower alkyl radical preferably ethyl, with a halide of general formula:

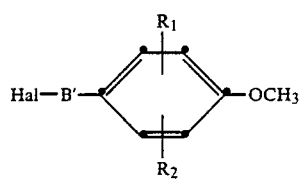   (9)

in which B', $R_1$, $R_2$ and Hal have the same meaning as above and in the presence of a Friedel-Crafts catalyst such as aluminium chloride to provide a compound of general formula:

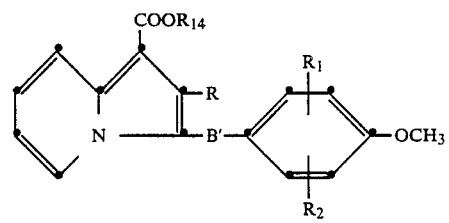   (10)

in which B', R, $R_1$, $R_2$ and $R_{14}$ have the same meaning as above.

The compound of formula (10) is subsequently demethylated using an ethanethiol/aluminium chloride mixture to give a 4-methoxyphenyl derivative of general formula:

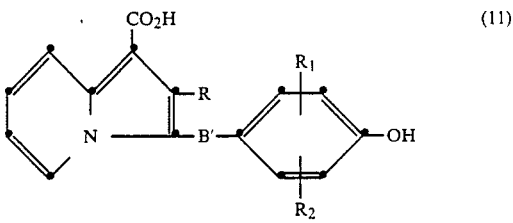   (11)

in which B', R, $R_1$ and $R_2$ have the same meaning as above which, when heated to about 200° C. provides the required compound of formula (4).

The compounds of formula (8) are either known compounds having been published in J. Chem. Soc. 1962 pp. 2627–2629 or compounds which can be prepared in accordance with the method described therein.

(2) The compounds of formula (4) in which Cy represents a 2-R-imidazo[1,2-a]pyrid-3-yl group can be prepared from a 2-R-imidazo[1,2-a]pyridine with a halide of formula (9) and in the presence of a Friedel-Crafts catalyst such as aluminium chloride to provide a compound of general formula:

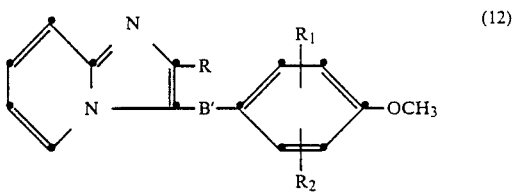   (12)

in which B', R, $R_1$ and $R_2$ have the same meaning as above.

The compound of formula (12) is subsequently demethylated using an appropriate agent for instance hydrobromic acid or an ethanethiol/aluminium chloride mixture to give the required compound of formula (4).

2-Aryl-imidazo[1,2-a]pyridines are known from J. Med. Chem. 8, p. 305 (1965). The other 2-R-imidazo[1,2-a]pyridines can be obtained in accordance with the method described in the aforesaid reference or using classical procedures.

Alternatively, the compounds of formula (12) can be obtained from a 2-R-3-halo-imidazo[1,2-a]pyridine and the alkali metal salt of a 4-methoxy derivative of formula (15).

(3) The compounds of formula (4) in which Cy represents a pyridyl or 3-R-4-pyridyl group can be obtained by demethylating with an appropriate agent such as aqueous hydrobromic acid, a 4-methoxyphenyl derivative of general formula:

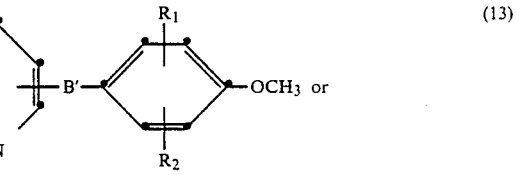   (13)

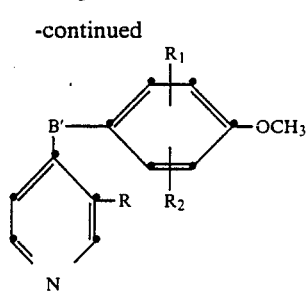 (13')

in which B', R₁ and R₂ have the same meaning as above and R has the same meaning as above with the exception of hydrogen, to provide the required compounds of formula (4).

The compounds of formulae (13) and (13') in which B' represents a —SO₂— group can be prepared by oxidizing a sulfide derivative of general formula:

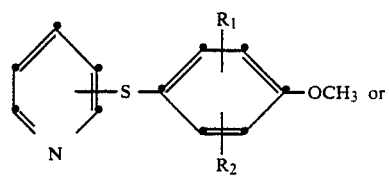 (14)

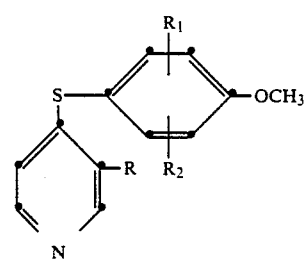 (14')

in which R₁ and R₂ have the same meaning as above and R has the same meaning as in formula (13) or (13').

Compounds of formula (14) are known having been described in U.S. Pat. No. 4,128,552. The other compounds of formula (14) can be obtained in accordance with the method described in the aforesaid U.S. patent while those compounds of formula (14') can be prepared from a 3-R-pyridine, in which R is other than hydrogen, by oxidation with hydrogen peroxide in acetic acid to provide the corresponding 3-R-pyridine-N-oxide which when reacted with a nitric acid/sulphuric acid mixture gives rise to the corresponding 3-R-4-nitro-pyridine-N-oxide.

This nitro derivative is then reacted first with acetyl bromide, then with iron powder in acetic acid to give the corresponding 3-R-4-bromo-pyridine which, when treated with a thiophenol derivative of general formula:

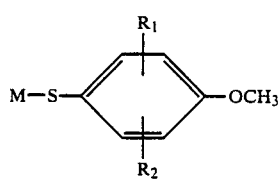 (15)

in which R₁ and R₂ have the same meaning as above and M represents an alkali metal atom such as sodium, provides the required compound of formula (14').

(4) The compounds of formula (4) in which Cy represents a 2-R-quinolin-3-yl group can be prepared by reacting an α-haloketone of general formula:

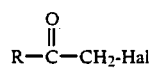 (16)

in which R and Hal have the same meaning as above, with a metal derivative of general formula:

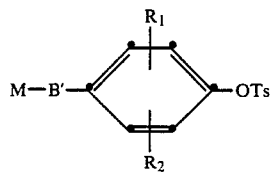 (17)

in which M, B', R₁ and R₂ have the same meaning as above and Ts represents a p-toluenesulphonyl group, to provide a ketone of general formula:

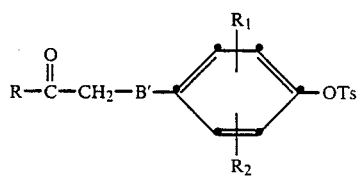 (18)

in which B', R, R₁ R₂ and Ts have the same meaning as above.

This ketone of formula (18) when treated with 2-amino-benzaldehyde [Helv. Chem. Act. vol. XVIII, p. 1235 (1935)] gives the 4-methoxyphenyl derivative of general formula:

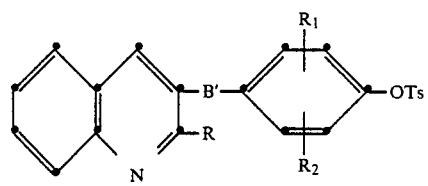 (19)

in which B', R, R₁, R₂ and Ts have the same meaning as above, which is subsequently hydrolysed in basic medium for instance in aqueous alkali metal hydroxide, to provide the required compound of formula (4).

(5) The compounds of formula (4) in which Cy represents a 3-R-cinnolin-4-yl or 4-R-cinnolin-3-yl group can be obtained by reacting a 3-R-4-halogenocinnoline (J. Chem. Soc. 1953, p. 609) with a thiophenol derivative of general formula:

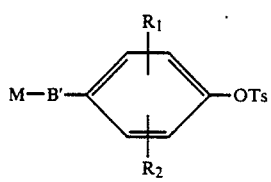 (20)

in which M, R₁, R₂ and Ts have the same meaning as above and B' represents a —S— group to provide the 4-tosyloxyphenyl derivative of general formula:

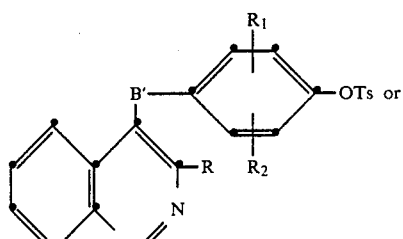
(21)

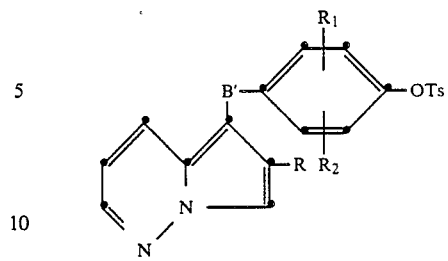
(23)

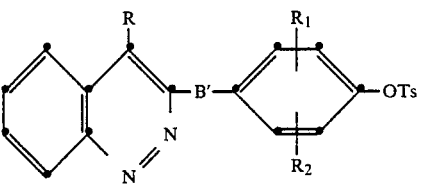
(27')

in which R, R₁, R₂ and Ts have the same meaning as above and B' represents a —S— group.

The 4-tosyloxyphenyl derivative of formula (21) or (21') is subsequently hydrolysed in basic medium for instance in aqueous alkali metal hydroxide to give the required compound of formula (4) in which B' represents a —S— group. Compounds of formula (20) in which —OTs is replaced by —OCH₃ can also be used. In such case the corresponding compound of formula (21) or (21') is demethylated using for instance hydrobromic acid.

The sulphide derivative of formula (21) or (21') when oxidized with a suitable agent such as hydrogen peroxide in acetic acid or potassium permanganate, provides the compound of (21) or (21') in which B' represents a —SO₂— group, which compound after hydrogenation on a catalyst such as palladium charcoal or platinum charcoal gives the required compounds of formula (4) in which B' represents a —SO₂— group.

Alternatively the compounds of formula (4) in question in which B' represents a —SO₂— group can be obtained from a 3-R-4-halogenocinnoline or a 4-R-3-halogeno-cinnoline by reacting with a benzenesulphonyl derivative of general formula (20) in which B' represents a —SO₂— group to obtain a compound of formula (21) or (21') in which B' represents a —SO₂— group which is detosylated as described above to provide the required compound of formula (4).

(6) The compounds of formula (4) in which Cy represents a 6-R-pyrrolo[1,2-b]pyridazin-5-yl group can be prepared by reacting a 3-halogenomethylpyridazine with a metal derivative of formula (17) to provide a pyridazine derivative of general formula:

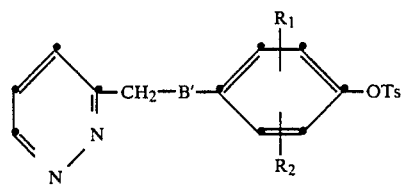
(22)

in which B', R₁, R₂ and Ts have the same meaning as above, which is subsequently reacted with an α-haloketone of formula (16) in the presence of a non-nucleophilic base such as for example 1,8-diazabicyclo[5,4,-0]undec-7-ene to give the pyrrolo[1,2-b]pyridazine derivative of general formula:

in which B', R, R₁, R₂ and Ts have the same meaning as above.

The tosyl derivative of formula (23) is then hydrolysed in a basic medium for instance aqueous alkali metal hydroxide, to provide the required compound of formula (4).

3-Chloromethyl-pyridazine is a known compound having been published in Khim. Geterot. Sikl. Soedin. 3, pp. 412–414 (1970).

7) The compounds of formula (4) in which Cy represents a 2-R-pyrazolo [1,5-a]pyrid-3-yl group can be prepared, in accordance with the method described in European patent application No. 121, 197, by treating a 2-R-pyrazolo[1,5-a]pyridine with a halide of formula (9) in the presence of a Friedel-Crafts catalyst such as for example aluminium chloride, to provide the 4-methoxyphenyl derivative of general formula:

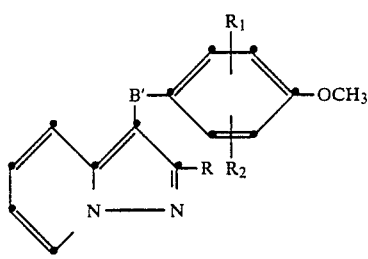
(24)

in which B', R, R₁ and R₂ have the same meaning as above.

The pyrazolopyridine derivative of formula (24) is then demethylated for instance by using pyridine hydrochloride at 200°–220° C. to provide the required compound of formula (4).

8) The compounds of formula (4) in which Cy represents a phenyl group can be prepared by reacting benzene with a halide of formula (9) in the presence of a Friedel-Crafts catalyst such as aluminium chloride, to provide the required compound of formula (4).

9) The compounds of formula (4) in which Cy represents a 2-R-phenyl group or a 1-R-2-naphthyl group can be prepared by treating a halide of general formula:

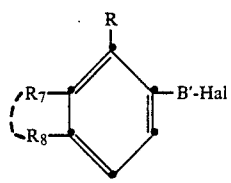
(25)

in which B', R and Hal have the same meaning as above and R₇ and R₈ each represent hydrogen or are taken together with the carbon atom to which they are attached to form a phenyl group, with a methoxyphenyl derivative of general formula:

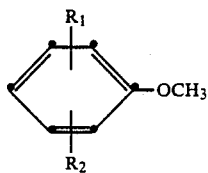  (26)

in which $R_1$ and $R_2$ have the same meaning as above, in the presence of a Friedel-Crafts catalyst such as aluminium chloride, to obtain the compounds of general formula:

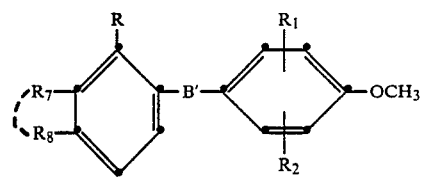  (27)

in which B', R, $R_1$ and $R_2$ have the same meaning as above and $R_7$ and $R_8$ have the same meaning as in formula (25).

The compounds of formula (27) are then demethylated using for instance aqueous iodhydric acid to provide the required compound of formula (4).

Compounds of formula (25) are known products having been described in C.A. 81, 63285g, or can be obtained in accordance with known procedures.

Alternatively the compounds of formula (27) in which $R_7$ and $R_8$ are each hydrogen and B' represents a —$SO_2$— group can be prepared by treating the alkali metal derivative of a 2-R-benzenesulphonate, with a phenyl derivative of formula (26) in the presence of methanesulphonic acid/phosphorous pentoxide, in accordance with the method described in Communications, April 1984, p. 323.

In accordance with another process, the compounds of formula (4) in which Cy represents a 2-naphthyl group and B' represents a —$SO_2$— group can be obtained by reacting a 2-halogenosulphonyl naphthalene with a $R_1R_2$-phenol derivative. This sulphonate derivative is then rearranged in the presence of aluminium chloride to obtain a complex which is treated by an acid such a hydrochloric acid to provide the required compound of formula (4).

10) The compounds of formula (4) in which Cy represents an optionally mono- or di-substituted 2-R-4,5-dihydro-furan-3-yl group can be prepared by heating a ketone derivative of formula (18) with a 1,2-dihalogenoethane of general formula:

Hal-CH—CH-Hal  (28)
　　|　　　|
　　$R_{15}$　$R_{16}$ in which $R_{15}$ and $R_{16}$ which are the same or different, each represent hydrogen, a lower alkyl radical or a phenyl radical, in the presence of a basic agent such as an alkali metal carbonate, to obtain a cyclopropane derivative of general formula:

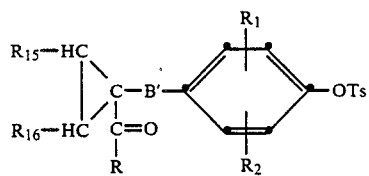  (29)

in which B', R, $R_1$, $R_2$, $R_{15}$, $R_{16}$ and Ts have the same meaning as above.

The cyclopropane derivative of formula (29) is subsequently heated between 100° and 130° C. in the presence of a phase transfer catalyst such as for instance triphenylphosphine or tricaprylylmethyl ammonium chloride to provide a 4-tosyloxyphenyl derivative of general formula:

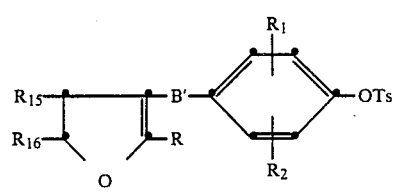  (30)

in which B', R, $R_1$, $R_2$, $R_{15}$, $R_{16}$ and Ts have the same meaning as above and the said 4-tosyl xyphenyl derivative is then detosylated by treatment a agent such as an alkali metal hydroxide, to provide the required compound of formula (4).

11) The compounds of formula (4) in which Cy represents an optionally mono- or di- substituted 2-R-furan-3-yl group can be obtained by oxidizing for instance with manganese oxide, a 4,5-dihydrofuran derivative of formula (30) to obtain a furan derivative of general formula:

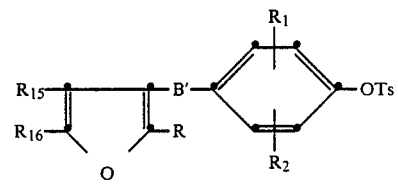  (31)

in which B', R, $R_1$, $R_2$, $R_{15}$, $R_{16}$ and Ts have the same meaning as above, which furan derivative is subsequently treated with a basic agent such as an alkali metal hydroxide, to obtain the required compound of formula (4).

12) The compounds of formula (4) in which Cy represents a 2-R-furan-3-yl or 2-R-thien-3-yl or 2-R-pyrrol-3-yl group can be prepared by reacting a compound of general formula:

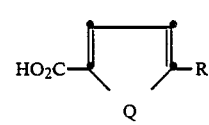  (32)

in which R has the same meaning as above and Q represents

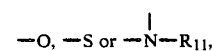

—O, —S or —N—$R_{11}$, with a halide of formula (9) in the presence of a Friedel-Crafts-catalyst such as aluminium chloride to obtain a 4-methoxy derivative of general formula:

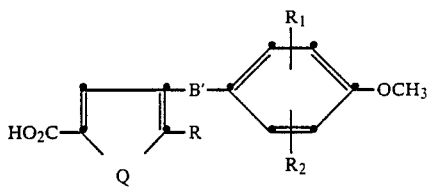

(33)

in which B', R, R$_1$, R$_2$ and Q have the same meaning as above, which is subsequently decarboxylated by heating and demethylated with an appropriate agent such as pyridine hydrochloride or aqueous hydrobromic acid, to provide the required compound of formula (4).

Alternatively, the compounds of formula (4) in which Cy represents an optionally substituted 2-R-furan-3-yl group can be prepared by oxidizing, for instance with manganese oxide, a sulphide derivative of formula (30) to obtain an optionally substituted 2-R-3(4-tosyloxybenzenesulphonyl)furan derivative which is subsequently treated by a basic medium for instance an alkali metal hydroxide, to provide the required compound of formula (4).

13) The compounds of formula (4) in which Cy represents a 1-R-imidazol-2-yl or 1-R-benzimidazol-2-yl group can be obtained by reacting a 1-R-imidazole or 1-R-benzimidazole with a halide of formula (9) in the presence of a Friedel-Crafts catalyst such as aluminium chloride, to obtain a compound of general formula:

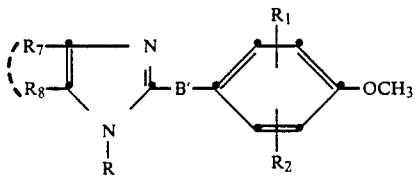

(34)

in which B', R, R$_1$ and R$_2$ have the same meaning as above, R$_7$ and R$_8$ each represent hydrogen or are taken together with the carbon atoms to which they are attached to form a phenyl group which is subsequently demethylated using an ethanethiol/aluminium chloride mixture or 2-mercaptoethanol in the presence of sodium hydride to obtain the required compound of formula (4). Compounds of formula (34) in which —OCH$_3$ is replaced by —O Benzyl can also be used. In such case the compounds of formula (34) in question are debenzylated using for instance palladium charcoal for obtaining the required compound of formula (4). When R represents hydrogen, imidazole or benzimidazole is protected in the 1-position with an appropriate N-protecting group for instance a benzyl group which can subsequently be removed, if desired, using classical procedures.

(14) The compounds of formula (4) in which Cy represents an optionally substituted 5-R-isoxazol-4-yl derivative can be prepared by reacting an isoxazole derivative of general formula:

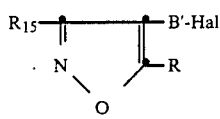

(35)

in which B', R, R$_{15}$ and Hal have the same meaning as above with a 4-methoxy derivative of formula (26) in the presence of a Friedel-Crafts catalyst such as aluminium chloride to obtain the compounds of general formula:

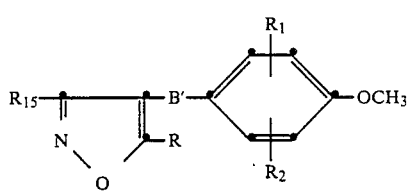

(36)

in which B', R, R$_1$, R$_2$ and R$_{15}$ have the same meaning as above, which is demethylated, using for instance aluminium chloride, to provide the required compound of formula (4).

Compounds of formula (35) are known products having been described in Gazz. Chim. Ital. 76, 30 (1946) while the other compounds of formula (35) can be obtained in accordance with the method described therein or classical methods. Alternatively, the compounds of formula (36) in which R$_{15}$ represents hydrogen and B' represents a —SO$_2$— group, can be obtained in accordance with the method described in J. Hetero. Chem. 23, 1363 (1986) by reacting a 1-(4-methoxy-benzenesulphonyl)-2-N,N-dimethylaminoethene with hydroxylamine. Similarly, compounds of formula (36) in which B' represents a —SO$_2$— group, R$_{15}$ is other than hydrogen and in which —OCH$_3$ is replaced by —O Tosyl can be used for obtaining the corresponding compounds of formula (4). These 3-substituted -5-R-4-(4-O-Tosyl)-benzenesulphonyl isoxazole derivatives can be prepared in accordance with the method described in Gazz. Chim. Ital. 98, 656 (1968) i.e. by reacting a benzenesulphonyl-ketone and an hydroxamic acid derivative.

15) The compounds of formula (4) in which Cy represents a 5-R-pyrazol-4-yl group can be prepared by reacting a compound of general formula:

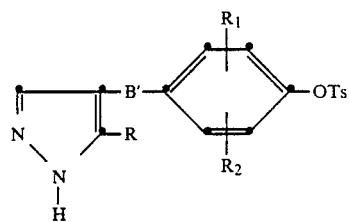

(37)

in which B', R, R$_1$, R$_2$ and Ts have the same meaning as above, with hydrazine, to obtain the required compound of formula (4). The compounds of formula (37) are compounds which can be prepared in accordance with J. Hetero. Chem., 23, 1363 (1986) i.e. from a N,N-dimethylaminoethene derivative and hydrazine. Alternatively the compounds of formula (4) in which Cy represents a 5-R-pyrazol-4-yl group can be directly obtained from a compound of general formula:

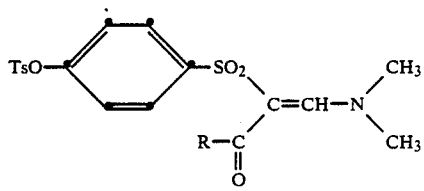
(38)

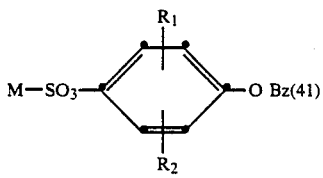
(41)

in which R and Ts have the same meaning as above, and hydrazine in excess. The compounds of formula (38) can be prepared in accordance with the method described in J. Hetero. Chem. 23, 1363 (1986) cited above.

The compounds of formula (4) in which Cy represents a 1-$R_{11}$-2-R-indol-3-yl or 1-$R_{11}$-3-R-indol-2-yl derivative can be prepared:

(a) when $R_{11}$ represents hydrogen, by reacting p-methoxythiophenol substituted by $R_1$ and $R_2$ groups, with 2-R-indole or 3-R-indole in the presence of iodine, to provide an indole derivative of general formula:

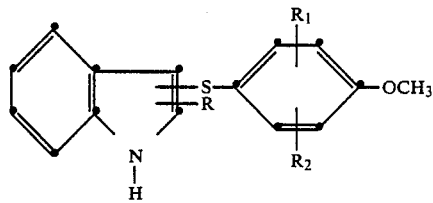
(39)

in which R, $R_1$ and $R_2$ have the same meaning as above, which can then be oxidized with 3-chloroperbenzoic acid to provide the sulphonyl derivatives of general formula:

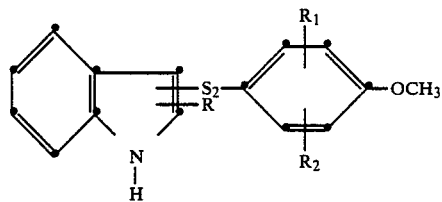
(40)

in which R, $R_1$ and $R_2$ have the same meaning as above. The compounds of formulae (39) and (40) can subsequently be demethylated using 2-mercaptoethanol in the presence of sodium hydride to provide the required compounds of formula (4).

(b) when $R_{11}$ is other than hydrogen, by treating a compound of formula (39) or (40) with an iodide of formula $R_{11}$—I in which $R_{11}$ is other than hydrogen and demethylating the 1-substituted derivative so obtained with 2-mercaptoethanol in the presence of sodium hydride, to provide the required compounds of formula (4).

(17) The compounds of formula (4) in which Cy represents a 2-R-5-$R_{11}$-4,5,6,7-tetrahydro-thieno[3,2-c]pyrid-3-yl group and B' represents a —$SO_2$— group can be prepared by reacting a 2-R-5-$R_{11}$-4,5,6,7-tetrahydro-thieno[3,2-c]pyridine in which $R_{11}$ is other than hydrogen with a compound of general formula:

in which $R_1$, $R_2$, M and Bz have the same meaning as above, in the presence of methanesulphonic acid/phosphorous pentoxide to obtain a tetrahydrothienopyridine of general formula:

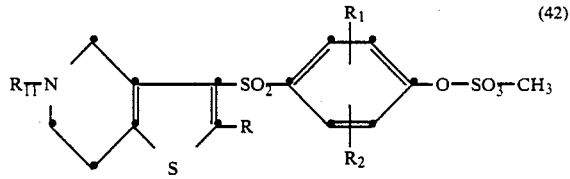
(42)

in which R, $R_1$ and $R_2$ have the same meaning as above and $R_{11}$ has the same meaning as above with the exception of hydrogen. The compounds of formula (42) are then hydrolysed in the presence of a basic agent such as an alkali metal hydroxide to provide the required compounds of formula (4) in which $R_{11}$ is other than hydrogen. Starting 2R-5-$R_{11}$-4,5,6,7-tetrahydro-thieno[3,2-c]pyridines are known compounds having been described in Heterocycles, 22, 235 (1984) or can be prepared in accordance with the method described therein.

(18) The compounds of formula (4) in which Cy represents a 2-R-thieno[3,2-c]pyrid-3-yl group can be prepared by hydrolising a compound of formula (42) in which $R_{11}$ represents a benzyl or halobenzyl radical and further reacting the 4-hydroxybenzenesulphonyl derivative so obtained with palladium charcoal in diphenylether to provide the required compound of formula (4).

(19) The compounds of formula (4) in which Cy represents a 5-R-thiazol-4-yl group can be prepared by demethylating a compound of general formula:

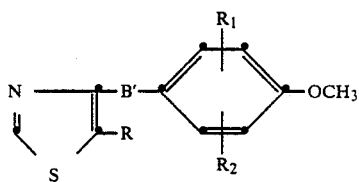
(43)

in which B', R, $R_1$ and $R_2$ have the same meaning as above, using hydrobromic acid in acetic acid, to provide the required compounds of formula (4). The compounds of formula (43) can be obtained in accordance with the method described in Tetrah. Lett 1972, p. 2777 i.e. from a sulphonylmethylisocyanide and a thioglycolic acid derivative.

(20) The compounds of formula (4) in which Cy represents a 1-$R_{11}$-5-R-imidazol-4-yl group can be obtained by demethylating with 2-mercaptoethanol in the presence of sodium hydride, a compound of general formula:

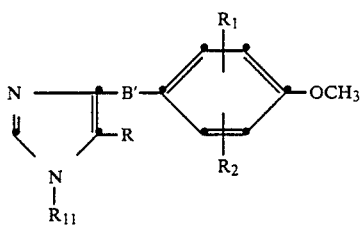 (44)

in which B', R, $R_1$, $R_2$ and $R_{11}$ have the same meaning as above, to provide the required compounds of formula (4). The compounds of formula (44) can be obtained in accordance with the method described in Tetrahedron Lett. 23, pp. 2373-2374 (1972) i.e. from a sulphonylmethylisocyanide and an imidazol derivative.

(21) The compounds of formula (4) in which B' represents a —SO$_2$— group and Cy represents a group of formula (D) in which $R_5$ and $R_6$ are taken together with the carbon atom to which they are attached to form a non aromatic mono- or di-cyclic carbocyclic group having from 5 to 10 carbon atoms and optionally substituted by a R group in the α-position with respect to the methyne group, for instance a 3-R-inden-2-yl, 2-R-cyclohexen-1-yl or 1-R-3,4-dihydro-naphth-2-yl group can be prepared, in accordance with the method described in J. Org. Chem. vol. 35, No. 12, pp. 4217-4222 (1970) by heating a compound of general formula:

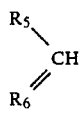 (45)

in which $R_5$ and $R_6$ are taken together with the carbon atom to which they are attached to form a group having from 5 to 10 carbon atoms and optionally substituted by a R group in the α-position with respect to the methyne group, with a halide of 4-tosyloxybenzene substituted by $R_1$ and $R_2$ groups in an appropriate solvent such as benzene and in the presence of anhydrous cupric chloride and triethylamine, to obtain a 4tosyloxyphenyl derivative of general formula:

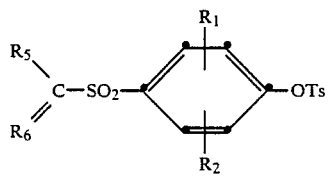 (46)

in which $R_1$, $R_2$ and Ts have the same meaning as above and $R_5$ and $R_6$ have the same meaning as in formula (37) which is then detosylated using an appropriate agent such as an alkali metal hydroxide to obtain the required compound of formula (4).

(b) Compounds of formula (4) in which Cy represents a group (E)

The compounds of formula (4) in which Cy represents a 2-R-imidazol-1-yl or 2-R-benzimidazol-1-yl group can be obtained by reacting a 2-R-imidazole or 2-R-benzimidazole with a halide of formula (9) in the presence of a Friedel-Crafts catalyst such as aluminium chloride, to provide a compound of general formula:

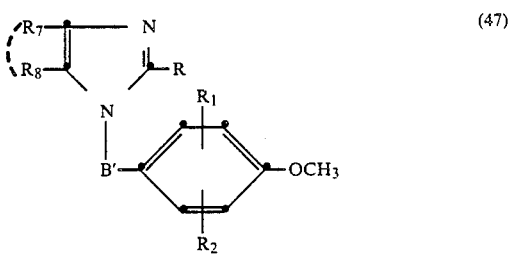 (47)

in which B', R, $R_1$ and $R_2$ have the same meaning as above and $R_7$ and $R_8$ each represent hydrogen or are taken together with the carbon atoms to which they are attached to form a phenyl group.

The compound of formula (47) is then demethylated using an appropriate agent for instance an ethanethiol/aluminium chloride mixture to give the required compound of formula (4).

(c) Compounds of formula (4) in which Cy represents a group (F)

The compounds of formula (4) in which Cy represents for instance a 2-R-chromon-3-yl group and B' represents a —SO$_2$— group can be prepared by reacting a 2-R-3-halogeno-chromone with a 4-methoxy derivative of formula (9) in which B' represents a —SO$_2$— group, in the presence of a Friedel-Crafts catalyst such as aluminium chloride, to obtain the chromone derivative of general formula:

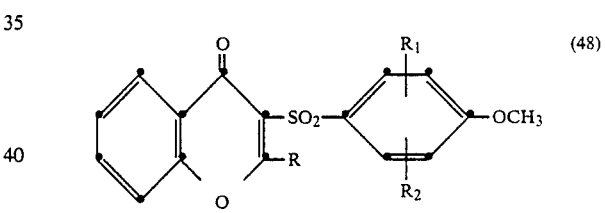 (48)

in which R, $R_1$ and $R_2$ have the same meaning as above, which is optionally demethylated using for instance aqueous hydrobromic acid or pyridine hydrochloride, to provide the required compound of formula (4).

(d) Compounds of formula (4) in which Cy represents a group (G)

The compounds of formula (4) in which Cy represents an optionally substituted 5-R-2,3-dihydro-furan-2-one-4-yl can be prepared by reacting, in basic medium, for instance potassium carbonate, a ketone of formula (18) with a 2-halogenoacetate of general formula:

 (49)

in which Hal, $R_{14}$ and $R_{15}$ have the same meaning as above, to obtain a ketoester which is first hydrolysed in basic medium and then treated with a strong acid to provide the carboxylic acid derivative of general formula:

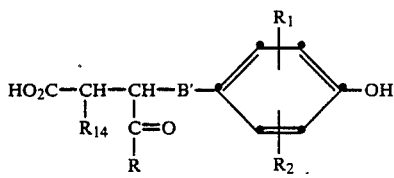

(50)

in which B', R, R₁, R₂ and R₁₄ have the same meaning as above.

The acid of formula (50) when treated with trifluoroacetic acid or thionyl chloride provides the required compound of formula (4)

(e) Compounds of formula (4) in which Cy represents a group (H)

The compounds of formula (4) in which Cy represents an optionally substituted 5-R-1,3-dihydro-2H-imidazol-2-one-4-yl can be obtained by reacting a 5-R-imidazol-2-one with a halide of formula (9) to obtain a compound of general formula:

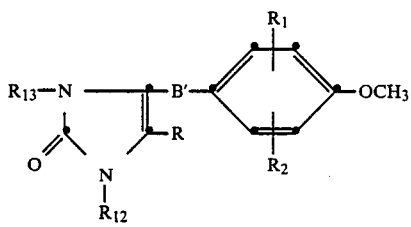

(51)

in which R, R₁, R₂, R₁₂, R₁₃ and B' have the same meaning as above which is subsequently demethylated using appropriate procedures such as in the presence of iodhydric acid, pyridine hydrochloride or hydrobromic acid, to obtain the required compound of formula (4).

As an alternative procedure, the compounds of formula (4) in question can be prepared by adapting the method similar to that described in J. Am. Chem. Soc. 68, p. 2350 (1946).

According to an alternative method, the compounds of formula (1) in which B represents a —S— or —SO₂— group and A represents an alkylene radical, preferably those in which A represents a propylene radical, can also be obtained by reacting, in the presence of a basic agent such as an alkali metal carbonate, for example potassium carbonate, an alkali metal hydroxide such as sodium or potassium hydroxide, an alkali metal hydride such as sodium hydride or an alkali metal alcoholate, for example sodium methylate or ethylate, a 4-hydroxyphenyl derivative of formula (4) above with a compound of general formula:

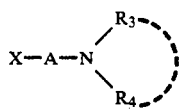

(52)

in which X has the same meaning as above and preferably represents chlorine or a benzenesulphonyloxy or p-toluenesulphonyloxy radical, A represents an alkylene radical and R₃ and R₄ have the same meaning as above, the reaction taking place at a temperature between room-temperature and the refluxing temperature of the medium and in a polar solvent such as methyl ethyl ketone or dimethylsulphoxide to form the desired aminoalkoxyphenyl derivative of formula (1) in the form of the free base.

When R₄ represents hydrogen, the nitrogen atom is preferably protected by a labile group for instance a protecting group which can be eliminated in basic medium for example the tertiobutoxycarbonyl (BOC) group.

The compounds of formula (52) are products which are known or which can be prepared by known methods.

The compounds of formula (1) in which Cy represents a group (E), A represents an alkylene chain and B represents a —S— or —SO₂— group can also be prepared by reacting a 2-R-imidazole or 2-R-benzimidazole with a halide of general formula:

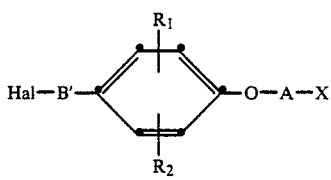

(53)

in which B', R₁, R₂, Hal and X have the same meaning as above and A represents an alkylene chain, in the presence of an acid acceptor such as triethylamine to obtain a compound of general formula:

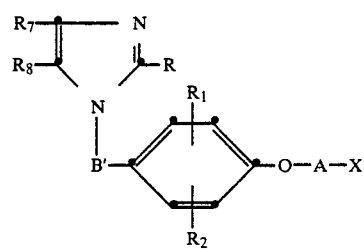

(54)

in which B', R, R₁, R₂ and X have the same meaning as above, R₇ and R₈ each represent hydrogen or are taken together with the carbon atom to which they are attached to form a phenyl group and A represents an alkylene chain, which compound is subsequently reacted with an amine of formula (3) to obtain the required compound of formula (1) in the form of a free base.

Similarly, the compounds of formula (1) in which Cy represents an optionally mono- or di- substituted 2-R-4,5-dihydro-furan-3-yl group, A represents an alkylene chain and B represents a —S— or —SO₂— group, can be prepared by hydrolysing a cyclopropane derivative of formula (29) in the presence of an aqueous alkali metal hydroxide solution to provide a 4-methoxyphenyl derivative of general formula:

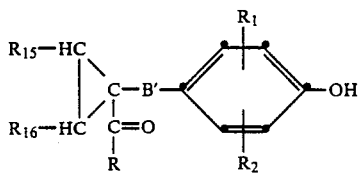

(55)

in which B', R, R₁, R₂, R₁₅ and R₁₆ have the same meaning as above, which is then reacted:
  with a dihaloalkane of formula (5) and the resulting product with an amine of formula (3) or with a compound of general formula (52), to provide an aminoalkoxyphenyl derivative of general formula:

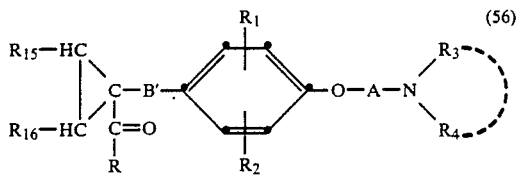

in which B', R, $R_1$, $R_2$, $R_3$, $R_4$, $R_{15}$ and $R_{16}$ have the same meaning as above and A represents an alkylene chain.

The cyclopropane derivative of formula (56) is subsequently heated between 100 and 130° C. in the presence of a phase transfer catalyst such as for instance triphenylphosphine or tricaprylylmethyl ammonium chloride to provide the required 2,3-dihydrofuran derivative of formula (1) in the form of a free base.

II. When B represents a —SO— group, by treating, with an oxidizing agent, a sulphide of formula (1) in which B represents a —S— group, this compound of formula (1) being in the form of the free base of a salt thereof so as to obtain the required compound in the form of the free base or a salt thereof.

Where the required compound is provided in the form of a salt, the free base thereof can be recovered by treatment with a basic agent such as an alkali metal carbonate for example potassium carbonate or an alkali metal bicarbonate for example sodium bicarbonate.

Generally, the reaction takes place in water or in an organic solvent such as methylene chloride and in the presence of a suitable oxidizing agent such as for example sodium periodate, potassium permanganate or 3-chloroperbenzoic acid.

Depending on the oxidizing agent used, mixtures of sulphoxides or sulphones can be obtained. These mixtures can be separated by conventional procedures for instance by chromatography.

III. When B represents a —S— or —SO$_2$— group and A represents an optionally substituted 2-hydroxypropylene chain, by reacting under reflux a 4-hydroxyphenyl derivative of formula (4) with an epihalohydrin, such as epichlorhydrin or epibromhydrin in dextrorotatory or laevorotatory form or in the form of a mixture of these isomers, for example in racemic form, and in the presence of a basic agent such as an alkali metal carbonate, for example potassium carbonate, an alkali metal hydroxyde, for example sodium or potassium hydroxide, an alkali metal hydride, such as sodium hydride or an alkali metal alcoholate, for example sodium methylate of ethylate, and in a polar solvent such as methyl ethyl ketone to give the oxiranylmethoxy derivatives of general formula:

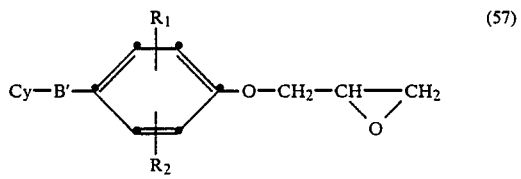

in which Cy, B', $R_1$ and $R_2$ have the same meaning as above.

The oxyranylmethoxy derivatives of formula are then treated under reflux with an amine of formula (3), this being performed in a polar solvent such as methyl ethyl ketone or in an excess of amine of formula (3) to give the desired compound of formula (1) in the form of the free base in which A represents a 2-hydroxypropylene chain which can be reacted, if desired, with a lower alkyl halide in the presence of a strong base to provide the compound of formula (1) inthe form of the free base in which A represents a 2-hydroxypropylene chain in which the hydroxy is substituted by a lower alkyl radical.

In some cases, by-products may be formed in parallel with the compounds of formula (57) above, on this case 4-(3-halo-2-hydroxypropoxy)benzenesulphonyl derivatives.

On reaction with the amine of formula (3), these derivatives will nevertheless give rise to the desired compounds of formula (1) in which A represents a 2-hydroxypropylene chain.

The compounds of formula (7) thereby obtained in the form of the free base can then be converted to pharmaceutically acceptable salts by reaction with a suitable organic or inorganic acid, for example oxalic, maleic, fumaric, methanesulphonic, benzoic, ascorbic, pamoic, succinic, hexamic, bismethylenesalicyclic, ethanedisulphonic, acetic, propionic, tartaric, salicylic, citric, gluconic, lactic, malic, cinnamic, mandelic, citraconic, aspartic, palmitic, stearic, itaconic, qlycolic, p-aminobenzoic, glutamic, benzenesulphonic or theophyllineacetic acid or with lysine or histidine.

Similarly, the N-oxide derivatives of the compounds of formula (1) can be formed by oxidizing the compound of formula (1) in question with an appropriate oxidizing agent for instance hydrogen peroxide or 3-chloroperbenzoic acid.

Monoalkyl- or dialkylaminoalkoxybenzenesulphonyl-benzofuran or benzothiophene derivatives are reported in U.S. Pat. No. 4,117,128 as presenting pharmacological effects in the cardiovascular field.

In the course of the elaboration of the present invention, tests were carried out with compounds specifically cited in the aforesaid U.S. patent, more particularly with 2-ethyl- or 2-n-butyl-3-[4-(2-diethylaminoethoxy)-benzenesulphenyl]benzofuran.

From results of these tests, it could be concluded that in the dog at the dose of 10 mg/kg by intravenous route, these known compounds only present a weakα-antiadrenergic activity and no or practically no β-antiadrenergic effect.

It has now been surprisingly discovered, in the context of the present invention, that by replacing the mono- or di-alkylaminoalkoxy chain of the benzenesulphonyl-benzofurans or benzothiophenes of the prior art by an aralkylaminoalkoxy chain, compounds are obtained which show much greater α- and β-antiadrenergic activities than those of the known compounds in question.

For instance, aralkylaminoalkoxybenzenesulphonyl-benzofurans or benzothiophenes in question have shown, at doses as low as 0.1 to 1.5 mg/kg, sub-total inhibition of the α-adrenergic effect together with an important β-antiadrenergic action.

Such very valuable antiadrenergic properties were also found to be present in compounds similar in structure to the aralkylaminoalkoxybenzenesulphonyl-benzofurans and benzothiophenes in question but in which the benzofuran or benzothiophene moiety is replaced by another carbocyclic or heterocyclic group.

Therefore, one class of compounds of the invention relates to those compounds of formula (1) and the pharmaceutically acceptable salts or Noxide thereof, in which Cy, $R_1$, $R_2$, $R_4$ and A have the same meaning as in formula (1), B represents a —$SO_2$— group and $R_3$ represents a radical —Alk—Ar.

A particularly valuable class of compounds of the invention are those in which $R_1$, $R_2$, $R_4$ and A have the same meaning as in formula I, B represents a —$SO_2$— group, $R_3$ represents a radical —Alk—Ar, Cy represents a group selected from:

indolizin-3-yl benzofuryl or benzothienyl more particularly 2-R-benzofur-3-yl and 2-R-benzothien-3-yl quinolinyl such as 2-R-quinolin-3-yl pyrrolo[1,2-b]pyridazinyl more particularly 6-R-pyrrolo[1,2-b]pyridazin-5-yl pyrazolo[1,5-a]pyridyl more particularly 2-R-pyrazolo[1,5-a]pyrid-3-yl imidazo[1,2-a]pyridyl more particularly 2-R-imidazo[1,2-a]pyrid-3-yl 4,5-dihydrofuranyl more particularly 2-R-3,4-dihydrofuran-3-yl phenyl more particularly 2-R-phenyl naphthyl more particularly 2-R-1-naphthyl indolyl more particularly 2-R-indol-3-yl or 1-$R_{11}$-2-R-indol-3-yl group.

Similarly indolizine derivatives which are substituted in the 1-position with an alkoxybenzoyl chain which is itself substituted with a mono- or dialkylamino group, and which are stated to have pharmacological effects in the cardiovascular field, are already known.

In this connection, there may be mentioned French Patent No. 2,341,578 and Eur. J. Med. Chem. 1977, 12, No. 4pp. 345–350, which specifically describe 2-ethyl-, 2-n-propyl- or 2-n-butyl-1-[4-(3-di-n-propyl- or 3-di-n-butylaminopropoxy)benzoyl]indolizine optionally dimethylated on the benzoyl radical.

These known compounds showed antiadrenergic activities which were nonexistent or low, at all events too low to be of any value for therapy.

Other monoalkyl- or dialkyl-aminoalkoxybenzoyl derivatives are also known.

For instance are reported in the literature monoalkyl- or dialkyl-aminoalkoxybenzoyl derivatives of:

thiophene [(J. Med. Chem. V, 13 (3) pp. 359–366 (1970)]

naphthalene or dihydronaphthalene (Chim. Ther. V, 7 (5) pp. 369–377)

pyridine [Ing. Chim. V, 59 (283) pp. 3—13 (1977)]

thieno[3,2-c]pyridine [Heterocycles, V, 22 (5), pp. 1235–1247 (1984)]

indole [Eur. J Med. Chem. - Chim. Ther. V, 12 (5) pp. 483–487 (1977)]

furan (French patent No. 2,400,515)

chromone (U.S. Pat. No. 4,220,645)

Tests carried out with these known compounds showed that same of them presented antiadrenergic activities but which were low, at all events too low to be of any value for therapy.

It has now been found, in addition, that mono- or di-alkylaminoalkoxy benzenesulphonyl derivatives resembling those described in U.S. Pat. No. 4,117,128 but in which the benzofuran or benzothiophene moiety has been replaced by another carbocyclic or heterocyclic ring present more valuable antiadrenergic properties than known sulphonyl derivatives of the aforesaid U.S. patent or known benzoyl derivatives of the above-cited references.

For instance, α- and β-antiadrenergic properties were registered, in the dog by intravenous route at doses as low as 0.1 to 1.5 mg/kg with respect to mono- or dialkylaminoalkoxybenzenesulphonyl derivatives of formula (1) in which Cy represents another group than benzofuryl or benzothienyl for instance a quinolinyl or pyrrolo[1,2-b]pyridazinyl moiety.

Yet, another valuable class of compounds of the invention are those in which $R_1$, $R_2$, $R_4$ and A have the same meaning as in formula (1), B represents a —$SO_2$— group and $R_3$ represents an alkyl radical with the proviso that Cy is different from benzo[b]furyl or benzo[b]thienyl.

A particularly valuable class of compounds of the invention are those in which $R_1$, $R_2$, $R_4$ and A have the same meaning as in formula (1), B represents a —$SO_2$— group, $R_3$ represents an alkyl radical and Cy represents a group selected from:

quinolinyl more particularly 2-R-quinolin-3-yl pyrrolo[1,2-b]pyridazinyl more particularly 6-R-pyrrolo[1,2-b]pyridazin-5-yl.

pyrazolo[1,5-a]pyridyl more particularly 2-R-pyrazolo[1,5-a]pyrid-3-yl.

imidazo[1,2-a]pyridyl more particularly 2-R-imidazo[1,2-a]pyrid-3-yl.

4,5-dihydrofuranyl more particularly 2-R-4,5-dihydrofuran-3-yl group.

indolyl more particularly 2-R-indol-3-yl and 1-$R_{11}$-2-R-indol-3-yl.

indolizin-3-yl.

Moreover, it has been found that the calcium inhibitory activity of the compounds of the invention is at least equal to, if not greater than, that observed in tests performed with the known compounds. In contrast to the known compounds, it has thus been possible to demonstrate for the compounds of the present invention a pharmacological spectrum revealing anticalcium and α-and β-antiadrenergic components with a balanced intensity which is of therapeutic value, for example, for treatment of angina.

As has been reported in detail by R. Charlier in "Bruxelles Medical", No. 9, September 1969, pages 543–560, it is accepted than an antianginal drug treatment should be capable, in particular, of antagonizing the antiadrenergic type cardiovascular reactions. To this end, agents capable of blocking the α-receptors have been proposed.

However, the clinical application of such compounds to the treatment of angina remained unsuccessful, very probably due to the fact that α-receptor antagonists induce only a very partial neutralization of the adrenergic system the activity of the β-receptors being unaffected.

In fact, the most undesirable haemodynamic manifestations which occur in angina pectoris patients during their painful attacks are, most of all, cardiac, and consequently involve the β-receptors.

In parallel, treatments have been proposed with drugs which are β-adrenergic receptor antagonists. These compounds, which are of genuine clinical value, decrease the attacks of angina by reducing the work of the heat by slowing the heart rate. However, there is no fall in the peripheral arterial resistance which, on the contrary, rises through release of the α-tonicity.

These drug treatments nevertheless modify some haemodynamic parameters in a direction which, at a fundamental level, detracts from the value of these drugs for angina pectoris patients in particular and heart patients in general.

If the antiadrenergic aspect of β-blockers is considered, it becomes clear that only the tachycardia and the increase in the force and the speed of contraction of the heart are capable of being neutralized, the arterial hypertension involving a stimulation of the α-receptors on which βantagonists have no action.

In fact, while the cardiovascular disturbances brought about by the stimulation of the β-receptors are the more harmful to angina patients, it is nonetheless true that arterial hypertension also plays a not insignificant part.

In addition, blocking the β-receptors involves a risk, depriving the patient suffering from cardiac insufficiency of a compensatory mechanism which he normally brings into play to limit his circulatory insufficiency.

This reflex mechanism, the main component of which makes use of the pathway of the β-adrenergic system, leads, in particular, to an increase in the force and the speed of contraction of the heart. In consequence, if this system is blocked, the patient suffering from cardiac insufficiency experiences a worsening of his functional breakdown. It is hence logical to consider that the use of a β-blocker whose action is pure and complete will always involve a cardiac risk.

It hence appears to be desirable not to seek complete α- or β-antagonistic properties, given the clinical side effects that these can bring about. It seems more logical to aim to subdue rather than to eliminate the cardiovascular disturbances which characterize the hyperstimulation of the adrenergic system as a whole.

The compounds of the invention meet this objective since they show incomplete α- and β-type antiadrenergic properties. They can hence be considered, not as β-blockers but as adreno-decelerators, that is to say partial antagonists of the α- and β-adrenergic reactions, potentially devoid of the disadvantages listed above for β-blockers.

In addition, the calcium inhibitory component demonstrated in the compounds of the invention will act as an exceptional complement to the pharmacological spectrum of their cardiovascular action.

It is known, in effect, that the transport of calcium ions is one of the main components of the action potential in heart cells and, in consequence, this transport plays a fundamental part in the electrical conduction as well as in the disorders which may occur therein (arrhythmia). In addition, it is known that calcium ions are involved in the excitation-contraction coupling which controls the degree of vasoconstriction in smooth muscle and, in the same circumstances, plays a critical part in attacks of angina pectoris.

Compounds which are calcium antagonists act at the level of the cell membrane by selectively preventing calcium from participating int he process of contraction within the arterial cell.

In fact, it appears increasingly clear, at the present time, that the clinical results provided by the combination of calcium inhibitors and β-adrenergic inhibitors are better than when each inhibitor is used separately (J.A.M.A. 1982, 247, pages 1911-1917).

It appears, moreover, that no β-blocker which exerts, in addition, a significant inhibitory action in respect of calcium transport exists at the present time.

From this standpoint, the compounds of the invention possessing both an anticalcium component and an α- and β-antiadrenergic component will be of fundamental value, since they are capable of more extensive therapeutic applications than a separate β-blocker or a separate calcium inhibitor. Compounds of the invention possess an α- and β-antiadrenergic component reinforced by an oxygen-economizing effect capable of providing a therapeutic effect in man in the syndrome of angina of effort, which can, moreover, be treated by traditional β-blockers. However, the major advantage of these compounds will reside in the fact that they may, as a result of their anti-calcium effect, be used in the treatment of angina at rest, a syndrome induced by the appearance of a spasm in the coronary arteries, which is combated at present by compounds such as diltiazem, verapamil or nifedipine.

In addition, compounds of the invention were also shown to be capable of inducing a substantial increase in the coronary flow.

The results of pharmacological tests performed for the purpose of determining the cardiovascular properties of the compounds of the invention are recorded below.

I. Calcium inhibitory properties

The properties of inhibiting calcium transport at the membrane level shown by the compounds of the invention were demonstrated by measuring their antagonistic action with respect to the contractile response to potassium-induced depolarization on isolated rat aorta. It is well established that the depolarization of a smooth muscle membrane by potassium renders the latter permeable to extracellular calcium and induces muscle contraction.

Consequently, the measurement of the inhibition of the contractile response to depolarization by potassium, or the measurement of a relaxation of the tonic contraction on potassium depolarization, can represent an evaluation of the power of a compound as an inhibitor of the membrane permeability of $CA^{++}$ ions.

The technique used was as follows:

The aorta was removed from male Wistar rats weighing approximately 300 g, and cut into strips approximately 40 mm long and 3 mm wide.

These fragments were placed in a 25-ml isolated organ trough containing a modified Krebs-bicarbonate solution (112 nM NaCl; 5 mM KCl: 25 mM $NaCO_3$: 1 mM $KH_2PO_4$; 1.2 mM $MgSO_4$; 2.5 mM $CaCl_2$; 11.5 mM glucose, distilled water to 1000 ml) through which a stream of 5-7% carbon dioxide in oxygen was passed, and maintained at 37° C. The preparation was connected to a force microsensor and the contractile response recorded after amplification on a recorder.

A tension of 2 g was applied to the preparation. This tension was maintained for 60 minutes in the modified Krebs-bicarbonate solution, and contractions were then induced by replacing the Krebs-bicarbonate solution by a potassium-Krebs solution (17 mM NaCl; 100 mM KCl; 25 mM $NaHCO_2$; 1 mM $KH_2PO_4$; 1.2 mM $MgSO_4$; 2.5 mM $CaCl_2$; 11.5 mM glucose; distilled water to 1000 ml). When the contractile response of the preparation had become reproducible, a given amount of a compound of the invention was introduced into the bath. Sixty minutes later, a new spasm was induced by potassium depolarization.

The results obtained on the aorta used in the experiment were than expressed as a percentage of the maximum contractional effect before incubation with the test substance.

By way of examples, the results which follow were obtained, the compounds of formula (1) being in the form of the base, hydrochloride or oxalate.

General structure: Cy—SO$_2$—C$_6$H$_4$—O—(CH$_2$)$_3$—Am

| Compound | Cy | n | Am | % of the maximum contractional effect |||| 
|---|---|---|---|---|---|---|---|
| | | | | $10^{-6}$ M | $10^{-7}$ M | $10^{-8}$ M | $10^{-9}$ M |
| Ex.20 | 8-methylquinolin-2-yl (C$_3$H$_7$-iso substituted) | | —N(n-C$_4$H$_9$)$_2$ | 22.4 | 67.3 | — | — |
| Ex.21 | 8-methylquinolin-2-yl (C$_3$H$_7$-iso substituted) | | —N(CH$_3$)—(CH$_2$)$_2$—C$_6$H$_3$(OCH$_3$)$_2$ | 3.7 | 54 | 89.7 | — |
| Ex.16 | pyrazolo-pyridinyl (C$_3$H$_7$-iso substituted) | | —N(n-C$_4$H$_9$)$_2$ | 0 | 18.9 | 83 | — |
| Ex.17 | pyrazolo-pyridinyl (C$_3$H$_7$-iso substituted) | | —N(CH$_3$)—(CH$_2$)$_2$—C$_6$H$_3$(OCH$_3$)$_2$ | 0 | 15.1 | 67.1 | 84.9 |
| Ex.18 | pyrazolo-pyridinyl (C$_3$H$_7$-iso substituted) | | —NH—C(CH$_3$)$_3$ | 13.2 | 66.5 | 84 | — |
| Ex.22 | pyrazolo-pyridinyl (C$_3$H$_7$-iso substituted) | | —N(CH$_3$)—(CH$_2$)$_2$—C$_6$H$_3$(OCH$_3$)$_2$ | — | 0 | 18.1 | 68.1 |
| Ex.9 | phenyl | | —N(CH$_3$)—(CH$_2$)$_2$—C$_6$H$_3$(OCH$_3$)$_2$ | 21.4 | 73.7 | — | — |

-continued
| Compound | Cy | n | Am | % of the maximum contractional effect | | | |
|---|---|---|---|---|---|---|---|
| | | | | $10^{-6}$ M | $10^{-7}$ M | $10^{-8}$ M | $10^{-9}$ M |
| Ex.10 | 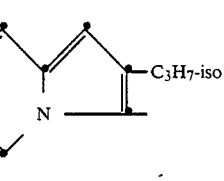 | | —N(n-C$_4$H$_9$)$_2$ | 32.4 | 85.3 | — | — |
| Ex.11 | 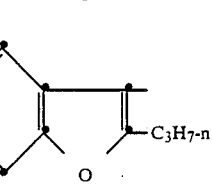 | | —N(n-C$_4$H$_9$)$_2$ | 47.5 | 64.8 | — | — |
| Ex.1 | 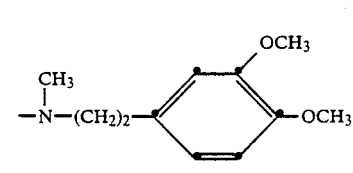 | | 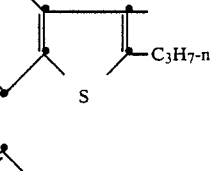 | — | 9.5 | 34.1 | 68.7 |
| Ex.12 | 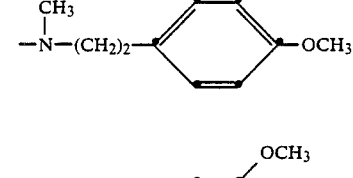 | | 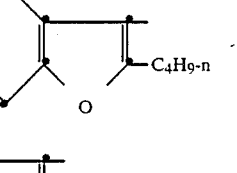 | 2.6 | 19.7 | 60.4 | 81.7 |
| Ex.13 | 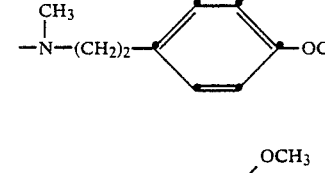 | | 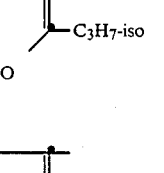 | 9.3 | 38.3 | 80.9 | — |
| Ex.14 | 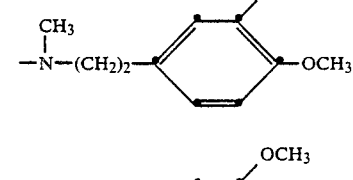 | | 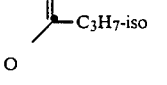 | 9.7 | 45.3 | 68.9 | — |
| Ex.15 | 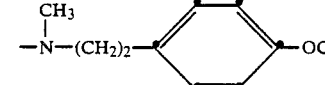 | |  | 36.8 | 59 | 76 | — |
| Ex.19 |  | |  | 8.2 | 66.7 | 78.3 | — |
| Ex.23 |  | |  | — | 43.2 | 86 | 89.8 |

-continued

| Compound | Cy | n | Am | % of the maximum contractional effect | | | |
|---|---|---|---|---|---|---|---|
| | | | | $10^{-6}$ M | $10^{-7}$ M | $10^{-8}$ M | $10^{-9}$ M |
| Ex.24 | furan with C$_3$H$_7$-iso | | —N(n-C$_4$H$_9$)$_2$ | 4.0 | 59.4 | 90.3 | — |
| Ex.25 | furan with C$_3$H$_7$-iso | | —NH—C(CH$_3$)$_3$ | 10.3 | 77.9 | 94.3 | — |
| Ex.60 | phenyl with C$_3$H$_7$-iso | | —N(CH$_3$)—(CH$_2$)$_2$—C$_6$H$_3$(OCH$_3$)$_2$ | 3.7 | 21.7 | 59.3 | 93.3 |
| Ex.61 | phenyl with C$_3$H$_7$-iso | | —N—(n-C$_4$H$_9$)$_2$ | — | 43.2 | — | 89.1 |
| Ex.49 | naphthyl | | —N(CH$_3$)—(CH$_2$)$_2$—C$_6$H$_3$(OCH$_3$)$_2$ | 16.8 | 62.8 | 83.3 | — |
| Ex.63 | phenyl with C$_2$H$_5$ | | —N—(n-C$_4$H$_9$)$_2$ | 4.2 | 43.4 | 85.1 | — |
| Ex.55 | N-methyl indole with C$_3$H$_7$-iso | | —N(CH$_3$)—(CH$_2$)$_2$—C$_6$H$_3$(OCH$_3$)$_2$ | 0 | 5.1 | 34.5 | 71.4 |
| Ex.52 | indole (NH) with C$_3$H$_7$-iso | | —N—(n-C$_4$H$_9$)$_2$ | 4.9 | 37.4 | 66.0 | — |
| Ex.56 | N-methyl indole with C$_3$H$_7$-iso | | —N—(n-C$_4$H$_9$)$_2$ | 0 | 15.1 | 71.0 | 84.6 |

-continued

| Compound | Cy | n | Am | % of the maximum contractional effect | | | |
|---|---|---|---|---|---|---|---|
| | | | | $10^{-6}$ M | $10^{-7}$ M | $10^{-8}$ M | $10^{-9}$ M |
| Ex.34 | benzofuran-C$_3$H$_7$-iso | | —N(CH$_3$)—CH$_2$—(3,4-dimethoxyphenyl) | 8.7 | 11.2 | 61.9 | 87.0 |
| Ex.36 | benzofuran-C$_3$H$_7$-iso | | —NH—(CH$_2$)$_2$—(3,4-dimethoxyphenyl) | 0 | 21.3 | 56.9 | — |
| Ex.66 | 2-Cl-benzyl-N-(thiophene-C$_2$H$_5$) | | —N(CH$_3$)—(CH$_2$)$_2$—(3,4-dimethoxyphenyl) | 59.8 | 68.7 | 91.4 | — |
| Ex.70 | benzothiazole | | —N—(n-C$_4$H$_9$)$_2$ | 13.7 | 66.7 | 90.6 | — |
| Ex.72 | benzisoxazole-C$_3$H$_7$-iso | | —N—(n-C$_4$H$_9$)$_2$ | 10.0 | 38.7 | 75.8 | — |
| Ex.41 | benzofuran-C$_3$H$_7$-iso | | —NH—(CH$_2$)$_2$—(3,4-methylenedioxyphenyl) | 13.6 | 50.6 | 81.4 | — |
| Ex.67 | 2-Cl-benzyl-N-(thiophene-C$_2$H$_5$) | | —N—(n-C$_4$H$_9$)$_2$ | 66.2 | 77.5 | 85.7 | — |
| Ex.57 | N-methylindole-C$_3$H$_7$-iso | | —N(CH$_3$)—CH$_2$—(3,4-dimethoxyphenyl) | — | 11.8 | 25.0 | 81.8 |
| Ex.58 | N-methylindole-C$_3$H$_7$-iso | | —NHC—(CH$_3$)$_3$ | 8.1 | 51.7 | 84.5 | — |

-continued

| Compound | Cy | n | Am | % of the maximum contractional effect | | | |
|---|---|---|---|---|---|---|---|
| | | | | $10^{-6}$ M | $10^{-7}$ M | $10^{-8}$ M | $10^{-9}$ M |
| Ex.69 | pyrrolo-pyridine, $C_2H_5$ | | $-N-(n\text{-}C_4H_9)_2$ | 5.8 | 16.8 | 54.6 | 75.3 |
| Ex.68 | pyrrolo-pyridine, $C_3H_7\text{-}iso$ | | $-NH-C-(CH_3)_3$ | 5.4 | 28.1 | 76.1 | 92.5 |
| Ex.64 | phenyl, $C_3H_7\text{-}iso$ | | $-NH-C-(CH_3)_3$ | 2.7 | 52.2 | 92.3 | — |
| Ex.62 | phenyl, $C_2H_5$ | | $-N(CH_3)-(CH_2)_2-\text{aryl}(OCH_3)_2$ | — | 6.0 | 66.1 | 84.8 |
| Ex.51 | indole-NH, $C_3H_7\text{-}iso$ | | $-N(CH_3)-(CH_2)_2-\text{aryl}(OCH_3)_2$ | — | 11.9 | 62.9 | 83.6 |
| Ex.59 | indole-NCH$_3$, $C_3H_7\text{-}iso$ | | $-N(CH_3)-(CH_2)_2-\text{aryl}(OCH_3)_2$ | — | — | 41.1 | — |

$$Cy-SO_2-\text{phenyl}-O-(CH_2)_n-Am$$

| Compound | Cy | n | Am | $10^{-6}$ M | $10^{-7}$ M | $10^{-8}$ M | $10^{-9}$ M |
|---|---|---|---|---|---|---|---|
| Ex.35 | benzofuran, $C_3H_7\text{-}iso$ | 2 | $-NH-CH_3\text{-}CH_2-\text{aryl}(OCH_3)_2$ | — | 4.7 | 53.3 | 83.9 |
| Ex.37 | benzofuran, $C_3H_7\text{-}iso$ | 2 | $-N(CH_3)-(CH_2)_2-\text{aryl}(OCH_3)_2$ | — | 11.1 | 53.9 | — |

-continued

| Compound | Cy | n | Am | % of the maximum contractional effect | | | |
|---|---|---|---|---|---|---|---|
| | | | | $10^{-6}$ M | $10^{-7}$ M | $10^{-8}$ M | $10^{-9}$ M |
| Ex.38 | 2-isopropyl-benzofuran-3-yl | 4 | $-N(CH_3)-CH_2-C_6H_3(OCH_3)_2$ | 3.8 | 31.5 | 61.0 | 80.8 |
| Ex.39 | 2-isopropyl-benzofuran-3-yl | 4 | $-N(CH_3)-(CH_2)_2-C_6H_3(OCH_3)_2$ | — | 33.6 | 53.1 | — |

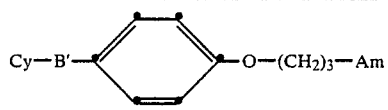

| Comp. | Cy | B' | Am | % of the maximum contractional effect | | |
|---|---|---|---|---|---|---|
| | | | | $10^{-5}$ M | $10^{-6}$ M | $10^{-7}$ M |
| Ex. 5 | 2-pyridyl | $-SO_2-$ | $-N(CH_3)-(CH_2)_2-C_6H_3(OCH_3)_2$ | 33.3 | 81.7 | 87.5 |
| Ex. 4 | 2-pyridyl | $-SO_2-$ | $-N(n-C_4H_9)_2$ | 37 | 84.7 | 88.9 |
| Ex. 8 | 2-pyridyl | $-SO_2-$ | $-NH-C(CH_3)_3$ | 70.6 | 87.1 | — |
| Ex. 6 | 3-pyridyl | $-SO_2-$ | $-N(n-C_4H_9)_2$ | 20.2 | 75.5 | 89.7 |
| Ex. 7 | 3-pyridyl | $-SO_2-$ | $-N(CH_3)-(CH_2)_2-C_6H_3(OCH_3)_2$ | 14 | 70.7 | 88 |
| Ex. 2 | 3-pyridyl | $-S-$ | $-N(n-C_4H_9)_2$ | 2.6 | 58 | 86.2 |

-continued

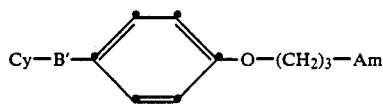

| Comp. | Cy | B' | Am | % of the maximum contractional effect | | |
|---|---|---|---|---|---|---|
| | | | | $10^{-5}$ M | $10^{-6}$ M | $10^{-7}$ M |
| Ex. 3 | pyridine | —S— | —N(CH$_3$)—(CH$_2$)$_2$—(3,4-dimethoxyphenyl) | 3.1 | 59 | 85 |
| Ex. 26 | cinnoline | —S— | —N(CH$_3$)—(CH$_2$)$_2$—(3,4-dimethoxyphenyl) | 3.0 | 64.2 | 85.4 |
| Ex. 28 | cinnoline | —SO$_2$— | —N(CH$_3$)—(CH$_2$)$_2$—(3,4-dimethoxyphenyl) | 19.2 | 73.1 | 86.6 |
| Ex. 27 | cinnoline | —S— | —N(CH$_3$)—(CH$_2$)$_2$—(3,4-dimethoxyphenyl) | 6.7 | 55.0 | 90.2 |
| Ex. 21 | N-isopropyl-indazole | —SO$_2$— | —N(CH$_3$)—(CH$_2$)$_2$—(3,4-dimethoxyphenyl) | — | 26.9 | 79.6 |
| Ex. 73 | naphthalene | —SO$_2$— | —N-(n-C$_4$H$_9$)$_2$ | — | 50.7 | 86.2 |
| Ex. 43 | N-benzyl-imidazole | —SO$_2$— | —N(CH$_3$)—(CH$_2$)$_2$—(3,4-dimethoxyphenyl) | 23.5 | 66.7 | 87.5 |

-continued

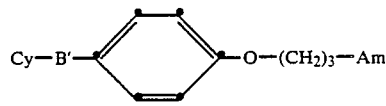

| Comp. | Cy | B' | Am | % of the maximum contractional effect | | |
|---|---|---|---|---|---|---|
| | | | | $10^{-5}$ M | $10^{-6}$ M | $10^{-7}$ M |
| Ex. 42 | pyrazine with N-CH(CH$_3$)$_2$ | —SO$_2$— | —N(CH$_3$)—(CH$_2$)$_2$—(3,4-dimethoxyphenyl) | 65.8 | 92.4 | 87.3 |
| Ex. 46 | pyrazole with C$_3$H$_7$-iso, NH | —SO$_2$— | —N(CH$_3$)—(CH$_2$)$_2$—(3,4-dimethoxyphenyl) | 15.1 | 62.5 | 87.6 |
| Ex. 65 | 2-ethylphenyl | —SO$_2$— | —NHC(CH$_3$)$_3$ | — | 32.0 | 83.3 |
| Ex. 71 | pyrazole with C$_3$H$_7$-iso, NH | —SO$_2$— | —N-(n-C$_4$H$_9$)$_2$ | 38.6 | 79.3 | 90.4 |
| Ex. 26 | methylcinnoline | —SO$_2$— | —N(CH$_3$)—(CH$_2$)$_2$—(3,4-dimethoxyphenyl) | 19.2 | 73.1 | 86.6 |

By way of comparison, the following results were obtained with known compounds:

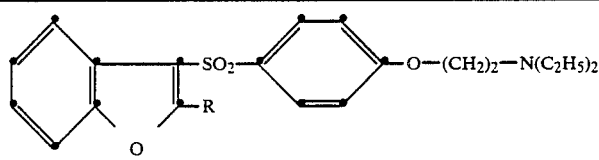

| Compound | R | % of the maximum contractional effect | | |
|---|---|---|---|---|
| | | $10^{-6}$ M | $10^{-7}$ M | $10^{-8}$ M |
| A | n-C$_4$H$_9$— | 25 | 60.3 | 84.3 |
| B | —C$_2$H$_5$ | 52.2 | 84.9 | — |

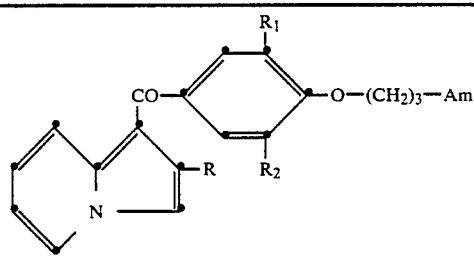

| Compound | R | $R_1$ | $R_2$ | Am | % of the maximum contractional effect | |
|---|---|---|---|---|---|---|
| | | | | | $10^{-6}$ M | $10^{-7}$ M |
| Compound C | n-$C_4H_9$ | H | H | —N(n-$C_4H_9$)$_2$ | 25.0 | 74.4 |
| Compound D | —$C_2H_5$ | $CH_3$ | $CH_3$ | —N(n-$C_4H_9$)$_2$ | 19.3 | 64.7 |
| Compound E | —$C_2H_5$ | H | H | —N(n-$C_3H_7$)$_2$ | 37.9 | 89.1 |

II. Antiadrenergic properties

The object of this test is to determine the capacity of the compounds of the invention for reducing the increase in epinephrine-induced increase in blood-pressure (anti-α effect) and the isoprenaline-induced acceleration in heart rate (anti-β effect), in dogs previously anaesthatized with pentobarbital and atropinized.

For each dog, the dose of epinephrine (between 3 and 10 μg/kg) which induced a reproducible increase in the blood-pressure of approximately $133 \times 10^2$ Pa and the dose of isoprenaline (1 to 2 μg/kg) which induced a reproducible increase in the heart rate of approximately 70 beats/min. were first determined. The does of epinephrine and of isopremaline, determined in this manner, were injected alternately every ten minutes and, after two successive reference responses had been obtained, an amount of the test compound was administered intravenously.

Anti-α effect

The percentage reduction in the hypertension induced by the test compound compared with the reference hypertension previously obtained (approximately 100 mm Hg) was recorded.

Anti-β effect

The percentage reduction in the acceleration of the heart rate induced by the test compound compared with the reference tachycardia measured previously (approximately 70 beats) was recorded.

In both cases, the results of the reduction in blood-pressure or in the heart rate have been expressed as follows:

+ for a reduction<50%
++ for a reduction≧50%
+++ for a reduction sub-total (almost complete reduction).

The following results were recorded:

| Compound | Dose (mg/kg) | anti-α effect | anti-β effect |
|---|---|---|---|
| Ex. 1 | 0.13 | +++ | ++ |
| Ex. 5 | 11.2 | ++ | ++ |
| Ex. 9 | 10.1 | +++ | ++ |
| Ex. 10 | 4.9 | + | ++ |
| Ex. 11 | 5.89 | ++ | ++ |
| Ex. 12 | 0.1 | +++ | + |
| Ex. 13 | 1.3 | +++ | + |
| Ex. 14 | 0.6 | +++ | ++ |
| Ex. 15 | 1.2 | +++ | ++ |
| Ex. 16 | 0.12 | ++ | + |
| Ex. 17 | 0.13 | +++ | ++ |
| Ex. 18 | 0.52 | ++ | + |
| Ex. 19 | 3 | +++ | ++ |
| Ex. 20 | 1.2 | +++ | + |
| Ex. 21 | 1.3 | +++ | + |
| Ex. 22 | 0.13 | +++ | + |
| Ex. 23 | 3 | +++ | ++ |
| Ex. 60 | 0.12 | +++ | +++ |

By way of comparison, the known compounds showed the following anti-adrenergic effects:

| Compound | Dose (mg/kg) | anti-α effect | anti-β effect |
|---|---|---|---|
| Compound A | 10 | + | 0 |
| Compound B | 10 | +++ | + |
| Compound C | 10 | + | 0 |
| Compound D | 10 | + | + |
| Compound E | 10 | + | ++ |
| Compound F* | 10 | − | 0 |

*2-ethyl-1-{4-[3-(di-n-butylamino-propyloxy]benzoyl}-indolizine.

These results demonstrate that the compounds of the invention show much greater α- and β-antiadrenergic activity than those of the compounds of the prior art.

III. Toxicity

The therapeutic compositions according to the invention can be presented in any form suitable for administration in human or veterinary therapy. As regards the administration unit, this can take the form of, for example, a coated- or uncoated tablet, hard- or soft-gelatin capsule, packaged powder, suspension or syrup for oral administration, a suppository for rectal administration or a solution or suspension for parenteral administration.

The therapeutic compositions of the invention may contain, per administration unit, for example, from 50 to 500 mg as the weight of active ingredient for oral administration, from 50 to 200 mg of active ingredient for rectal administration and from 50 to 150 mg of active ingredient for parenteral administration.

Depending on the administration route chosen, the therapeutical veterinary compositions of the invention will be prepared by combining at least one of the compounds of formula (1), or a non-toxic addition salt of this compound, with a suitable excipient, it being possible for the latter to consist, for example, of at least one ingredient selected from the following substances: lactose, starches, talc, magnesium stearate, polyvinylpyrrolidone, alginic acid, colloidal silica, distilled water, benzyl alcohol or sweetening agents.

The following non-limiting examples illustrate the invention:

EXAMPLE 1

Preparation of
2-isopropyl-3-[4-{3-[N-methyl-N-(3,4-dimethoxy-β-phenethyl)
amino]propyloxy}benzenesulphonyl]indolizine oxalate
(SR 33700 A)

(a)
1-Ethoxycarbonyl-2-isopropyl-3-(4-methoxybenzenesulphonyl) indolizine

Into 114 ml of 1,2-dichloroethane were dissolved 13.4 g (0.058 mol) of 1-carboethoxy-2-isopropylindolizine and 12.7 g )0.061 mol) of 4-methoxybenzenesulphonyl chloride. The solution was stirred and cooled to 0° C. while 23 g (0.174 mol) of aluminium chloride were added by small fractions.

The addition was terminated after 30 min and the medium was allowed to return to room-temperature for 4 hours. After that, the mixture was poured onto ice and 20 ml of concentrated hydrochloric acid were added. The medium was stirred for 30 min and the organic layer was decanted and washed with 3 fractions of water. The extract was dried on sodium sulphate and isolated under vacuum to obtain 24.8 g of a black oil (theory: 23.28 g). This oil was purified on a silica column using first n-hexane/10%-ethyl acetate and then n-hexane/20%-ethyl acetate as eluents.

In this manner 3.25 g of 1-ethoxycarbonyl 2-isopropyl-3-(4-methoxybenzenesulphonyl) indolizine were obtained in a form of a white solid.

Yield: 13.95%.

M.P. 103°–104° C. (hexane/methylene chloride).

(b) 1-Carboxy-2-isopropyl-3-(4-hydroxybenzenesulphonyl) indolizine

Into 100 ml of methylene chloride and 25 ml of ethanethiol, were suspended 6.7 g (0.050 mol) of aluminum chloride. The suspension was stirred and cooled to 0° C. while 2.5 g of 1-ethoxycarbonyl-2-isopropyl-3-(4-methoxybenzenesulphonyl) indolizine in methylene chloride were added. The addition took about 15 min. The reaction medium was allowed to return to room-temperature and maintained, at this temperature, for 45 min. After pouring onto ice, 5 ml of concentrated hydrochloric acid were added while stirring and the medium was extracted with 2 fractions of ethyl ether. The ethereal extracts were collected and washed with 3 fractions of 30 ml of a 10%-aqueous solution of sodium carbonate. The aqueous phase was acidified and a precipitate was observed.

In this manner 1 g of crude 1-carboxy-2 isopropyl-3-(4-hydroxybenzenesulphonyl) indolizine was obtained in the form of a beige solid.

Yield: 44.6%.

(c) 2-Isopropyl-3-(4-hydroxybenzenesulphonyl) indolizine

For 2 min, 1 g ($2.78 \times 10^{-3}$ mol) of 1-carboxy-2-isopropyl-3-(4-hydroxybenzenesulphonyl) indolizine was heated at 200° C. The black residue so obtained was taken up in methylene chloride and a slight precipitate was eliminated by filtration, the filtrate was evaporated to provide 0.8 g of a brown oil (theory: 0.877 g). This oil was purified on a silica column using a methylene chloride/ethyl acetate 95/5 mixture as eluent and 0.6 g of a green oil was isolated.

In this manner 2-isopropyl-3-(4-hydroxybenzenesulphonyl) indolizine was obtained.

Yield: 68.4%.

Purity: 97.5%.

(d) 2-Isopropyl-3-[4-{3-[N-methyl-N-(3,4-dimethoxy-β-phenethyl)amino]propyloxy}benzenesulphonyl]indolizine oxalate At room-temperature, 0.510 g ($1.57 \times 10^{-3}$ mol) of 2-isopropyl-3-(4-hydroxybenzenesulphonyl) indolizine, 0.5 g of potassium carbonate and 5 ml of dimethylsulphoxide were stirred for 30 min. To this mixture 0.524 g ($1.45 \times 10^{-3}$ mol) of 1-chloro-3-[N-methyl-N-(3,4-dimethoxy-β-phenethyl)amino]propane acid oxalate was added. The stirring was maintained for 16 h at room-temperature then for 2 h at 50° C. The dimethylsulphoxide was eliminated under vacuum and the residue was taken up in water. The medium was then twice extracted with ethyl acetate. After that the extracts were twice washed with water and dried on sodium sulphate. After filtration, the filtrate was evaporated under vacuum to obtain 0.845 g of an amber-coloured oil. This oil was purified on a silica column using as eluents, ethyl acetate containing 5%, then 10%, then 20%-methanol to provide 0.583 g of desired product in free base form (yield: 73% purity: 99.4%.).

The oxalate was formed using 0.530 g of base so obtained and an ethereal solution of oxalic acid. The oxalate was recrystallized from ethyl acetate/methanol/ethyl ether.

In this manner 0.473 g of 2-isopropyl-3-[4-{3-[N-methyl-N-(3,4-dimethoxy-β-phenethyl)amino]propyloxy}benzenesulphonyl]indolizine oxalate was obtained in the form of a white solid.

M.P.: 135°–137° C.

EXAMPLE 2

Preparation of 4-{4-[3-(di-n-butylamino)propyloxy]phenylthio}pyridine dioxalate (SR 33683 A)

(a) 4-(4-Hydroxyl-phenylthio)pyridine

A mixture of 0.0386 mol of 4-(4-methoxyl-phenylthio)pyridine hydrochloride in 100 ml of 47%-hydrobromic acid was heated to boiling for 6 hours. The hydrobromic acid in excess was then distilled off using a rotatory evaporator and the residue was taken up in water. The solution was twice washed with ethyl ether and neutralized with a sodium hydroxide aqueous solution. The precipitate which formed was filtered out, washed with water and dried under vacuum at the temperature of 60° C.

In this manner 4-(4-hydroxy-phenylthio) pyridine was obtained in a yield of 96%.

M.P.: 240° C. (heptane/isopropanol 6/4).

(b) 4-{4-[3-(Di-n-butylamino) propyloxy]phenylthio}pyridine dioxalte

A solution of 0.014 mol of 4-(4-hydroxy-phenylthio) pyridine and 3 g of finely crushed anhydrous potassium carbonate in 50 ml of dimethylsulphoxide was placed under stirring for 30 min. To this medium 0.016 mol of 1-chloro-3-(di-n-butylamino) propane was added and the stirring was maintained at room-temperature for 24 hours. The reaction medium was poured into water and extracted with ethyl ether. The organic phase was washed with water, dried no sodium sulphate and filtered. After the solvent was evaporated off, an oil was provided which was purified by chromatography on a silica column (eluent: methanol). The required compound in free base form so obtained was then transformed into an oxalate by adding an ethereal solution of oxalic acid.

In this manner 4-{4-[3-(di-n-butylamino) propyloxy]phenylthio}pyridine dioxalate was obtained in a yield of 80%.

M.P.: 153° C. (ethanol)

Using the same procedure as that described above, 4-[4-{3-[N-methyl-N-(3,4-dimethoxy-β-phenethyl)amino]propyloxy}phenylthio]pyridine oxalate (SR 33682A) (Example 3) was obtained.

M.P.: 150° C. (ethanol).

EXAMPLE 4

Preparation of
2-{4-[3-(di-n-butylamino)proyloxbenzenesulphonyl} pyridine oxalate (SR 33692 A)

(a) 2-(4-Methoxyl-benzenesulphonyl)pyridine

Into 200 ml of dichloromethane was dissolved 0.052 mol of 2-[(4-methoxy phenyl) thio]pyridine hydrochloride. To this solution, previously cooled to 0° C., a solution of 0.156 mol of 3-chloro-perbenzoic acid in 200 ml of dichloromethane was added drop-by-drop and under stirring. The reaction medium was still maintained under stirring for 15 min at 0° C. and then the temperature was brought to 25° C. The mixture was washed with an aqueous solution of sodium carbonate then with water. The organic phase was dried on anhydrous sodium sulphate, filtered and distilled using a rotatory evaporator. The residue to obtained was purified by chromatography on a silica column using a 1,2-dichloroethane/ethyl acetate 95/5 mixture as eluent.

In this manner 2-(4-methoxy-benzenesulphonyl)pyridine was obtained in a yield of 78%.

M.P.: 112° C. (isopropanol).

Using the same procedure as that described above 4-(4-methoxy-benzenesulphonyl)pyridine was prepared.

M.P.: 104° C. (heptane).

(b) 2-(4-Hydroxy-benzenesulphonyl)pyridine

A mixture of 0.028 mol of 2-(4-methoxy-benzenesulphonyl)pyridine in 70 ml of 47%-hydrobromic acid was heated to reflux for 6 hours. After this period of time, the hydrobromic acid n excess was distilled off. The residue so obtained was taken up in water, washed with ethyl ether, treated with active charcoal and filtered. The aqueous solution was then neutralized with a sodium hydroxide solution and the precipitate which formed, was filtered out and washed with water. The desired product was dried under vacuum at 60° C. and recrystallized from a heptane/isopropanol 8/2 mixture.

In this manner 2-(4-hydroxy-benzenesulphonyl)pyridine was obtained in a yield of 88%.

M.P.: 148° C.

Using the same method as that described above, 4-(4-hydroxy-benzenesulphonyl)pyridine was prepared.

M.P.: 215° C. (heptane/isopropanol 7/3).

(c) 2-{4-[3-(di-n-butylamino) propyloxy]benzenesulphonyl}pyridine oxalate

To a solution of 0.0085 mol of 2-(4-hydroxy-benzenesulphonyl)pyridine in 50 ml of dimethylsulphoxide, were added 3 g of finely crushed anhydrous potassium carbonate. The mixture was then maintained under stirring for 30 min and 0.015 mol of 1-chloro-3-(di-n-butylamino)propane was added. Stirring was still maintained for 24 hours and the reaction mixture was then poured into water and extracted with ethyl ether. The organic layer was washed with water, dried on sodium sulphate and filtered. After the filtrate was evaporated, the desired product so obtained was purified by chromatography on a silica column using methanol as eluent. The pure base so obtained was then transformed into an oxalate by addition of oxalic acid in ethyl ether.

In this manner 2-{4-[3-(di-n-butylamino)propyloxy]-benzenesulphonyl}pyridine oxalate was obtained in a yield of 50%.

M.P.: 70° C. (ethyl acetate).

Using the same method as that described above, the following compounds were prepared:

2-[4-{3-[N-methyl-N-(3,4-dimethoxy-β-phenethyl)amino]propyloxy}benzenesulphonyl]pyridine oxalate (SR 33691 A) (Example 5)

M.P.: 161.9° C. (ethanol)

4-{4-[3-(di-n-butylamino)propyloxy]benzenesulphonyl} pyridine dioxalate (SR 33685 A) (Example 6)

M.P.: 122° C. (ethyl acetate/ethanol 1/1)

4-[4-{3-[N-methyl-N-(3,4-dimethoxyl-β-phenethyl)amino[propyloxy}benzenesulphonyl]pyridine oxalate (SR 33680 A) (Example 7)

M.P.: 160° C. (ethanol).

EXAMPLE 8

Preparation of
2-{4-[3-(tertiobutylamino)propyloxy]benzenesulphonyl}pyridine oxalate (SR 33693 A)

To a solution of 0.0042 mol of 2-(4-hydroxy-benzenesulphonyl)pyridine in 25 ml of dimethylsulphoxide, was added 1.5 g of finely crushed anhydrous potassium carbonate. The mixture was stirred for 30 min and 0.0075 mol of 1-chloro-3-(N-BOC-tertiobutylamino)-propane was added. Stirring was maintained for 24 hours and the reaction mixture was then poured into water. After extraction with ethyl ether the organic phase was washed with water, dried on sodium sulphate, filtered and evaporated to dryness. The oily residue so obtained was stirred at the temperature of 185° C. for 20 min and the reaction medium was taken up in water. The mixture was made alkaline with an aqueous solution of sodium hydroxide and extracted with ethyl ether. The etheral solution was washed with water, dried on sodium sulphate and filtered. After the solvent was eliminated, a crude product was obtained which was purified by chromatography on a silica column using methanol as eluent. The base so purified was then transformed into an oxalate by adding an etheral solution of oxalic acid.

In this manner 2-{4-[3-(tertiobutylamino)propyloxy]-benzenesulphonyl}pyridine oxalate was obtained in a yield of 23%.

M.P.: 147° C.

EXAMPLE 9

Preparation of
4-{3-[N-methyl-N-(3,4-dimethoxyl-β-phenethyl)amino[propyloxy}benzenesulphonylbenzene hydrochloride (SR 33652 A)

(a) (4-Hydroxybenzenesulphonyl)benzene

To a solution of 0.05 mol of (4-methoxybenzenesulphonyl)benzene in 150 ml of anhydrous benzene, was added 0.02 mol of aluminium chloride and the reaction medium was maintained for about 15 hours under stirring at room-temperature. After this period of time, the mixture was poured onto crushed ice. The organic phase was collected, dried on sodium sulphate and evaporated to dryness.

In this manner (4-hydroxybenzenesulphonyl) benzene was obtained in a yield of 68%.

M.P.: 135° C.

(b) 4-{3-[N-Methyl-N-(3,4-dimethoxy-β-phenethyl)amino[propyloxy}benzenesulphonylbenzene hydrochloride To a solution of 0.0147 mol of (4-hydroxybenzenesulphonyl)benzene in 25 ml of dimethylsulphoxide, was added 0.0294 mol of potassium carbonate and 0.0147 mol of 1-chloro-3-[N-methyl-N-(3,4-dimethoxy-β-phenethyl)amino]propane. The mixture was maintained under stirring for 24 hours at room-temperature and 60 ml of water were added. After extraction with ethyl ether, the organic phase was dried and evaporated to dryness to obtain an oily product. The hydrochloride as formed by adding hydrogen chloride in ethyl ether to an ethereal solution of the base so provided.

In this manner, 4-{3-[3-methyl-N-(3,4-dimethoxy-β-phenethyl)amino]propyloxy}benzenesulphonylbenzene hydrochloride was obtained in a yield of 30%.

M.P.: 114° C. (ethanol).

Using the same procedure as that described above, 4-[3-(di-n-butylamino) propyloxy]benzenesulphonylbenzene oxalate was obtained (SR 31810 A). (Example 10)

Yield: 48%.

M.P.: 78°-81° C. (isopropanol).

EXAMPLE 11

Preparation of 2-n-butyl-1-{4-[3-(di-n-butylamino)propyloxy]benzenesulphony}benzimidazole acid oxalate (SR 33631A)

(a) 2-n-Butyl-1-(4-bromopropoxy-benzenesulphonyl)benzimidazole

A solution of 0.0035 mol of 4-bromopropoxy-benzimidazole, 0.0035 mol of 2-n-butyl-benzimidazole and 0.0035 mol of triethylamine in 15 ml of dioxan was maintained for 7-8 hours under stirring and at room-temperature. The solvent was eliminated under vacuum to obtain a residue which was purified by chromatography on a silica column (eluent: dichloromethane/ethyl acetate 9/1).

In this manner 2-n-butyl-1-(4-bromopropoxy-benzenesulphonyl)benzimidazole was obtained and was used as such.

Yield: 50%.

(b) 2-n-Butyl-1-{4-[3-(di-n-butylamino) propyloxy]benzenesulphonyl}benzimidazole acid oxalate To a solution of 0.0017 mol of 2-n-butyl-1-(4-bromopropoxy-benzenesulphonyl) benzimidazole in 15 ml of dimethylsulphoxide was added 0.0034 mol of n-butylamine. The reaction medium was allowed to stand for 17 hours at room-temperature and then poured into 50 ml of water. After extraction, the ethereal phase was dried and evaporated to dryness. The residue so obtained was purified by chromatography on a silica column (eluent: dichloromethane/ethyl acetate) to obtain an oil which was the desired product in the form of the free base (yield: 50 %). The oxalate of the base so provided was formed by dissolving the base in question into ethyl ether and adding an ethereal solution of oxalic acid.

In this manner 2-n-butyl-1-{4-[3-(di-n-butylamino) propyloxy]benzenesulphonyl}benzimidazole acid oxalate was obtained after recrystallization from ethanol.

EXAMPLE 12

Preparation of 2-isopropyl-3-[4-{3-[N-methyl-N-(3,4-dimethoxy-β-phenethyl amino]propyloxy}benzenesulphonyl benzofuran oxalate (SR 33670 A)

A mixture of 0.0021 mol of 2-isopropyl-3-(4-hydroxybenzenesulphonyl) benzofuran, 0.002 mol of 1-chloro-3-[N-methyl-N-(3,4-dimethoxy-β-phenethyl)amino]propane and 0.0002 mol of potassium carbonate in 2 ml of N,N-dimethylformamide was stirred at 100° C. for 1 hour. The medium was then poured into water and distilled in the presence of ethyl acetate. After that the mixture was dried on sodium sulphate, filtered and concentrated. The residue was taken up in ethyl acetate and the solution was purified by chromatography on a silica column using methanol as eluent. The oily product so obtained in free base form was taken up in ethyl acetate and one equivalent of oxalic acid in ethyl ether was added. The precipitate so formed was filtered out and recrystallized.

In this manner 2-isopropyl-3-[4-{3-[N-methyl-N-(3,4-dimethoxy-β-phenethyl)amino]propyloxy}benzenesulphonyl]benzofuran oxalate was obtained in a yield of 90%.

M.P.: 151°-158° C. (methanol/ethyl acetate).

Using the same method as that described above, the following compounds were prepared:

Compounds 2-n-Propyl-3-[4-{3-[N-methyl-N-(3,4-dimethoxy-β-phenethyl)amino]propyloxy}benzenesulphonyl]benzofuran oxalate (SR 33689 A) (Example 13). M.P.: 143°-144° C. (methanol/ethyl acetate)

2-n-Propyl-3-[4-{3-[N.methyl-N-(3,4-dimethoxy-β-phenethyl)amino]propyloxy}benzenesulphonyl]benzothiophene hemioxalate (SR 33688A) (Example 14).

M.P.: 148°-149° C. (methanol/ethyl acetate).

EXAMPLE 15

Preparation of 2-n-butyl-3-[4-{3-[N-methyl-N-(3,4-dimethoxy-B-phenethyl) amino]propyloxy)}benzenesulphonyl]benzofuran hydrochloride (SR 33646A)

(a) 2-n-Butyl-3-[4-(3-bromopropyloxy) benzenesulphonyl]benzofuran

To a solution of 0.02 mol of 2-n-butyl-3-(4-hydroxybenzenesulphonyl)-benzofuran in 150 ml of dimethylsulphoxide, was added 0.06 mol of finely crushed anhydrous potassium carbonate. The mixture was stirred for 1 hour. After that 0.1 mol of 1,3-dibromo-propane was added and the reaction medium was heated to 50° C. for 6 hours. After the reaction was terminated, the mixture was filtered and evaporated to dryness under vacuum. The residue so obtained was then taken up in dichloroethane, washed with water, then with a dilute solution of sodium hydroxide and finally with water. The organic phase was evaporated to dryness under vacuum to obtain a residual oil which was purified by chromatography on a silica column (eluent: hexane/ethyl acetate 9/1).

In this manner, 2-n-butyl-3-[4-(3-bromopropyloxy) benzenesulphonyl]benzofuran was obtained in a yield of 43%.

(b)
2-n-Butyl-3-[4-{3-[N-methyl-N-(3,4-dimethoxy-β-phenethyl)amino]propyloxy}benzenesulphonyl]benzofuran hydrochloride A mixture of 0.0086 mol of 2-n-butyl-3-[4-(3-bromopropyloxy) benzenesulphonyl]benzofuran, 4 g of anhydrous potassium carbonate and 0.015 mol of N-methyl-3,4-dimethoxy-β-phenethylamine in 50 ml of dimethylsulphoxide was maintained under stirring for 24 hours. The reaction medium was poured into water and extracted with ethyl ether. The organic solution was washed with water, dried on sodium sulphate, filtered and evaporated to dryness under vacuum. The oily residue was purified by chromatography on a silica column using, as eluent, a dichlorethane/methanol 9/1 mixture. The hydrochloride of the base so provided was formed by adding an ethereal solution of hydrogen chloride.

In this manner, 2-n-butyl-3-[4-{3-[N-methyl-N-(3,4-dimethoxy-β-phenethyl)amino]propyloxy}benzenesulphonyl]benzofuran hydrochloride was obtained in a yield of 38%. M.P.: 60° C. (diisopropyl ether).

EXAMPLE 16

Preparation of 2-isopropyl-3-{4-[3-(di-n-butylamino) propyloxy]benzenesulphonyl}pyrazolo[1,5-a]pyridine oxalate (SR 33684A)

(a)
2-Isopropyl-3-(4-methoxybenzenesulphonyl)-pyrazolo[1,5-a]pyridine

A solution of 0.03 mol of 2-isopropyl-pyrazolo[1,5-a]pyridine and 0.03 mol of 4-methoxybenzenesulphonyl chloride in 60 ml of dichloroethane was cooled to −24° C. After that 0.068 mol of aluminium chloride was added in one fraction and the reaction medium was allowed to return to room temperature for 3 hours. The mixture was then poured into ice water and distilled in the presence of ethyl acetate. After drying on sodium sulphate, the medium was filtered and concentrated. The solid so obtained was then recrystallized from an ethyl acetate/hexane mixture to provide a product in the form of a white crystalline solid.

In this manner, 0.018 mol of 2-isopropyl-3-(4-methoxybenzenesulphonyl) pyrazolo[1,5-a]pyridine was obtained.
Yield: 60%.

M.P.: 138°–139° C.

(b)
2-Isopropyl-3-(4-hydroxybenzenesulphonyl)-pyrazolo[1,5-a]pyridine

A mixture of 0.012 mol of 2-isopropyl-3-(4-methoxybenzenesulphonyl) pyrazolo[1,5-a]pyridine and 0.054 mol of pyridine hydrochloride was heated at 220° C. for 1 hour. Water was then added and the mixture was distilled in the presence of ethyl acetate. The medium was dried on sodium sulphate, filtered and concentrated. The solid so obtained was then recrystallized from isopropyl ether to provide a white crystalline product.

In this manner, 0.012 mol of 2-isopropyl-3-(4-hydroxybenzenesulphonyl) pyrazolo[1,5-a]pyridine was obtained.
Yield: 99%.
M.P.: 146.2° C.

2-Isopropyl-3-{4-[3-(di-n-butylamino)propyloxy]benzenesulphonyl)}pyrazolo[1,5-a]pyridine oxalate A mixture of 0.003 mol of 2-isopropyl-3-(4-hydroxybenzenesulphonyl) pyrazolo[1,5-a]pyridine, 0.003 mol of 1-chloro-3-(di-n-butylamino)propane and 0.004 mol of potassium carbonate in 6 ml of N,N-dimethylformamide was stirred for 40 min. at 100° C. The reaction medium was then poured into water and distilled in the presence of ethyl acetate. After drying on sodium sulphate, the mixture was filtered and concentrated. The residue was then purified on a silica column using an ethyl acetate/hexane 3/7 mixture as eluent. The base so obtained, in oily form, was then treated with an ethereal solution of one equivalent of oxalic acid and the precipitate which formed was filtered out and recrystallized from an ethyl ether/isopropanol mixture.

In this manner, 0.0028 mol of 2-isopropyl-3-{4-[3-(di-n-butylamino) propyloxy]benzenesulphonyl)} pyrazolo[1,5-a]pyridine oxalate was obtained. Yield: 92%. M.P.: 72° C.

Using the same procedure as that described above, 2-isopropyl-3-[4-{3-[N-methyl-N-(3,4-dimethoxy-β-phenethyl)amino]propyloxy}benzenesulphonyl]-pyrazolo[1,5-a]pyridine oxalate was obtained (SR 33679A)(Example:7). M.P.: 144°–47° C. (isopropanol).

EXAMPLE 18

Preparation of
2-isopropyl-3-{4-[3-(tertiobutylamino)propyloxy]benzenesulphonyl} pyrazolo[&,5-a]pyridine oxalate (SR 33686A)

(a)
2-Isopropyl-3-[4-(3-bromopropyloxy)benzenesulphonyl]pyrazolo[1,5-a]pyridine

A mixture of 0.003 mol of 2-isopropyl-3-(4-hydroxybenzenesulphonyl) pyrazolo[1,5-a]pyridine, 0.064 mol of 1,3-dibromopropane and 0.004 mol of potassium carbonate in 6 ml of N,N-dimethylformamide was stirred at 100° C. for one hour. The medium was then poured into water and distilled in the presence of ethyl acetate. After drying on sodium sulphate, the mixture was filtered and concentrated to obtain a residue which was purified on a silica column using an ethyl acetate/hexane 1/1 mixture.

In this manner, 0.0021 mol of 2-isopropyl-3-[4-(3-bromopropyloxy) benzenesulphonyl]pyrazolo[1,5-a]pyridine was obtained in the form of a viscous oil. Yield: 69%.

2-Isopropyl-3-{4-[3-(tertiobutylamino)propyloxy]benzenesulphonyl)}pyrazolo[1,5-a]pyridine oxalate In a flask, a solution of 0.002 mol of 2-isopropyl-3-[4-(bromopropyloxy)benzenesulphonyl]pyrazolo[1,5-a]pyridine and 0.008 mol of tertiobutylamine in 4 ml of N,N-dimethylsulphoxide was stirred at room-temperature for 24 hours. The mixture was poured into water and then distilled in the presence of ethyl acetate. After drying on sodium sulphate, the medium was filtered and concentrated to obtain a base in oily form. A solution of this base in an ethyl ether/ethyl acetate mixture was then treated with one equivalent of oxalic acid and the white precipitate so obtained was recrystallized from an ethyl ether/isopropanol mixture.

In this manner, 0.002 mol of 2-isopropyl-3-{4-[3-(tertiobutylamino) propyloxy]benzenesulphonyl)} pyrazolo[1,5-a]pyridine oxalate was obtained. Yield: 99%. M.P.: 208° C.

EXAMPLE 19

Preparation of
2-isopropyl-3-[4-{3-[N-methyl-N-(3,4-dimethoxy-β-phenethyl)amino]propyloxy}benzenesulphonyl]-4,5-dihydro-furan oxalate (SR 33681A)

(a)

1-(4-Tosyloxybenzenesulphonyl)-3-methyl-butan-2-one

A mixture of 0.1 mol of sodium 4-tosyloxysulphinate and 0.1 mol of bromomethyl isopropyl ketone in 400 ml of N,N-dimethylformamide was stirred at 85° C. for 90 min. The mixture was then poured onto ice and filtered on fritted glass. The pasty residue so obtained was successively washed twice with water, once with 200 ml of ethanol and finally with ethyl ether. After drying under vacuum for 2 hours the desired product was provided after recrystallization from ethyl acetate.

In this manner, 0.074 mol of 1-(4-tosyloxybenzenesulphonyl)-3-methylbutan-2-one was obtained in the form of a white solid. Yield: 74%. M.P.: 160° C.

(b)

1-Isobutyryl-1-(4-tosyloxybenzenesulphonyl)cyclopropane

A mixture of 0.05 mol of 1-(4-tosyloxybenzenesulphonyl)-3-methylbutan-2-one, (0.05 mol) of 1,2-dibromo-ethane and 0.12 mol of potassium carbonate in 100 ml of N,N-dimethylfornamide was stirred at room-temperature for 60 hours. The reaction mixture was poured into water, acidified with dilute hydrochloric acid and extracted with ethyl acetate. After drying on sodium sulphate, the medium was filtered and concentrated. The residue so obtained was then purified by chromatography on a silica column using an ethyl acetate/hexane 3/7 mixture as eluent.

In this manner, 0.026 mol of 1-isobutyryl-1-(4-tosyloxybenzenesulphonyl)cyclopropane was obtained in a yield of 53%. M.P.: 106°–107° C.

(c)

1-Isobutyryl-1-(4-hydroxybenzenesulphonyl)cyclopropane

Into 85 ml of ethanol heated to 80° C., was dissolved 0.026 mol of 1-isobutyryl-1-(4-tosyloxybenzenesulphonyl)cyclopropane. A solution of 0.05 mol of sodium hydroxide in 30 ml of water was then added and the medium was maintained at 80° C. for 10 min. The ethanol was eliminated under reduced pressure and the residue was taken up in dilute hydrochloric acid and distilled in the presence of ethyl acetate. After drying on sodium sulphate, the medium was filtered and concentrated. The residue so obtained was then purified by chromatography on a silica column using an ethyl acetate/hexane 1/1 mixture.

In this manner, 0.016 mol of 1-isobutyryl-1-(4-hydroxybenzenesulphonyl) cyclopropane was obtained in the form of a white solid. Yield: 60%.

M.P.: 111°–112° C. (ethyl acetate).

(d)

1-Isobutyryl-1-[4-{3-[N-methyl-N-(3,4-dimethoxy-β-phenethyl)amino]propyloxy}benzenesulphonyl]cyclopropane A mixture of 0.005 mol of 1-isobutyryl-1-(4-hydroxybenzenesulphonyl) cyclopropane, 0.0048 mol of 1-chloro-3-[N-methyl-N-(3,4-dimethoxy-β-phenethyl)amino]propane and 0.005 mol of potassium carbonate in 5 ml of N,N-dimethylformamide was heated at 140° C. for 15 min. The reaction mixture was then poured into water and distilled in the presence of ethyl acetate. After drying on sodium sulphate, the medium was filtered and concentrated. The residue was then purified by chromatography on a silica column using an ethyl acetate/hexane 1/1 mixture.

In this manner, 0.0033 mol of 1-isobutyryl-1-[4-{3-[N-methyl-N-(3,4-dimethoxy-β-phenethyl)amino]propyloxy}benzenesulphonyl]cyclopropane was obtained in oily form. Yield: 66%.

(e)

2-Isopropyl-3-[4-{3-[N-methyl-N-(3,4-dimethoxy-β-phenethyl)amino]propyloxy}benzenesulphonyl]-4,5-dihydro-furan oxalate A mixture of 0.002 mol of 1-isobutyryl-1-[4-{3-[N-methyl-N-(3,4-dimethoxy-β-phenethyl)amino]propyloxy)benzenesulphonyl]cyclopropane and 0.003 mol of tricaprylylmethyl ammonium chloride was heated at 115° C. for 30 min. The reaction medium was then purified by chromatography on a silica column using an ethyl acetate/hexane 1/1 mixture to obtain a base in oily form. An ethereal solution of the base so provided was then treated with one equivalent of oxalic acid in ethyl ether.

In this manner, 0.0013 mol of 2-isopropyl-3-[4-{3-[N-methyl-N-(3,4-dimethoxy-β-phenethyl)amino]propyloxy} benzenesulphonyl]-4,5-dihydro-furan oxalate was obtained in the form of a white solid. Yield: 65%.

M.P.: 147.2° C. (methanol).

EXAMPLE 20

Preparation of
2-isopropyl-3-{4-[3-(di-n-butylamino)propyloxy]benzenesulphonyl}quinoline oxalate (SR 33695A)

(a)

2-Isopropyl-3-(4-tosyloxybenzenesulphonyl)quinoline

In a sealed tube a mixture of 0.02 mol of 2-aminobenzaldehyde and 0.02 mol of 1-(4-tosyloxybenzenesulphonyl)-3-methyl-butan-2-one was heated at 185° C. for 2 hours. The mixture was then taken up in dry ethyl ether and filtered.

M.P. of the hydrochloride: about 90° C.

(b)

2-Isopropyl-3-(4-hydroxybenzenesulphonyl)quinoline

To a solution of 0.017 mol of 2-isopropyl-3-(4-tosyloxybenzenesulphonyl) quinoline in 250 ml of ethanol, was added a solution of 0.068 mol of sodium hydroxide in 5 ml of water. The mixture was heated to reflux for 2 hours and then the solvent was eliminated. The residue so obtained was taken up in water and neutralized with acetic acid. The precipitate which formed was then filtered out, dried and recrystallized from a dichlorethane/heptane 1/1 mixture.

In this manner, 2-isopropyl-3-(4-hydroxybenzenesulphonyl) quinoline was obtained in a yield of 58%. M.P.: 185° C.

(c)

2-Isopropyl-3-{4-[3-(di-n-butylamino)propyloxy]benzenesulphonyl}quinoline oxalate To a solution of 0.005 mol of 2-isopropyl-3-(4-hydroxybenzenesulphonyl)quinoline in 25 ml of dimethylsulphoxide, was added 0.015 mol of anhydrous potassium carbonate. The mixture was stirred for 30 min. and 0.0075 mol of 1-chloro-3-(di-n-butylamino)-propane was added. The reaction medium was maintained under stirring for 24 hours. After this period of time, the mixture was poured into water and extracted with ethyl ether. The organic phase was washed with water, dried on sodium sulphate, filtered and evaporated to dryness. An oily base was so provided which was purified by chromatography on a silica column (eluent: isopropanol) and transformed into an oxalate by adding oxalic acid in ethyl ether.

In this manner 2-isopropyl-3-{4-[3-(di-n-butylamino)propyloxy]benzenesulphonyl}quinoline oxalate was obtained in a yield of 55%.

M.P.: 130° C. (ethanol).

Using the same method as that described above, 2-isopropyl-3-[4-{3- [N-methyl-N-(3,4-dimethoxy-β-phenethyl)amino]propyloxy}benzenesulphonyl]quinoline oxalate (SR 33694 A) (Example 27).

M.P.: 162° C. (ethanol).

EXAMPLE 22

Preparation of
5-[4-{3-[N-methyl-N-(3,4-dimethoxy-β-phenethyl)amino]propyloxy)}benzenesulphouyl]-6-isopropyl-pyrrolo[1,2-b]pyridazine oxalate (SR 33687A)

(a) 3-(4-Tosyloxybenzenesulphonyl)methyl-pyridazine

To a solution of 0.13 mol of 3-chloromethyl-pyridazine hydrochloride in 400 ml of dimethylsulphoxide was added 0.13 mol of sodium bicarbonate. The mixture was stirred for 30 min. and 0.195 mol of sodium 4-tosyloxybenzenesulphonate was introduced. The reaction medium was maintained under stirring for 2 hours at room-temperature then for 2 hours at 50° C. The mixture was poured into 3 l of water and the precipitate so formed was filtered, washed with water and dried under vacuum.

In this manner, 3-(4-tosyloxybenzenesulphonyl)methyl-pyridazine was obtained in a yield of 82%.

M.P.: 161° C. (ethanol).

(b)
5-(4-Tosyloxybenzenesulphonyl)-6-isopropyl-pyrrolo[1,2-b]pyridazine.

A mixture of 0.011 mol of 3-(4-tosyloxybenzenesulphonyl)methylpyridazine and 0.011 mol of 1,8-diazabicyclo[5,4,0]undec-7-ene in 40 ml of hexamethylphosphoramide was heated at 75° C. for 30 min. After that 4 g of bromomethyl isopropyl ketone were added while maintaining the same temperature for 6 hours. The mixture was poured into 200 ml of water and extracted with dichloroethane. The organic solution was washed with water, dried on sodium sulphate and filtered. The solvent was eliminated under vacuum to provide an oily residue which was purified by chromatography on a silica column (eluent: dichloroethane).

In this manner, 5-(4-tosyloxybenzenesulphonyl)-6-isopropyl-pyrrolo[1,2-b]pyridazine was obtained in crystalline form. Yield: 7%

M.P.: 149° C. (isopropanol).

(c)
5-(4-Hydroxybenzenesulphonyl)-6-isopropyl-pyrrolo[1,2-b]pyridazine.

A solution of 0.0034 mol of 5-(4-tosyloxybenzenesulphonyl)-6-isopropylpyrrolo[1,2-b]pyridazine in 75 ml of ethanol was heated to boiling and a solution of 0.0034 mol of sodium hydroxide in 3 ml of water was added. Boiling was maintained for 6 hours. The solvent was eliminated and the residue was taken up in water and neutralized with acetic acid. The precipitate so formed was taken up in dichloroethane and the solution was washed with water, dried on sodium sulphate and filtered. The solvent was finally evaporated off.

In this manner, 5-(4-hydroxybenzenesulphonyl)-6-isopropyl-pyrrolo [1,2-b]pyridazine was isolated in a yield of 75%.

(c)
5-[4-{3-[N-Methyl-N-(3,4-dimethoxy-β-phenethyl)amino]propyloxy)}benzenesulphonyl]-6-isopropyl-pyrrolo[1,2-b]pyridazine oxalate A mixture of 0.0022 mol of 5-(4-hydroxybenzenesulphonyl)-6-isopropylpyrrolo[1,2-b]pyridazine and 1.5 g of anhydrous potassium carbonate in 25 ml of dimethylsulphoxide was stirred for 30 min. After that, 0.0027 mol of 1-chloro-3-[N-methyl-N-(3,4-dimethoxy-β-phenethyl)amino]propane oxalate was added and stirring was maintained at room-temperature for 18 hours. The reaction medium was then heated at 50° C. for 5 hours, poured into water and extracted with ethyl ether. The ethereal phase was washed with water, dried on sodium sulphate and filtered. After evaporating the solvent, an oily residue was obtained which was purified by chromatography and a silica column using methanol as eluent. The oxalate was formed by adding oxalic acid in ethyl ether to an ethereal solution of the base so provided.

In this manner, 5-[4-{3-[N-methyl-N-(3,4-dimethoxy-β-phenethyl)amino]propyloxy}benzenesulphonyl]-6-isopropyl-pyrrolo[1,2-b]pyridazine oxalate was obtained in a yield of 57%.

M.P.: 88° C. (ethyl acetate/isopropanol).

EXAMPLE 23

Preparation of
2-isopropyl-3-[4-{3-[N-methyl-N-(3,4-dimethoxy-β-phenethyl) amino]propyloxy}benzenesulphonyl]furan oxalate (SR 33697 A)

(a)
2-Isopropyl-3-(4-tosyloxybenzenesulphonyl)-4,5-dihydro-furan

A mixture of 0.008 mol of 1-isobutyryl-1-(4-tosyloxybenzenesulphonyl) cyclopropane and 0.022 mol of tricaprylylmethyl ammonium chloride was heated at 130° C. for 30 min. The reaction mixture was then chromatographed on a silica column using an ethyl acetate/hexane 25/75 mixture as eluent.

In this manner, 0.0145 mol of 2-isopropyl-3-(4-tosyloxybenzenesulphonyl)-4,5-dihydro-furan was obtained in the form of a white solid. Yield: 66%.

M.P.: 103° C. (ethyl acetate/hexane).

(b) 2-Isopropyl-3-(4-tosyloxybenzenesulphonyl) furan

A mixture of 0.035 mol of 2-isopropyl-3-(4-tosyloxybenzenesulphonyl)-4,5-dihydro-furan, 1 mol of manganese dioxide and 3 Å-molecular screen in powder (previously dried at 140° C. under 0.01 mm Hg for 5 h) in 400 ml of dry ethyl ether was stirred for 66 hours at room-temperature. The mixture was then filtered and the solid was rinsed with dichloromethane. After concentration the medium was chromatographed on a silica column using an ethyl acetate/hexane 2/8 mixture.

In this manner, 0.009 mol of 2-isopropyl-3-(4-tosyloxybenzenesulphonyl)furan was obtained in a yield of 25%.

M.P.: 94° C. (ethyl acetate/hexane).

(c) 2-Isopropyl-3-(4-hydroxybenzenesulphonyl)furan

To a solution of 0.008 mol of 2-isopropyl-3-(4-tosyloxybenzenesulphonyl)furan in 1.8 ml of ethanol were added 18 ml of 1N-sodium hydroxide. The milky solution was stirred under reflux to complete dissolution (2 minutes) and the reaction medium was cooled and neutralized with dilute hydrochloric acid. After that, the mixture was distilled in the presence of ethyl acetate. The organic phase was dried on sodium sulphate, filtered and concentrated. The residue so obtained was then purified on a silica column and eluted using an ethyl acetate/hexane 4/6 mixture.

In this manner, 0.0073 mol of 2-isopropyl-3-(4-hydroxybenzenesulphonyl) furan was obtained in a yield of 91%.

M.P.: 131° C. (ethyl acetate/hexane).

(d)
2-Isopropyl-3-[4-{3-[N-methyl-N-(3,4-dimethoxy-β-phenethyl)amino]propyloxy} benzenesulphonyl]furan oxalate A mixture of 0.003 mol of 2-isopropyl-3-(4-hydroxybenzenesulphonyl) furan, 0.003 mol of 1-chloro-3-[N-methyl-N-(3,4-dimethoxy-β-phenethyl)amino]propane and $3.23 \times 10^{-3}$ mols of crushed potassium carbonate in 3 ml of N,N-dimethylformamide was heated at 100° C. for 30 minutes. The mixture was then poured into water and distilled in the presence of ethyl acetate. After drying on sodium sulphate, the medium was filtered and concentrated. The residue so obtained was then purified by chromatography on a silica column using methanol as eluent. After that, the base so provided was transformed into oxalate by adding oxalic acid in ethyl ether.

In this manner, 0.00288 mol of 2-isopropyl-3-[4-{3-[N-methyl-N-(3,4-dimethoxy-β-phenethyl)amino]-propyloxy}benzenesulphonyl]furan oxalate was obtained.

Yield: 96%.

M.P.: 102° C. (chloroform/ethyl acetate).

Using the same method as described above, 2-isopropyl-3-{4-[3-(din-butylamino)propyloxy]benzenesulphonyl} furan oxalate (SR 33701 A) (Example 24) was obtained in a yield of 92%.

M.P.: 98° C. (ethanol/ethyl ether).

EXAMPLE 25

Preparation of
2-isopropyl-3-{4-[3-(tert-butylamino)propyloxyben-zenesulphonyl}furan oxalate (SR 33702 A)

(a)
2-Isopropyl-3-[4-(3-bromopropyloxy)benzenesul-phonyl]furan

A mixture of 0.003 mol of 2-isopropyl-3-(4-hydroxyl-benzenesulphonyl) furan, 0.06 mol of 1,3-dibromopropane and 0.005 mol of crushed potassium carbonate in 8 ml of N,N-dimethylformamide was heated at 100° C. for 1 hour. The mixture was poured into water and distilled in the presence of ethyl acetate. After drying on sodium sulphate, the medium was filtered and concentrated. The residue so obtained was then purified by chromatography on a silica column using an ethyl acetate/hexane 2/8 mixture.

In this manner, 0.00282 mol of 2-isopropyl-3-[4-(3-bromopropyloxy) benzenesulphonyl]furan was obtained in oily form. Yield: 94%.

(b)
2-Isopropyl-3-{4-[3-(tert-butylamino)propyloxy]ben-zenesulphonyl}furan oxalate A mixture of 0.00282 mol of 2-isopropyl-3-[4-(3-bromopropyloxy)benzenesulphonyl]furan and 0.013 mol of tert-butylamine in 7 ml of dimethylsulphoxide was stirred at room-temperature for 24 hours. After that, the mixture was poured into water, distilled in the presence of ethyl acetate, dried on sodium sulphate, filtered and concentrated. The residue so obtained was purified on a silica column using a methanol/ethyl acetate 2/8 mixture as eluent. The oily base so provided was then treated with an ethereal solution of oxalic acid and the precipitate was recrystallized from ethanol.

In this manner, 0.0023 mol of 2-isopropyl-3-{4-[3-(tert-butylamino) Propyloxy]benzenesulphonyl}furan oxalate was obtained in a yield of 82%.

M.P.: 143.6° C.

EXAMPLE 26

Preparation of
4-[4-{3-[N-methyl-N-(3,4-dimethoxy-β-phenethyl-)amino]propyloxy}phenylthio]cinnoline oxalate (SR 33699A)

(a) 4-(4-Methoxyphenylthio)cinnoline

To a solution of sodium methylate prepared from 0.7 g (0.03 at.g.) of sodium in 25 ml of methanol, there were added 4.2 g (0.03 mol) of 4-methoxyphenylthiol. The methanol in excess was eliminated using a rotatory evaporator and the sodium salt so obtained was dried under high vacuum and then dissolved into 100 ml of N,N-dimethylformamide. After that, 4.38 g (0.03 mol) of 4-chlorocinnoline were added. The medium was stirred at room-temperature for 24 hours and then poured into water. After filtration, the product was washed on the filter with water and then dried under vacuum at the temperature of 60° C.

In this manner 6.4 g of 4-(4-methoxyphenylthio)cinnoline were obtained in a yield of 80%.

M.P.: 163° C. (7/3 isopropanol/heptane)

Using the same procedure as that described above but from 3-bromocinnoline there was obtained 3-(4-methoxyphenylthio)cinnoline Yield: 74.6%

M.P.: 108° C. (isopropanol)

(b) 4-(4-hydroxyphenylthio)cinnoline

To a solution of 3.6 g (0.0134 mol) of 4-(4-methoxyphenylthio)cinnoline, there were added 30 ml of 47%-hydrobromic acid. The mixture was stirred and heated at 125° C. for 4 hours. The hydrobromic acid in excess was then eliminated with a rotatory evaporator and the residue obtained was taken up with water. The solution was neutralized with sodium bicarbonate and filtered. The product so isolated was washed on the filter with water and dried under vacuum at the temperature of 60° C.

In this manner, 2.9 g of 4-(4-hydroxyphenpylthio)cinnoline were obtained after recrystallization from a 7/3 isopropanol/heptane mixture. Yield: 85%

M.P.: 238° C.

Using the same procedure described above but from 3-(4-methoxyphenylthio)cinnoline, there was obtained 3-(4-hydroxyphenylthio)cinnoline in a yield of 90%.

(c) 4-[4-{3-[N-methyl-N-(3,4-dimethoxy-β-phenethyl)amino]propyloxy}phenylthio]cinnoline oxalate.

A mixture of 2.5 g (0.01 mol) of 4-(4-hydroxyphenylthio)cinnoline and 7 g of crushed anhydrous potassium carbonate in 50 ml of dimethylsulphoxide was stirred for 30 min. After that 4.4 g (0.012 mol) of 1-chloro-3-[N-methyl-N-(3,4-dimethoxy-β-phenethyl)amino]propane oxalate were added while stirring was maintained for 24 hours at room-temperature. The medium was poured into water and extracted with ethyl ether. The ethereal solution was washed with water, dried on anhydrous sodium sulphate and filtered. The ethyl ether was eliminated with a rotatory evaporator to obtain 5.3 g of an oil which was purified by chromatography on a silica column using methanol as eluent. The base so provided (4.7 g) was then transformed into an oxalate in ethyl ether medium and the salt was recrystallized from ethanol.

In this manner 4.1 g of 4-[4-{3-[N-methyl-N-(3,4-dimethoxy-8-phenethyl) amino]propyloxy}phenylthio]cinnoline oxalate were obtained.

Yield: 70.8%

M.P.: 138° and 160° C.

Using the same procedure as that described above but from 3-(4-hydroxyphenylthio)cinnoline there was prepared 3-[4-{3-[N-methyl-N-(3,4dimethoxy-β-phenethyl)amino]propyloxy{phenylthio]cinnoline oxalate (Example 27) (SR 33704 A)

Yield: 67.6%

M.P.: 166° C.

EXAMPLE 28

Preparation of 3-[4-{3-[N-methyl-N-(3,4-dimethoxy-β-phenethyl)amino]propyloxy{benzenesulphonyl]cinnoline oxalate (SR 33703A)

(a) 3-(4-Hydroxybenzenesulphonyl)cinnoline

A mixture of 2.1 g (0.01 mol) of 3-bromocinnoline, 6.6 g (0.02 mol) of sodium 4-tosyloxybenzenesulphinate and 50 ml of dimethylsulphoxide was stirred and heated at 120° C. for 24 hours. The mixture was poured into water and extracted with dichloroethane. The dichloroethane solution was washed with water, dried on anhydrous sodium sulphate and filtered. The solvent was then evaporated with a rotatory evaporator to provide 2.5 g of an oily residue. The desired product was then isolated by chromatography on a silica column using dichlorethane/methanol 98/2.

In this manner, 0.45 g of 3-(4-hydroxybenzenesulphonyl)cinnoline was obtained.

Yield: 10.2%

(b) 3-[4-{3-[N-Methyl-N-(3,4-dimethoxy-β-phenethyl)amino]propyloxy}benzenesulphonyl]cinnoline oxalate.

A mixture of 0.2 g (0.0007 mol) of 3-(4-hydroxybenzenesulphonyl)cinnoline and 0.4 g of potassium carbonate in 10 ml of dimethylsulphoxide was stirred for 30 min. After that, 0.3 g (0.0008 mol) of 1-chloro-3-[N-methyl-N-(3,4-dimethoxy-β-phenethyl)amino]propane oxalate was added and the stirring was maintained for 24 hours at room-temperature. The medium was poured into water and extracted with ethyl ether. The ethereal solution was washed with water, dried on anhydrous sodium sulphate and filtered. The ethyl ether was then eliminated using a rotatory evaporator and the residue was purified by chromatography on a silica column using methanol as solvent to provide 0.100 g (30%) of a base. This base was then transformed into an oxalate in ethyl ether by adding an ethereal solution of oxalic acid and the salt so formed was recrystallized from ethanol.

In this manner, 0.100 g of 3-[4-{3-[N-methyl-N-(3,4-dimethoxy-β-phenethyl) amino]propyloxy}benzenesulphonyl]cinnoline oxalate was obtained. M.P.: 158° C.

EXAMPLE 29

Preparation of 2-isopropyl-1-[4-{3-[N-methyl-N-oxide-N-(3,4-dimethoxy-β-phenethyl)amino]propyloxy}benzenesulphonyl]indolizine acid oxalate.

A solution of 2.75 g (0.005 mol) of 2-isopropyl-1-[4-{3-[N-methyl-N-(3,4-dimethoxy-β-phenethyl)amino]propyloxy}benzenesulphonyl]indolizine in 40 ml of dichloromethane was cooled to −10° C. Under stirring, 1 g (0.005 mol) of 3-chloro-perbenzoic acid in 40 ml of dichloromethane was added to the reaction medium which was then allowed to return to room-temperature. The mixture was washed with a sodium carbonate solution and then with water. After drying on sodium sulphate and filtering, the solvent was evaporated off using a rotatory evaporator. The residue so obtained (3.1 g) was then purified by chromatography on a silica column using methanol as solvent to obtain the required N-oxide derivative in free base form. The oxalate was then formed by adding an ethereal solution of oxalic acid to a solution, of the base so provided, in tetrahydrofuran/ethyl ether.

In this manner, 2-isopropyl-1-[4-{3-[N-methyl-N-oxide-N-(3,4-dimethoxyβ-phenethyl)amino]propyloxy} benzenesulphonyl]indolizine acid oxalate was obtained. The N.M.R. spectrum was found to be correct.

EXAMPLE 30

Preparation of 1-benzyl-2-[4-{3-[N-methyl-N-(3,4-dimethoxy-8-phenethyl) amino]propyloxy}benzenesulphonyl]imidazole. (SR 33776)

(a) N-Benzylimidazole

To a solution of 24 g (1 mol) of sodium hydride in 500 ml of N,N-dimethylformamide, there was added, drop-by-drop, a solution of 68 g (1 mol) of imidazole in 150 ml of N,N-dimethylformamide. The medium was stirred for 2 hours and then 126.6 g (1 mol) of benzyl chloride were added. The solvent was eliminated and the residue was taken up with ethyl acetate and washed with water. The organic phase was dried and concentrated to provide an oil which crystallized when cold.

In this manner, N-benzylimidazole was obtained in a yield of 70%.

(b) 1-Benzyl-2-(4-methoxybenzenesulphonyl)imidazole.

To a solution of 44 g (0.28 mol) of 1-benzylimidazole in 200 ml of acetonitrile, there were added, drop-by-drop, 57.5 g (0.28 mol) of 4-methoxybenzenesulphonyl chloride dissolved into 50 ml of acetonitrile. After one hour, 41.5 ml (0.31 mol) of triethylamine were added and the medium was maintained under stirring for 12 hours. The precipitate was isolated and the solution was purified by high pressure liquid chromatography using dichloromethane as eluent.

In this manner, 1-benzyl-2-(4-methoxybenzenesulphonyl)imidazole was obtained in a yield of 5%.

(c) 1-Benzyl-2-(4-hydroxybenzenesulphonyl)imidazole.

A mixture of 2.6 g ($8 \times 10^{-3}$ mol) of 1-benzyl-2-(4-methoxybenzenesulphonyl)imidazole in 10 ml of iodohydric acid was heated for 5 hours at 170° C. The reaction medium was then poured into ice water and extracted with ethyl acetate. The organic phase was dried and concentrated and the residue obtained was purified by high pressure liquid chromatography using dichloromethane as eluent.

In this manner, 1-benzyl-2-(4-hydroxybenzenesulphonyl)imidazole was obtained in a yield of 20%.

(d) 1-Benzyl-2-[4-{3-[N-methyl-N-(3,4-dimethoxy-β-phenethyl)amino]propyloxy}benzenesulphonyl]imidazole A mixture of 0.5 g ($1.6 \times 10^{-3}$ mol) of 1-benzyl-2-(4-hydroxybenzenesulphonyl)imidazole, 0.86 g ($2.4 \times 10^{-3}$ mol) of 1-chloro-3-[N-methyl-N(3,4-dimethoxy-β-phenethyl)amino]propane oxalate and 1.1 g ($7.9 \times 10^{-3}$ mol) of potassium carbonate in 6 ml of dimethylsulphoxide was maintained at 35° C. for 3 days. The reaction medium was then poured into ice water and the oil so obtained was purified by high pressure liquid chromatography using ethyl acetate as eluent. Yield: 78%.

EXAMPLE 31

Preparation of 1-isopropyl-2-[4-{3-[N-methyl-N-(3,4-dimethoxy-β-phenethyl)amino]propyloxy}benzenesulphonyl]benzimidazole oxalate.

(a) 1-Isopropyl-2-(4-benzyloxybenzenesulphonyl)benzimidazole.

To a solution of $7.08 \times 10^{-4}$ mol of 4-benzyloxybenzenesulphonyl chloride in 10 ml of acetonitrile cooled to 0° C., there was added $7.08 \times 10^{-4}$ mol of 1-isopropylbenzimidazole prepared in N,N-dimethylformamide from benzimidazole and isopropyl bromide in the presence of sodium hydride. After that one equivalent of triethylamine was added. The medium was stirred at room-temperature for 12 hours and the acetonitrile was then evaporated off. The residue so obtained was then taken up with water and extracted several times with dichloromethane. The organic extracts were collected, dried and evaporated. The residue so provided was purified by chromatography on a silica column using a dichloromethane/ethyl acetate 99/1 mixture as eluent.

In this manner, 1-isopropyl-2-(4-benzyloxybenzenesulphonyl)benzimidazole was obtained in a yield of 52%.

M.P.: 94°–96° C.

(b) 1-Isopropyl-2-(4-hydroxybenzenesulphonyl)benzimidazole.

To 20 ml of ethanol, there were added $2.95 \times 10^{-4}$ mol of 1-isopropyl-2-(4-benzyloxybenzenesulphonyl)benzimidazole and 0.015 g of 10%-palladium charcoal and the mixture so obtained was maintained under hydrogen atmosphere. When the required quantity of hydrogen was absorbed namely after about 2 hours, the catalyst was filtered out and washed with ethanol. The alcoholic extracts were collected and evaporated under vacuum.

In this manner 1-isopropyl-2-(4-hydroxybenzenesulphonyl)benzimidazole was obtained in the form of a white crystalline product.

Yield: 64%

M.P.: 198° C.

(c) 1-Isopropyl-2-[4-{3-[N-methyl-N-(3,4-dimethoxy-β-phenethyl)amino]propyloxy}benzenesulphonyl]benzimidazole oxalate.

To a mixture of $1.42 \times 10^{-4}$ mol of 1-isopropyl-2-(4-hydroxybenzenesulphonyl)benzimidazole and 5 equivalents of potassium carbonate in 5 ml of dimethylsulphoxide, there was added 1.5 equivalent of 1-chloro-3-[N-methyl-N-(3,4-dimethoxy-β-phenethyl)amino]propane oxalate. The medium was stirred for about 15 hours at 35° C. and the residue was poured on ice and extracted with ethyl acetate. The organic phase was then dried and evaporated and the base so provided was purified by chromatography on a silica column using an ethyl acetate/methanol 95/5 mixture. The oxalate was then formed using an ethereal solution of oxalic acid.

In this manner, 1-isopropyl-2-[4-3-[N-methyl-N-(3,4-dimethoxy-β-phenethyl)amino]propyloxy}benzenesulphonyl]benzimidazole oxalate was obtained.

EXAMPLE 32

Preparation of 2-[4-{3-[N-methyl-N-(3,4-dimethoxy-β-phenethyl)amino]propyloxy}benzenesulphonyl]pyrimidine oxalate.

(a) 2-(4-Methoxybenzenesulphonyl)pyrimidine.

To $8.7 \times 10^{-2}$ mol of 50%-sodium hydride in 20 ml of N N-dimethyl there were added 12.3 g ($8.7 \times 10^{-2}$ mol) of 4-methoxyphenylthiol. After the gaseous evolution was terminated namely after about 2 hours, 10 g ($8.7 \times 10^{-2}$ mol) of 2-chloropyrimidine in 100 ml of N,N-dimethylformamide were added. The medium was stirred at room-temperature for 3 hours and the slight precipitate was filtered out. After evaporation of the solvent, the oily residue was taken up in 100 ml of water and the mixture was stirred. The product which crystallized was then filtered out and washed with water.

In this manner 2-(4-methoxybenzenesulphonyl)pyrimidine was obtained in a yield of 89%. M.P.: 72° C.

(b) 2-(4-Hydroxybenzenesulphonyl)pyrimidine.

A mixture of $4.6 \times 10^{-3}$ mol of 2-(4-methoxybenzenesulphonyl)pyrimidine and 10 ml of 47%-hydrobromic acid was heated for 1 hour at 90° C. The reaction medium was neutralized to a pH of 7 with an ammonia solution and the pasty residue was extracted with dichloromethane. The organic phase was then dried and evaporated and the residue so provided was purified by chromatography on a silica column using dichloromethane as eluent.

In this manner, 2-(4-hydroxybenzenesulphonyl)pyrimidine was obtained.

(c)
2-[4-{3-[N-methyl-N-(3,4-dimethoxy-β-dimethoxy-β-phenethyl)amino]propyloxy}benzenesulphonyl]pyrimidine oxalate.

To a mixture of $1.6 \times 10^{-3}$ mol of 2-(4-hydroxybenzenesulphonyl) pyrimidine, $2.4 \times 10^{-3}$ mol of 1-chloro-3-[N-methyl-N-(3,4-dimethoxy-β-phenethyl)amino]propane oxalate and 1.1 g of potassium carbonate was maintained at 35° C. for several hours and the residue was poured on ice and extracted with ethyl acetate. The organic phase was then dried and evaporated and the base so provided was purified by chromatography on a silica column. The oxalate was then formed using an ethereal solution of oxalic acid.

In this manner 2-[4-{3-[N-methyl-N-(3,4-dimethoxy-β-phenethyl)amino]propyloxy}benzenesulphonyl]pyrimidine oxalate was obtained.

EXAMPLE 33

Preparation of
2-[4-{3-[N-methyl-N-(3,4-dimethoxy-β-phenethyl)amino]propyloxy}benzenesulphonyl]indene oxalate (SR 33705 A)

(a) 3-Chloro-2-(4-tosyloxybenzenesulphonyl)indane

Under nitrogen atmosphere a mixture of 0.05 mol of indene of sulphonyl chloride, 0.0005 mol of cupric chloride and 0.0005 mol of triethylamine hydrochloride in 3 ml of acetonitrile was heated at 115° C. for 2 hours. The medium was then poured into methanol and the precipitate which formed was filtered and recrystallized from an ethyl acetate/chloroform mixture.

In this manner, 0.042 mol of 3-chloro-2-(4-tosyloxybenzenesulphonyl) indane was obtained in a yield of 84%. M.P.: 176° C.

(b) 2-(4-Tosyloxybenzenesulphonyl)indene.

A mixture of 0.025 mol of 3-chloro-2-(4-tosyloxybenzenesulphonyl) indane and 0.04 mol of triethylamine in 125 ml of chloroform was stirred for 4 hours at room-temperature. The medium was poured into water and distilled in the presence of chloroform. The organic phase was dried on sodium sulphate, filtered and concentrated. The green solid so obtained was recrystallized first from tetrahydrofuran and then from ethyl acetate.

In this manner, 0.024 mol of 2-(4-tosyloxybenzenesulphonyl)indene was obtained in the form of a white solid. Yield 82% M.P.: 174° C.

(c) 2-(4-Hydroxybenzenesulphonyl)indene

A suspension of 0.01 mol 2-(4-tosyloxybenzenesulphoyl) 100 ml of 2N-sodium hydroxide and 160 ml of ethanol was heated to 80° C. After complete dissolution, the reaction medium was poured into water, acidified with dilute hydrochloric acid and distilled in the presence of dichloromethane. The residue was stirred in the presence of animal charcoal and sodium sulphate and then filtered and concentrated.

In this manner 0.005 mol of 2-(4-hydroxybenzenesulphonyl)indene was obtained in a yield of 52%. M.P.: 209°–210° C. (ethyl acetate/hexane).

(d)
2-[4-{3-[N-methyl-N-(3,4-dimethoxy-β-phenethyl)amino]propyloxy}benzenesulphonyl]indene oxalate A mixture of 0.005 mol of 2-(4-hydroxybenzenesulphonyl)indene and 3.5 g of crushed potassium carbonate in 10 ml of dimethylsulphoxide was stirred for 30 min. After that, 0.006 mol of 1-chloro-3-[N-methyl-N-(3,4-dimethoxy-β-phenethyl)amino]propane oxalate was added while stirring was maintained for 24 hours at room-temperature. The medium was poured into water and extracted with ethyl ether. The ethereal solution was washed with water, dried on anhydrous sodium sulphate and filtered. The ethyl ether was eliminated with a rotatory evaporator and the residue so obtained was purified by chromatography on a silica column. The base so provided was then transformed into an oxalate by adding oxalic acid in ethyl ether.

In this manner 2-[4-{[N-methyl-N-(3,4-dimethoxy-β-phenethyl)amino]propyloxy}benzenesulphonyl]indene oxalate was obtained. M.P.: 176° C. (ethanol/isopropanol).

EXAMPLE 34

Preparation of
2-isopropyl-3-[4-{3-[N-methyl-N-(3,4-dimethoxy-benzyl)amino]propyloxy}benzenesulphonyl]benzofuran acid oxalate (SR 33747 A)

(a)
2-Isopropyl-3-[4-(3-bromopropyloxy)benzenesulphonyl]benzofuran

This compound was obtained using the method described in Example 15a.
M.P.: 111°–112° C.
Using the same procedure the following compounds were prepared:

COMPOUNDS

2-Isopropyl-3-[4-(2-bromoethoxy)benzenesulphonyl]benzofuran M.P.: 109°–110° C.

2-Isopropyl-3-[4-(4-bromobutyloxy) benzenesulphonyl]benzofuran Oily.

(b)
2-Isopropyl-3-[4-{3-[N-methyl-N-(3,4-dimethoxy-benzyl) amino) propyloxy}benzenesulphonyl]benzofuran acid oxalate A mixture of 0.0103 mol of 2-isopropyl-3-[4-(3-bromopropyloxy) benzenesulphonyl]benzofuran and 0.0206 mol of N-methyl-3,4-dimethoxyβ-phenethylamine in 75 ml of toluene was refluxed for 4 days in the presence of 0.03 mol of anhydrous and finely crushed potassium carbonate. After reacting the medium was allowed to cool, the mineral salts were filtered out and the filtrate was evaporated to dryness. After that, the unreacted amine was separated out by elution chromatography on neutral alumina using chloroform as eluent. The desired product was then purified by elution chromatography on silica with acetone as eluent. The oil so isolated (yield: about 96%) was then transformed into an acid oxalate in ethyl acetate using an ethereal solution of oxalic acid.

In this manner, 2-isopropyl-3-[4-{3-[N-methyl-N-(3,4-dimethoxy-benzyl) amino]propyloxy}benzenesulphonyl]benzofuran acid oxalate was obtained in a yield of 40 to 60%. M.P.: 167° C. (ethanol).

Using the same method as that described above the following compounds were prepared:

COMPOUNDS

2-Isopropyl-3-[4-{2-[N-methyl-N-(3,4-dimethoxy-benzyl)amino]ethyloxy)}benzenesulphonyl benzofuran hemioxalate(SR 33752 A) (Example 35) M.P.: 197° C. (methanol)

2-Isopropyl-3-[4-{3-[N-(3,4-dimethoxy-β-phenethyl)amino]propyloxy}benzenesulphonyl]benzofuran acid oxalate (SR 33753 A) (Example 36) M.P.: 196° C. (methanol)

2-Isopropyl-3-[4{2[N-methyl-N-(3,4-dimethoxy-β-phenethyl)amino]ethyloxy}benzenesulphonyl benzofuran hemioxalate (SR 33754 A) (Example 37) M.P.: 180° C. (methanol)

2-Isopropyl-3-[4-{4-[N-methyl-N-(3,4-dimethoxy-benzyl)amino]butyloxy)}benzenesulphonyl]benzofuran hemioxalate (SR 33755 A) (Example33) M.P.: 154° C. (ethanol)

2-Isopropyl-3-[4-{4-[N-methyl-N-(3,4-dimethoxy-β-phenethyl)amino]butyloxy}benzenesulphonyl]benzofuran acid oxalate (SR 33756 A) (Example 39)

2-Isopropyl-3-[4-{3-[N-methyl-N-[(2-pyridyl)-β-ethyl]amino]propyloxy)}benzenesulphonyl]benzofuran (SR 33783) (Example 40) Yellow oil.

2-Isopropyl-3-[4-{3-[N-[3-(1,3-benzodioxolyl )]-β-ethyl]amino]propyloxy)}benzenesulphonyl benzofuran acid oxalate (SR 33790 A) (Example 47) M.P.: 194° C. (methanol)

EXAMPLE 42

Preparation of 1-isopropyl-2-[4-{3-[N-methyl-N-(3,4-dimethoxy-β-phenethyl) amino]propyloxy}benzenesulphonyl]imidazole dihydrochloride (SR 33800 A)

(a) 1-Isopropyl-2-(4-methoxybenzenesulphonyl) imidazole

Into 20 ml of acetonitrile was introduced 0.1 mol of 1-isopropylimidazole.

After that 0.1 mol of 4-methoxybenzenesulphonyl chloride in 20 ml of acetonitrile was added drop-by-drop. The addition took one hour and the temperature increased to 35° C. After one hour stirring at room-temperature 0.11 mol of triethylamine was added to the reaction medium and stirring was maintained for 20 hours. The precipitate which formed was suction-filtered the filtrate was evaporated to dryness and the residue was dissolved in ethyl acetate. After washing with neutral water, the extract was dried and isolated to give 18.3 g of a brownish oil which was purified on a silica column. The elution with ethyl acetate provided 4.5 g of a brownish oil which solidified.

In this manner, 1-isopropyl-2-(4-methoxybenzenesulphonyl) imidazole was obtained in a yield of 16%. Purity: 99.9% (high pressure liquid chromatography) M.P.: 84°-86° C. (ethyl acetate/n-hexane ½)

Using the same procedure as that described above 1-benzyl-2-(4-methoxybenzenesulphonyl) imidazole was obtained in the form of a white beige solid. M.P.: 74.5° C. (ethyl acetate/n-hexane ½)

(b) 1-Isopropyl-2-(4-hydroxybenzenesulphonyl) imidazole

In 30 ml of anhydrous N,N-dimethylformamide were suspended, under nitrogen atmosphere, 2.4 g ($48 \times 10^{-3}$ mol) of a 50% - sodium hydride oily mixture and 1.8 ml ($24 \times 10^{-3}$ mol) of 2-mercaptoethanol in 5 ml of N,N-dimethylformamide added. Stirring was maintained for one hour at room-temperature and 3.85 g ($11.7 \times 10^{-3}$ mol) of 1-isopropyl-2-(4-methoxybenzenesulphonyl) imidazole in 20 ml of N,N-dimethylformamide were then added. The medium was then heated to 140° C. for one hour, cooled and poured into 200 ml of iced water. The brownish precipitate which formed was eliminated by filtration and the filtrate was acidified by adding concentrated hydrochloric acid. The medium was then treated with sodium bicarbonate to neutrality and the filtrate was evaporated to dryness. The brownish residual solid was taken up in a dichloromethane/methanol 4/1 mixture and suction filtered to eliminate the insoluble matter. The filtrate when concentrated provided 4.75 g of a brownish oil.

In this manner, 2.3 g of 1-isopropyl-2-(4-hydroxybenzenesulphonyl) imidazole were obtained in the form of a slightly beige solid after purification on a silica column using ethyl acetate as eluent. Yield: 74.2%. Purity: 98.3% (high pressure liquid chromatography).

M.P.: 152°-153° C. (ethyl acetate/n-hexane 1/1)

Using the same procedure as that described above 1-benzyl-2-(4-hydroxybenzenesulphonyl) imidazole was obtained in the form of a white solid. Yield: 56.4%

M.P.: 161°-162° C. (ethyl acetate/methanol/n-hexane)

(c) 1-Isopropyl-2-[4-{3-[N-methyl-N-(3,4-dimethoxy-β-phenethyl)amino]propyloxy}benzenesulphonyl-]imidazole dihydrochloride In 23 ml of dimethylsulphoxide were stirred for about 15 hours at room-temperature, 2.3 g ($8.6 \times 10^{-3}$ mol) of 1-isopropyl-2-(4-hydroxybenzenesulphonyl) imidazole, 3.45 g ($9.5 \times 10^{-3}$ mol) of 1-chloro-3-[N-methyl-N-(3,4-dimethoxy-βphenethyl)amino]propane acid oxalate and 3 g ($21.5 \times 10^{-3}$ mol) of potassium carbonate. The medium was then heated for 5 hours at 60° C., poured into 100 ml of water and extracted with 3 fractions each of 50 ml of ethyl acetate.

The extracts were collected and washed with 3 fractions each of 30 ml of water to obtain 3.45 g of a brownish oil. This oil was then purified on a silica column using an ethyl acetate/methanol 75/25 mixture as solvent to provide 2.4 g of an oil. The dihydrochloride was then formed in methanol by adding gaseous hydrochloric acid. The methanol was evaporated off and the residue was taken up in dry ethyl ether and filtered out.

In this manner, 2.05 g of 1-isopropyl-2-[4-{3-[N-methyl-N-(3,4-dimethoxy-β-phenethyl)amino]propyloxy}benzenesulphonyl]imidazole dihydrochloride were obtained in the form of a white solid.

Yield: 41.4%.

Purity: 98.4%.

M.P.: 90° C.

Using the same procedure as that described above 1-benzyl-2-[4-{3-[N-methyl-N-(3,4-dimethoxy-β-phenethyl)amino]propyloxy}benzenesulphonyl]imidazole acid oxalate was obtained in the form of a white solid (SR 33776 A) (Example 43).

Yield: 49.21%.

M.P.: 130.5° C. (ethyl acetate/methanol)

EXAMPLE 44

Preparation of of
4-4-{3-[N-methyl-N-(3,4-dimethoxy-β-phenethyl-)amino]propyloxy}benzenesulphonyl]-1,5-diphenyl-imidazole acid oxalate (a)
4-(4-Methoxy-benzenesulphonyl)-1,5-diphenyl-imidazole While stirring at room-temperature, a solution of 2.1 g (0.01 mol) of (4-methoxy-benzene)sulphonylmethylisocyanide and 2.1 g (0.01 mol) of N-phenylbenzimidoyle chloride in 25 ml of dimethoxyethane was added drop-by drop and under nitrogen atmosphere to a suspension of 0.4 g (0.01 mol) of 60%-sodium hydride in 25 ml of dimethylsulphoxide. After the introduction, stirring was maintained for 0.75 hour and the medium was slowly poured into iced water. An amorphous product was so obtained which transformed into an oil. This oil was then purified on a neutral alumina column.

In this manner, 0.774 g of 4-(4-methoxy-benzenesulphonyl)-1,5-diphenyl-imidazole was obtained in a yield of 20%.

M.P.: 157° C.

(b)
4-(4-Hydroxy-benzenesulphonyl)-1,5-diphenyl-imidazole

To a solution of 0.287 g ($3.7 \times 10^{-3}$ mol) of 2-mercapto-ethanol in 5 ml of N,N-dimethylformamide was added, under stirring and by little fractions, 0.354 g of 60%-sodium hydride. Stirring was maintained for 0.25 hour at room-temperature and then 0.774 g of 4-(4-methoxy-benzenesulphonyl)-1,5-diphenyl-imidazole in 5 ml of N,N-dimethylformamide was added. The reactor was heated for 1 hour in an oily bath at 140° C. and the medium was allowed to cool, poured into 30 ml of iced water and acidified to pH=5 with concentrated hydrochloric acid. The precipitate which formed was suction-filtered, washed with water and dried on phosphorous pentoxide under 5 mm Hg. The solid obtained was then washed with ethyl acetate.

In this manner, 0.617 g of 4-(4-hydroxy-benzenesulphonyl)-1,5-diphenyl-imidazole was provided in a yield of 91%.

M.P.: 300° C.

(c)
4-[4-{3-[N-methyl-N-(3,4-dimethoxy-β-phenethyl-)amino]amino]propyloxy}benzenesulphonyl-1,5-diphenyl-imidzaole acid oxalate To 0.60 g ($1.6 \times 10^{-3}$ mol) of 4-(4-hydroxy-benzenesulphonyl)-1,5-diphenyl-imidazole in 17 ml of N,N-dimethylformamide was added 0.730 g ($5.28 \times 10^{-3}$ mol) of crushed anhydrous potassium carbonate. The medium was stirred for 0.5 hour at room-temperature. After that 0.578 g ($1.6 \times 10^{-3}$ mol) of 1-chloro-3-[N-methyl-N-(3,4-dimethoxy-β-phenethyl)amino] propane acid oxalate was added and the reactor was heated in an oily bath at 105° C. for 0.75 hour. After cooling, the mixture was poured into iced water and the precipitate which formed was suction-filtered. This solid which transformed into an oil was chromatographied on a silica column using methanol as an eluent. An amorphous product was so obtained (M.P.: <50° C.) which was transformed into an oxalate in an ethyl ether/ethyl acetate mixture using an ethereal solution of oxalic acid.

In this manner, 4-[4-{3-[N-methyl-N-(3,4-dimethoxy-β-phenethyl)amino]propyloxy}benezenesulphonyl-1,5-diphenyl-imidazole acid oxalate was obtained. M.P.: 162° C. (isopropanol/ethanol/methanol).

EXAMPLE 45

Preparation of
4-[4-{3-[N-methyl-N-(3,4-dimethoxy-β-phenethyl-)amino]propyloxy}benezenesulphonyl-5-phenyl-thiazole acid oxalate (SR 33791 A)

(a) 4-(4-Methoxybenzenesulphonyl)-5-phenyl-thiazole

To 6.3 g (0.03 mol) of (4-methoxybenzene) sulphonylmethylisocyanide and 3.2 g (0.015 mol) of S-(thiobenzoyl) thioglycolic acid in 210 ml of tert-butanol, were added, at 19° C. and in 5 min., 2.6 g (0.046 mol) of crushed potassium hydroxide. Stirring was then maintained for 5.5 hours at room temperature. After that, the tert-butanol was evaporated off under vacuum and a saturated solution of sodium chloride was added to the residue. The medium was extracted with a dichloromethane/diethyl ether mixture, washed, dried on anhydrous sodium sulphate and evaporated. The residue was then purified by chromatography on a silica column using dichlorethane as eluent.

In this manner 2.2 g of 4-(methoxybenzenesulphonyl)-5-phenyl-thiazole were obtained in the form of a yellow solid.

Yield: 44%

M.P.: 130° C. (methanol)

(b) 4-(4-Hydroxybenzenesulphonyl)-5-phenyl-thiazole

A mixture of 1.1 g ($3.3 \times 10^{-3}$ mol) of 4-(4-methoxybenzenesulphonyl)5-phenyl-thiazole in a mixture of 33 ml of glacial acetic acid and 33 ml of 47% - hydrobromic acid was heated under reflux for 35 hours. The medium was evaporated to dryness under vacuum and water was added to the residue followed by sodium bicarbonate. The grey precipitate which formed was suction-filtered and taken up in dichlorethane. The phenol derivative was extracted with an aqueous solution of 0.01 mol of sodium hydroxide and regenerated by acidification using acetic acid.

In this manner, 0.7 g of 4-(4-hydroxybenzenesulphonyl)-5-phenyl-thiazole was obtained in a yield of 66%.

M.P.: 195° C.

(c)
4-[4-{3-[N-methyl-N-(3,4dimethoxy-β-phenethyl-)amino]propyloxy}benzenesylphonyl]-5-phenyl-thiazole acid oxalate To a solution of 0.75 g ($2.4 \times 10^{-3}$ mol) of 4-(4-hydroxybenzenesulphonyl)-5-phenyl-thiazole in 25 ml of N,N-dimethylformamide, was added 1.1 g ($7.9 \times 10^{-3}$ mol) of crushed anhydrous potassium carbonate. The medium was stirred for 0.5 hour at room-temperature and 0.867 g ($2.4 \times 10^{-3}$ mol) of 1-chloro-3-[N-methyl-N-(3,4-dimethoxy-β-phenethyl)amino]propane acid oxalate was added. The reaction mixture was heated at 105° C. for 0.75 hour, cooled and poured into iced water. After extraction with ethyl ether, the organic layer was washed with water and dried on anhydrous sodium sulphate. After evaporation to dryness under vacuum, the oily residue was chromatographied on a silica column using ethanol as eluent. The fractions were collected and evaporated to dryness to provide an oily product which was taken up in a dry ethyl ether- /ethyl acetate mixture. The acid oxalate was then formed by adding oxalic acid in ethyl ether.

In this manner, 0.8 g of 4-[4-{3-[N-methyl-N-(3,4-dimethoxy-β-phenethyl)amino]propyloxy}benzenesulphonyl]-5-phenyl-thiazole acid oxalate was obtained after recrystallization from methanol.

M.P.: 161.8° C.

EXAMPLE 46

Preparation of 4-[4-{3-[N-methyl-N-(3,4-dimethoxy-β-phenethyl)amino]propyloxy}benzenesulphonyl]-5-isopropyl-pyrazole acid oxalate (SR 33801 A)

(a)

1-Isobutyroyl-1-(4-tosyloxy-benzenesulphonyl)-2-N,N-dimethylamino-ethene

A solution of 9.9 g (0.025 mol) of 1-(4.tosyloxy-benzenesulphonyl)-3methyl-2-butanone (M.P.: 156°–157° C.) and 7.5 g (0.0625 mol) of N,N-dimethylformamide dimethylacetal in 50 ml of toluene was heated under reflux for 18 hours. After reacting, the medium was evaporated to dryness and the residue was stirred together with 50 ml of cyclohexane for 1.5 hour. The medium was suction-filtered, washed with cyclohexane and the product so obtained was recrystallised from 23 ml of methanol.

In this manner, 5.2 g of 1-isobutyroyl-1-(4-tosyloxy-benzenesulphonyl)-2-N,N-dimethylamino-ethene were obtained in the form of crystals.

Yield: 65.5%.

Purity: 92.01% (high pressure liquid chromatography).

M.P.: 115°–116° C.

(b)

4-(4-Hydroxy-benzenesulphonyl)-5-isopropyl-pyrazole

A solution of 4.5 g (0.01 mol) of 1-isobutyroyl-1-(4-tosyloxy-benzenesulphonyl)-2-N,N-dimethylamino-ethene and 16 ml (0.2 mol) of hydrazine hydrate in 25 ml of methanol and 7 ml of water was heated under reflux for 1 hour. After reacting, the medium was evaporated to dryness and the residue was purified by elution chromatography on silica using ethyl acetate as eluent. The oil so obtained was then crystallized from 100 ml of water and recystallized also from water.

In this manner, 0.9 g of 4-(4-hydroxy-benzenesulphonyl)-5-isopropylpyrazole was obtained in a yield of 33.7%.

Purity: 98% (High pressure liquid chromatography).
M.P.: 177°–179° C.

(c)

4-[4-{3-[N-methyl-N-(3,4-dimethoxy-β-phenethyl)amino]propyloxy}benzenesulphonyl]-5-isopropyl-pyrazole acid oxalate A mixture of 0.01 mol of 4-(4-hydroxy-benzenesulphonyl)-5-isoproyl pyrazole, 0.01 mol of 1-chloro-3-[N-methyl-N-(3,4-dimethoxy-β-phenethyl)amino]propane in 40 ml of dimethylsulphoxide and 0.028 mol of anhydrous and finely crushed potassium carbonate was stirred for 3 days at room-temperature.

After reacting, the medium was poured into a mixture of 100 ml of water and 100 g of ice. After extraction with 3 fractions each of 100 ml of isopropyl ether the organic layer was washed with 50 ml of water. The oily residue was then purified by elution chromatography on silica neutralized with diethylamine and using acetone as eluent. The acid oxalate was then formed in isopropyl ether using an ethereal solution of oxalic acid.

In this manner, 4-[4-{3-[N-methyl-N-(3,4-dimethoxy-β-phenethyl)amino]propyloxy}benzenesulphonyl]-5-isopropyl-pyrazole acid oxalate was obtained.

EXAMPLE 47

Preparation of 4-[4-{3-[N-methyl-N-(3,4-dimethoxyβ-phenethyl)amino]propyloxy}benzenesulphonyl]-5-isopropyl-isoxazole (a)

1-Isobutyroyl-1-(4-methoxy-benzenesulphonyl)-2-N,N-dimethylamino-ethene

This compound was obtained from 1-(4-methoxy-benzenesulphonyl)-3-methyl-2-butanone (M.P.: 48°–49.5° C.) using the same procedure as that described in Example 35.

Yield: 80.9%.

M.P.:
(1) 63°–66° C.
(2) 66°–71° C.

(b)

5-Isopropyl-4-(4-methoxy-benzenesulphonyl)-isoxazole

A mixture of 12.45 g (0.04 mol) of 1-(4-methoxy-benzenesulphonyl)-2-N,N-dimethylamino-ethene, 3.32 g (0.04 mol) of anhydrous sodium acetate and 2.8 g (0.04 mol) of hydroxylamine hydrochloride in 160 ml of methanol and 80 ml of water was stirred for 22 hours at room-temperature. After reacting, the medium was poured into 200 ml of water and the mixture was stirred for 0.5 hour at 10° C. The product so obtained was suction-filtered, washed with water and dried under vacuum at room-temperature.

In this manner 7.1 g of 5-isopropyl-4-(4-methoxy-benzenesulphonyl)isoxazole were obtained in a yield of 63%.

M.P.: 62°–63.5° C.

(c)

5-Isopropyl-4-(4-hydroxy-benzenesulphonyl)-isoxazole

A mixture of 16.7 g (0.06 mol) of 5-isopropyl-4-(4-methoxy-benzene-sulphonyl)-isoxazole and 32 g (0.24 mol) of aluminium chloride in 400 ml or dichlorethane was heated under reflux for 6 hours. After reaction the medium was allowed to cool and then poured into 510 g of ice and 500 ml of water. The mixture was stirred for 0.5hours decanted, washed to neutrality and evaporate under vacuum. The residue was dissolved in 400 ml of ethanol, discoloured with 6 g of active charcoal, filtered and evaporated. The product so provided was purified by elution chromatography on silica using isopropyl ether as eluent.

In this manner, 8.6 g of 5-isopropyl-4-(4-hydroxy-benzenesulphonyl)isoxazole were obtained after recrystallisation from 55 ml of toluene.

Yield: 53.6%.
M.P.: 12°–131° C.

(d)

4-[4-{3-[N-methyl-N-(3,4-dimethoxy-β-phenethyl)amino]propyloxy}benzenesulphonyl]-5-isopropyl-isoxazole This compound was obtained using the same method as that described in Example 46. M.P. of the acid oxalate: 158.3° C. (methanol).

EXAMPLE 48

Preparation of
4-[4-{3-[N-methyl-N-(3,4-dimethoxy-β-phenethyl-)amino]propyl}benzenesulphonyl]-5-isopropyl-3-phenyl-isoxazole (a)
5-Isopropyl-3-phenyl-4-(4-tosyloxy-benzenesulphonyl)-isoxazole To a solution of 0.23 g (0.01 at.gr) of sodium in 15 ml of methanol, were added, by small fractions, 3.95 g (0.01 mol) of 1-(4-tosyloxy-benzenesulphonyl)-3-methyl-2-butanone while maintaining the temperature at 10 C. At the same temperature, 1.55 g (0.01 mol) of benzhydroxamic acid chloride in 15 ml of methanol was added drop-by-drop in 20 minutes. The mixture was still stirred for 1 hour at 10° C. and the temperature was then allowed to increase to 20° C. while stirring for 4 hours. The medium was evaporated to dryness and the residue was suction filtered and washed with water. The crude product so obtained was recrystallised from about 180 ml of ethanol and then purified by elution chromatography on silica using chloroform as eluent.

In this manner, 2.65 g of 5-isopropyl-3-phenyl-4-(4-tosyloxy-benzenesulphonyl)-isoxazole were obtained in a yield of 53.2%.
Purity: 38.4% (high pressure liquid chromatography)
M.P.: 147.5°–149° C.

(b)
4-(4-Hydroxy-benzenesulphonyl)-5-isopropyl-3-phenyl-isoxazole

A mixture of 2.5 g (0.005 mol) of 5-isopropyl-3-phenyl-4-(4-tosyloxy-benzenesulphonyl)-isoxazole and 0.8 g (0.02 mol) of sodium hydroxide in 20 ml of isopropanol and 10 ml of water was heated under reflux for 2.5 hours. After reacting, the mixture was allowed to cool, diluted with 50 ml of water and acidified with concentrated hydrochloric acid. The product so obtained was suction-filtered and washed with water to obtain 1.4 g of the desired compound which was purified by elution chromatography on silica using chloroform as eluent.

In this manner, 1.12 g of 4-(4-hydroxy-benzenesulphonyl)-5-isopropyl-3-phenyl-isoxazole was obtained in a yield of 65.9%.
M.P.: 173°–174.5° C.

4-[4-{3-[N-methyl-N-(3,4-dimethoxy-β-phenethyl-)amino]propyloxy}benzenesulphonyl]-5-isopropyl-3-phenyl-isoxazole This compound was obtained following the method described in Example 46.

EXAMPLE 49

Preparation of
2-[4-{3-[N-methyl-N-(3,4-dimethoxy-β-phenethyl-)amino]propyloxy}benzenesulphonyl]-naphthalene acid oxalate (SR 33732A)

(a) 2-Benzenesulphonate-naphthalene

A solution of 510 ml of a 25%-aqueous solution of potassium carbonate was added to a mixture of 60 g (0.264 mol) of 2-naphthalenesulfonyl chloride and 0.264 mol of phenol in 600 ml of acetone. A precipitate formed. The medium was stirred for about 15 hours at room-temperature and then filtered. After washing first with a 1%-sodium hydroxide solution and then with water, the medium was dried and recrystallized from methanol.

In this manner, 2-benzenesulphonate-naphthalene was obtained in a yield of 84%.
M.P.: 98° C.

(b) 2-(4-Hydroxy-benzenesulphonyl)naphthalene

To 70 ml of nitrobenzene and 2 equivalents of aluminium chloride were added 20 g of 2-benzenesulphonate naphthalene. The mixture was heated to 120°–140° C. for about 2.5 hours and became black. The medium was then decomposed using a hydrochloric acid/ice mixture. After decantation, the dried organic layer was purified on a silica column using a dichloromethane/heptane 5/5 mixture. The nitrobenzene was eliminated and the product was eluted with a dichloromethane/heptane 7/3 mixture. The oily compound so obtained was triturated with ethyl ether, crystallized and filtered.

In this manner, 2-(4-hydroxy-benzenesulphonyl)-naphthalene was obtained.
M.P.: 170° C.

(c)
2-[4-{3-[N-methyl-N-(3,4-dimethoxy-β-phenethyl-)amino]propyloxy}benzenesulphonyl]-naphthalene acid oxalate A mixture of 1.4 g of 2-(4-hydroxy-benzenesulphonyl)-naphthalene 5 equivalents of potassium carbonate and 1.5 equivalent of 1-chloro-3-[N-methyl-N-( 3,4-dimethoxy-β-phenethyl)amino]propane acid oxalate in 5 ml of dimethylsulphoxide was heated on a water-bath at 30°–35° C. for 15 hours. After that, 10 ml of water were added and the medium was extracted with dichloromethane and decanted. The organic layer was dried and purified on a silica column using first dichloromethane and then a dichloromethane/methanol 98/2 mixture as eluents.

In this manner, 2-[4-{3-[N-methyl-N-(3,4-dimethoxy-β-phenethyl)amino]propyloxy}benzenesulphonyl]-naphthalene acid oxalate was obtained in a yield of 75%.
M.P.: 164° C. (ethanol)

EXAMPLE 50

Preparation of
1-[4-{3-[N-methyl-N-(3,4-dimethoxy-β-phenethyl-)amino]propyloxy}benzenesulphonyl]cyclohexene acid oxalate (SR 33767 A)

(a) 2-Iodo-1-(4-tosyloxybenzenesulphonyl) cyclohexene

This compound was obtained following the method described in Example 33 (a) but replacing sulphonyl chloride by sulphonyl iodide and heating at 40° C. for 4 hours.
Yield: 40%
M.P.: 109° C.

(b) 1-(4-Tosyloxybenzenesulphonyl) cyclohexene

This compound was obtained following the method described in Example 33 b).
Yield: 80%.
M.P.: 110° C.

(c) 1-(4-Hydroxybenzenesulphonyl) cyclohexene

This compound was obtained following the method described in Example 33 c).
M.P.: 120° C.

(d)
1-[4-{3-[N-methyl-N-(3,4-dimethoxy-β-phenethyl-
)amino]propyloxy}benzenesulphonyl]cyclohexene acid
oxalate Yield: 65%
M.P.: 174° C.

EXAMPLE 51

Preparation of
2-isopropyl-3-[4-{3-[N-methyl-N-(3,4-dimethoxy-β-
phenethyl)amino]propyloxy}benzenesulphonyl]indole
hemioxalate (SR 33738 A)

(a) 2-isopropyl-3-(4-methoxy-benzenesulphonyl) indole

A solution of 1.4 g ($5 \times 10^{-3}$ mol) of 2-isopropyl-3-(4-methoxyphenylthio) indole (prepared from 2-isopropylindole and 4-methoxythiophenol in the presence of iodine) in 25 ml of dichloromethane was stirred and cooled to about $-5°$ C. After that 2.6 g ($15 \times 10^{-3}$ mol) of 3-chloroperbenzoic acid in 25 ml of dichloromethane was added drop-by-drop. The temperature was then allowed to return to room-temperature and the stirring was maintained for 2 hours. The reaction product was washed with a diluted sodium hydroxide solution and then twice with water. The medium was dried on anhydrous sodium sulphate, filtered and the solvent was evaporated off.

In this manner, 1.3 g of 2 isopropyl-3-(4-methoxy-benzenesulphonyl) indole was obtained after recrystallization from toluene.

M.P.: 178° C.

Using the same procedure as that described above, 3-isopropyl-2-(4-methoxy-benzenesulphonyl)indole was prepared.

Yield: 90%.
M.P.: 124° C.

(b) 2-Isopropyl-3-(4-hydroxy-benzenesulphonyl)indole

To a solution of 3.3 g (0.01 mol) of 2-isopropyl-3-(4-methoxybenzenesulphonyl)indole in 20 ml of N,N-dimethylformamide was added a solution of 0.024 mol of a 50%—suspension sodium hydride and 0.012 mol of 2-mercaptoethanol in 10 ml of N,N-dimethylformamide. The medium was heated to 135° C. for 4 hours and cooled. After that a solution of 0.016 mol of sodium hydride and 0.008 mol of 2-mercapto-ethanol was again added and the mixture was again heated at 135° C. for 3 hours. The reaction medium was then taken up in 50 ml of water, acidified, extracted with ethyl ether and purified by chromatography on silica.

In this manner, 3.6 g of 2-isopropyl-3-(4-hydroxy-benzenesulphonyl) indole were obtained in oily form and the product was crystallized from an ethanol/water mixture.

Yield: 82%.
M.P.: 152° C.

Using the same procedure as that described above, 3-isopropyl-2-(4-hydroxy-benzenesulphonyl)indole was prepared.

Yield: 46.9%.
M.P.: about 72° C.

(c)
2-Isopropyl-3-[4-{3-[N-methyl-N-(3,4-dimethoxy-β-
phenethyl)amino]propyloxy}benzenesulphonyl]indole
hemioxalate This compound was obtained in accordance with Example 15.
Yield: 50%.
M.P.: about 115° C. (isopropanol/ethyl ether)

Using the same procedure as that described above the following compounds were prepared:

Compounds
2-Isopropyl-3-{4-[3-(di-n-butylamino)propyloxy]benzenesulphonyl}indole acid oxalate (SR 33743 A) (Example 52)
Yield: 79.4%.
M.P.: about 85° C. (ethylacetate/isopropanol 8/2).
2-Isopropyl-3-[4-{3-[N-methyl-N-(3,4-dimethoxy-β-phenethyl)amino]propyloxy}phenylthio]indole hemioxalate (SR 33737 A) (Example 53) [from 2-isopropyl-3-(4-hydroxy-phenylthio)indole]
M.P. 134° C. (isopropanol/ethyl ether)
3-Isopropyl-2-[4-{3-N-methyl-N-(3,4-dimethoxy-β-phenethyl)amino]propyloxy}benzenesulphonyl]indole acid oxalate (SR 33807 A) (Example 54).
Yield: 42.2%.
M.P.: about 105° C.

EXAMPLE 55

Preparation of
1-methyl-2-isopropyl-3-[4-{3-[N-methyl-N-(3,4-dimethoxy-β-phenethyl)amino]propyloxy}benzenesulphonyl]indole (SR 33741)

(a)
1-Methyl-2-isopropyl-3-(4-methoxy-benzenesulphonyl-
)indole

A solution of 6.6 g (0.02 mol) of 2-isopropyl-3-(4-methoxy-benzenesulphonyl)indole in 30 ml of hexamethylphosphotriamide was cooled to about 0° C. and 1 g (0.022 mol) of a 55%—suspension of sodium hydride was added by small fractions. After the hydrogen evolution was terminated 2.8 g (0.02 mol) of methyl iodide were introduced. The stirring was maintained at room-temperature for 12 hours and the medium was poured into water and extracted with ethyl ether. The ethereal phase was washed with water, dried on anhydrous sodium sulphate and filtered. The ether was then evaporated off.

In this manner, 5.4 g of 1-methyl-2-isopropyl-3-(4-methoxy-benzenesulphonyl)indole were obtained after recrystallisation from isopropanol/hexane 1/1.

Yield: 78.7%.
M.P.: 125° C.

Using the same procedure as that described above, 1-methyl-3-isopropyl-2-(4-methoxy-benzenesulphonyl-
)indole was prepared.
Yield: 85%
M.P.: 125° C. (hexane/isopropanol 9/1)

(b)
1-Methyl-2-isopropyl-3-(4-hydroxy-benzenesulphonyl-
)indole

This compound was obtained according to Example 51(b).
Yield: 87%
M.P.: 202° C.

Using the same procedure as that described above, 1-methyl-3-isopropyl-2-(4-hydroxy-benzenesulphonyl)indole was prepared.

Yield: 45.9%
M.P.: 185° C. (dichlorethane/ethyl acetate 9/1).

(c) 1-Methyl-2-isopropyl-3-[4-{3-[N-methyl-N-(3,4-dimethoxy-β-phenethyl)amino]propyloxy}benzenesulphonyl]indole This compound was obtained according to Example 51(c).

Yield: 75%
M.P.: 96° C. (isopropanol/diisopropylether 4/6).

Using the same procedure as that described above, the following compounds were prepared:

Compounds

1-Methyl-2-isopropyl-3-{4-[3-(di-n-butylamino)-propyloxy]benzenesulphonyl}indole acid oxalate (SR 33744 A) (Example 56)
Yield: 80%.
M.P.: about 90° C. (isopropanol).

1-Methyl-2-isopropyl-3-[4-{3-[N-methyl-N-(3,4-dimethoxy-benzyl)amino]propyloxy}benzenesulphonyl]indole acid oxalate (SR 33768 A) (Example 57)
Yield: 62%.
M.P.: about 105° C. (isopropanol)

EXAMPLE 58

Preparation of 1-methyl-2-isopropyl-3-[4-{3-tert-butylamino)-propyloxy}benzenesulphonyl]indole (SR 33770)

To a solution of 2.8 g (0.0085 mol) of 1-methyl-2-isopropyl-(4-hydroxy-benzenesulphonyl)indole in 100 ml of N,N-dimethyl formamide were added 14 g of anhydrous and crushed potassium carbonate. After that 6.8 g (0.037 mol) of 1,3-dibromopropane were added and the medium was heated at 100° C. for 0.5 hour. The mixture was poured into water, extracted with ethyl ether and the ethereal fraction was washed with water, dried on anhydrous sodium sulphate, filtered and evaporated to obtain 2.7 g of 1-methyl-3-[4-(3-bromo-propoxy)benzenesulphonyl]-2-isopropyl-indole (yield: 69%). This crude bromopropoxy derivative was dissolved in 60 ml of dimethylsulphoxide and 2.2 g (0.03 mol) of tert-butylamine were added. The medium was then stirred at room-temperature for 48 hours, poured into water and extracted with ethyl ether. The ethereal solution was then washed with water, dried on anhydrous sodium sulphate, filtered and evaporated. The crude product so obtained (2.3 g) was then purified by chromatography on a silica column (solvent:methanol).

In this manner, 1.4 g of 1-methyl-2-isopropyl-3-[4-{3-tert-butylamino)propyloxy}benzenesulphonyl]indole was obtained after recrystallization from a heptane/isopropanol 1/1 mixture.

Yield: 42.3%.
M.P.: 145° C.

Using the same procedure as that described above, 1-methyl-3-isopropyl-2-[4-{3-[N-methyl-N-(3,4-dimethoxy-β-phenethyl)amino]propyloxy}benzenesulphonyl]indole acid oxalate was prepared (SR 33805 A) (Example 59).

Yield: 60.8%.
M.P.: about 94° C. (ethyl acetate/isopropanol/diisopropyl ether).

EXAMPLE 60

Preparation of 2-isopropyl-1-[4-{3-[N-methyl-N-(3,4-dimethoxy-β-phenethyl)amino]propyloxy}benzenesulphonyl]benzene acid oxalate (SR 33718A)

(a) Sodium 2-isopropyl-benzenesulphonate

To a solution of 36.5 g (0.268 mol) of 2-isopropyl-phenol, 40 g (0.268 mol) of N,N-dimethylthiocarbamoyl chloride and 3.1 g (0.013 mol) of triethylbenzylammonium chloride in 270 ml of toluene was added, at 15° C., a solution of 27 g (0.67 mol) of sodium hydroxide in 130 ml of water. The stirring was maintained at this temperature for 2 hours. The organic fraction was then washed with water and the toluene was evaporated off. An oily residue was so obtained which was purified by distillation under vacuum (138°–140° C.; 0.5 mm Hg) to provide 34 g of 2-isopropyl O-phenyldimethylthiocarbamate. This product was then submitted to a transposition reaction by heating at 300° C. for 3 hours. The crude 2-isopropyl S-phenylthiocarbamate so obtained was then taken up in 600 ml of formic acid. To the solution so obtained and at a temperature of 15° C., were then added 225 ml of 30%-hydrogen peroxide. The stirring was maintained for about 12 hours. The formic acid was then distilled under reduced pressure, the oily residue was taken up in water and sodium hydroxide was added to pH=9. The water was eliminated and the residue was recrystallized from 200 ml of boiling water. The crystallization was rendered complete by adding sodium chloride and the precipitate so obtained was dried under vacuum at 60° C.

In this manner 24.6 g of sodium 2-isopropyl-benzenesulphonate were obtained.

Yield: 70.7%

Using the same procedure as that described above sodium 2-ethylbenzenesulphonate (yield: 100%) was prepared from 2-ethyl O-phenyldimethylthiocarbamate (B.P.: 130°–132° C.; 1 mm Hg).

(b) 2-Isopropyl-1-(4-methoxybenzenesulphonyl)-benzene

A mixture of 10 ml of methanesulphonic acid and 11 g of phosphoric anhydride was heated to about 80° C. to complete dissolution of the anhydride. After cooling to room-temperature, 9.5 g (0.0425 mol) of sodium 2-isopropylbenzenesulphonate and 4.6 g (0.0425 mol) of anisole were added. The medium was heated at 80° C. for 2 hours, cooled to room-temperature and poured onto ice. After extraction with ethyl ether, the ethereal fraction was washed with water, dried on anhydrous sodium sulphate and filtered. The ether was eliminated to obtain 9.8 g of a crude product which was purified by chromatography on a silica column (solvent:dichloroethane).

In this manner, 5.2 g of 2-isopropyl-1-(4-methoxy-benzenesulphonyl)benzene were obtained, after recrystallization from heptane/isopropanol 95/5.

Yield: 42.2%
M.P.: 100° C.

Using the same procedure as that described above, 2-ethyl-1-(4-methoxy-benzenesulphonyl)-benzene was obtained. Yield: 66.6%
M.P.: 71° C.

(c)

2-Isopropyl-1-(4-hydroxy-benzenesulphonyl)-benzene

A mixture of 4.2 g (0.0145 mol) of 2-isopropyl-1-(4-methoxy-benzenesulphonyl)-benzene and 42 g of pyridine hydrochloride was heated at 220° C. for 0.5 hour. After cooling, the medium was taken up in water and extracted with dichloroethane. The dichloroethane solution was then washed with water and dried on anhydrous sodium sulphate and filtered. The solvent was then eliminated under vacuum to obtain a product which was recrystallized from an ethyl acetate/heptane 2/8 mixture.

In this manner 3.2 g of 2-isopropyl-1-(4-hydroxy-benzenesulphonyl)benzene were obtained in a yield of 80%.

M.P.: 160° C.

Using the same procedure, 2-ethyl-1-(4-hydroxy-benzenesulphonyl)benzene was prepared in a yield of 83%

M.P.: 158° C. (heptane/isopropanol 95/5).

(d)

2-Isopropyl-1-[4-{3-[N-methyl-N-(3,4-dimethoxy-β-phenethyl)amino]propyloxy}benzenesulphonyl]benzene acid oxalate This compound was obtained following the same procedure as that described in Example 9b.

Yield: 79%

M.P.: 120° C.

Using the same procedure as that described above, the compounds hereunder were prepared:

2-Isopropyl-1-{4-[3-(di-n-butylamino)propyloxy]benzenesulphonyl}benzene acid oxalate (SR 33722A) (Example 57)

Yield: 88.8%

M.P.: 88° C. (ethyl acetate)

2-Ethyl-1-[4-{3-[N-methyl-N-(3,4-dimethoxy-β-phenethyl)amino]propyloxy}benzenesulphonyl]benzene acid oxalate (SR 33735A)(Example62)

Yield: 77.8%

M.P.: 175° C. (isopropanol)

2-Ethyl-1-{4-[3-(di-n-butylamino)propyloxy]benzenesulphonyl}benzene acid oxalate (SR 33740A) (Example 63)

Yield: 72.4%

M.P.: about 80° C. (isopropanol/ethyl ether).

EXAMPLE 64

Preparation of 2-isopropyl-1-[4-{3-(tert-butylamino)propyloxy}benzenesulphonyl]benzene acid oxalate (SR 33728A)

(a)

2-Isopropyl-1-[4-(3-bromo-propyloxy)benzenesulphonyl]benzene.

While stirring 11.6 g of anhydrous and crushed potassium carbonate was added to 2 g (0.0072 mol) of 2-isopropyl-1-(4-hydroxy-benzenesulphonyl) benzene in 100 ml of N,N-dimethylformamide. After that, 5.8 g (0.0288 mol) of 1,3-dibromopropane were added and the whole was heated at 100° C. for 0.5 hour. The medium was cooled, poured into water and extracted with ethyl ether. The ethereal layer was washed with water, dried on anhydrous sodium sulphate and filtered. The ether was then eliminated and the residue was purified by chromatography on a silica column using a dichloroethane/hexane 6/4 mixture.

In this manner, 2.4 g of 2-isopropyl-1-[4-(3-bromo-propyloxy)benzenesulphonyl]benzene were obtained in oily form.

Yield: 84%

$n_D^{25}$: 1.558

Using the same procedure as that described above, 2-ethyl-1-[4-(3-bromo-propyloxy)benzenesulphonyl]benzene was obtained in a quantitative yield.

(b)

2-Isopropyl-1-[4-{3-(tert-butylamino)propyloxy}benzenesulphonyl]benzene acid oxalate A mixture of 2.5 g (0.00629 mol) 2-isopropyl-1-[4-(3-bromo-propyloxy) benzenesulphonyl]benzene, 2.26 g (0.031 mol) of tert-butylamine and 25 ml of dimethyl-sulphoxide was stirred at room-temperature for 48 hours. The medium was then poured into water and extracted with ethyl ether. The ethereal fraction was washed with water, dried on anhydrous sodium sulphate and filtered. The ether was eliminated to obtain 2.4 g of a base of which the acid oxalate was formed in ether medium.

In this manner, 1.8 g of 2-isopropyl-1-[4{3-(tert-butylamino)propyloxy}benzenesulphonyl]benzene acid oxalate was obtained after recrystallization from ethyl acetate/isopropanol 7/3

Yield: 60%

M.P.: 116° C.

Using the same procedure 2-ethyl-1-[4-{3-(tert-butylamino)propyloxy}benzenesulphonyl]benzene acid oxalate was prepared (SR 33763A) (Example 65)

Yield: 43.1%

M.P.: 203.7° C. (isopropanol)

EXAMPLE 66

Preparation of 5-(2-chloro-benzyl)-2-ethyl-3-[4-{3-[N-methyl-N-(3,4-dimethoxy-β-phenethyl)amino]propyloxy}benzenesulphonyl]-4,5,6,7-tetrahydrothieno[3,2-c]pyridine oxalate (SR 33785A)

(a)

5-(2-Chloro-benzyl)-2-ethyl-3-(4-hydroxy-benzenesulphonyl)-4,5,6,7-tetrahydro-thieno[3,2-c]pyridine A mixture of 13.5 g (0.046 mol) of 5-(2-chloro-benzyl)-2-ethyl-4,5,6,7-tetrahydro-thieno[3,2-c]pyridine and 29.4 g (0.047 mol) of sodium benzyloxybenzenesulphonate was heated at 60° C. for 16 hours together with a solution of 20 g of phosphorous pentoxide in 200 ml of anhydrous methanesulphonic acid. The medium was cooled and water was added. After that the mixture was neutralized by adding sodium hydroxide to pH=7. After extraction with dichloroethane, the dichloroethane fraction was washed with water, dried on anhydrous sodium sulphate and filtered. The dichloroethane was distilled off and the oily residue (25 g) was dissolved in 300 ml of ethanol. After that, 20 ml of 30%-sodium hydroxide were added and the medium was heated at 80° C. for 4 hours. The ethanol was eliminated and the residue was taken up in water. The medium was treated with active charcoal, filtered and neutralized with acetic acid. After filtration, the product was washed on the filter with water and dried under vacuum at 60° C. to obtain 12.5 g of a product which was purified on a silica column using dichloroethane/ethyl acetate 8/2 as eluent.

In this manner, 9.1 g of 5-(2-chloro-benzyl)-2-ethyl-3-(4-hydroxybenzenesulphonyl)-4,5,6,7-tetrahydro-thieno[3,2-c]pyridine were obtained.
Yield: 45.3%
M.P.: 176° C. (hexane/isopropanol 7/3)

(b)
5-(2-chloro-benzyl)-2-ethyl-3-[4-{3-[N-methyl-N-(3,4-dimethoxy-β-phenethyl)amino]propyloxy}benzenesulphonyl]-4,5,6,7-tetrahydro-thieno[3,2-c]pyridine oxalate A mixture of 0.0031 mol of 5-(2-chloro-benzyl)-2-ethyl-3-(4-hydroxybenzenesulphonyl)-4,5,6,7-tetrahydro-thieno[3,2-c]pyridine and 2 g of anhydrous and crushed potassium carbonate was stirred for 0.5 hour in 20 ml of N,N-dimethylformamide. After that, 0.0031 mol of 1-chloro-3-[N-methyl-N-(3,4-dimethoxy-β-phenethyl)amino]propane was added. The medium was heated at 100° C. for 0.5 hour, cooled, poured into water and extracted with ethyl ether. The ethereal fraction was washed with water, dried on anhydrous sodium sulphate and filtered. The ether was then eliminated and the oil so obtained was purified by chromatography on a silica column using ethanol as solvent to provide 1.3 g of a base (61.9%). The oxalate was then formed in dry ethylether and recrystallized from an ethyl acetate/isopropanol/diisopropyl ether.

In this manner, 5-(2-chloro-benzyl)-2-ethyl-3-[4-{3-[N-methyl-N-(3,4-dimethoxy-β-phenethyl)amino]propyloxy}benzenesulphonyl]-4,5,6,7-tetrahydro-thieno[3,2-c]pyridine was obtained.
M.P.: 110° C.

Using the same procedure as that described above 5-(2-chloro-benzyl)-2-ethyl-3-{4-[3-(di-n-butylamino)propyloxy]benzenesulphonyl}-4,5,6,7-tetrahydro-thieno[3,2-c]pyridine dioxalate (SR 33787A) (Example 67) was obtained.
M.P.: 105° C. (isopropanol/diisopropylether).

EXAMPLE 68

Preparation of
2-isopropyl-3-{4-[3-tert-butylamino)propyloxy]benzenesulphonyl}indolizine hydrochloride (SR 33712A)

This compound was obtained according to the procedure of Example 1.
Yield: 54.3%
M.P.: 198°-200° C. (ethyl acetate/methanol)

Using the same procedure, 2-ethyl-3-{4-[3-(di-n-butylamino)propyloxy]benzenesulphonyl}indolizine acid oxalate (SR 33711A) (Example 69) was obtained.
Yield: 75.5%
M.P.: 71°-73° C. (ethyl acetate)

EXAMPLE 70

Preparation of
4-{4-[3-(di-n-butylamino)propyloxy]benzenesulphonyl}-5-phenyl-thiazole acid oxalate (SR 33786A)

This compound was obtained according to the procedure of Example 45
Yield: 73%
M.P.: 110.4° C. (ethyl acetate)

EXAMPLE 71

Preparation of
4-{4-[3-(di-n-butylamino)propyloxy]benzenesulphonyl}-5-isopropyl-pyrazole acid oxalate (SR 33789A)

This compound was obtained according to the procedure of Example 46.
M.P.: about 53° C. (methanol)

EXAMPLE 72

Preparation of
4-{4-[3-(di-n-butylamino)propyloxy]benzenesulphonyl}-5-isopropyl-3-phenyl-isoxazole (SR 33758)

This compound was obtained according to the procedure of Example 48.
M.P.: 53.5° C. (toluene)

EXAMPLE 73

Preparation of
2-{4-[3-(di-n-butylamino)propyloxy]benzenesulphonyl}-naphthalene acid oxalate (SR 33727A)

This compound was obtained according to the procedure of Example 49.
Yield: 75%
M.P.: 90° C. (heptane)

EXAMPLES 74 to 78

Using the same procedure as those described above but starting from the appropriate product, the following compounds were prepared:
N°74:
2-isopropyl-3-[4-{3-[N-(3,4-dichloro-benzyl)amino]propyloxy}benzenesulphonyl]benzofuran acid oxalate.
M.P.: 198°-199° C. (methanol).
N°75:
2-isopropyl-3-[4-{3,4-dichloro-β-phenethyl)amino]propyloxy}benzenesulphonyl]benzofuran acid oxalate. M.P.: 203°-204° C. (methanol).
N°76:
2-isopropyl-3-[4-{3-[N-[3-(1,3-benzodioxolannyl)]-β-ethyl]amino]propyloxy}benzenesulphonyl]benzene acid oxalate.
M.P.: 164° C. (absolute ethanol).
N°77:
2-isopropyl-1-[4-{3-N-methyl-N-(3,4-dimethoxy-benzyl) amino]propyloxy]benzenesulphonyl]benzene acid oxalate.
M.P.: 168° C. (absolute ethanol).
N°78:
2-isopropyl-3-[4-{3-]N-methyl-N-(3,4-dimethoxy-β-phenethyl)amino]propyloxy}benzenesulphonyl]-1-methyl-4,5-dihydro-pyrrole acid oxalate.
M.P.: 100°-102° C. (ethyl acetate/methanol).

EXAMPLE 79

According to known pharmaceutical techniques, a capsule containing the following ingredients was prepared:

| Ingredient | mg |
|---|---|
| Compound of the invention | 100.0 |
| Starches | 99.5 |
| Colloidal silica | 0.5 |
| | 200.0 |

What we claim is:
1. An aminoalkoxyphenyl compound of formula:

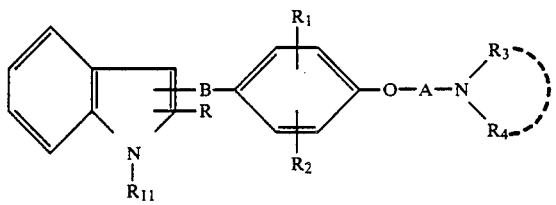

and pharmaceutically acceptable salts, in which:

B represents a —S—, —SO— or —SO$_2$— group,

R$_1$ and R$_2$, which are identical or different, each denote hydrogen, a methyl or ethyl radical or a halogen atom, A denotes a straight-or branched-alkylene radical having from 2 to 5 carbon atoms or a 2-hydroxy-propylene radical in which the hydroxy is optionally substituted by a lower alkyl radical, R$_3$ denotes an alkyl radical or a radical of formula:

—Alk—Ar in which Alk denotes a single bond or a linear-or branched-alkylene radical having from 1 to 5 carbon atoms and Ar denotes a pyridyl, phenyl, 2,3-methylenedioxyphenyl or 3,4-methylenedioxyphenyl radical or a phenyl group substituted with one or more substituents, which may be identical or different, selected from halogen atoms, lower alkyl group or lower alkoxy groups, R$_{11}$ denotes hydrogen or a lower alkyl, phenyl, diphenylmethyl, benzyl or halogenobenzyl radical, R$_4$ denotes hydrogen or a C$_{1-8}$ alkyl radical, R represents hydrogen, an alkyl radical, a cycloalkyl radical, a benzyl radical or a phenyl radical optionally substituted with one or more substituents, which may be identical or different, selected from halogen atoms and from lower alkyl, lower alkoxy or nitro groups.

2. An aminoalkoxyphenyl compound according to claim 1 in which B represents a —SO$_2$— group.

3. An aminoalkoxyphenyl compound according to claim 1 in which R$_3$ represents hydrogen and R$_4$ represents tert-butyl or R$_3$ and R$_4$ each represent n-propyl or n-butyl.

4. An aminoalkoxyphenyl compound according to claim 1 in which -O-A-NR$_3$R$_4$ represents a N-methyl-N-[(3,4-dimethoxy-β-phenethyl)amino]propyloxy group.

5. An aminoalkoxyphenyl compound according to claim 1 in which R$_1$ and R$_2$ each represent hydrogen.

6. An aminoalkoxyphenyl compound according to claim 1 in which R represents an isopropyl or cyclopropyl group.

7. An aminoalkoxyphenyl compound according to claim 1 wherein the pharmaceutically acceptable salt is the oxalate or hydrochloride.

8. An aminoalkoxyphenyl compound according to claim 1 which is 2-isopropyl-3-[4-{3-[N-methyl-N-(3,4-dimethoxy-β-phenethyl)amino]propyloxy}benzenesulfonyl]indole and its pharmaceutically acceptable salts.

9. An aminoalkoxyphenyl compound according to claim 1 which is 2-isopropyl-3-[4-{3-[N-methyl-N-(3,4-dimethoxy-β-phenethyl)amino]propyloxy}benzenesulfonyl]-1-methyl-indole and its pharmaceutically acceptable salts.

10. An aminoalkoxyphenyl compound according to claim 1 which is 3-isopropyl-2-[4-{3-[N-methyl-N-(3,4-dimethoxy-β-phenethyl)amino]propyloxy}benzenesulfonyl]indole and its pharmaceutically acceptable salts.

11. An aminoalkoxyphenyl compound according to claim 1 which is 1-methyl-2-isopropyl-3-[4-{3-[N-methyl-N-(3,4-dimethoxy-benzyl)amino]propyloxy}benzenesulfonyl]indole and its pharmaceutically acceptable salts.

12. An aminoalkoxyphenyl compound according to claim 1 which is 1-methyl-3-isopropyl-2-[4-{3-[N-methyl-N-(3,4-dimethoxy-β-phenethyl)amino]propyloxy}benzenesulfonyl]indole and its pharmaceutically acceptable salts.

13. A pharmaceutical or veterinary composition for the treatment of angina pectoris, hypertension and arrhythmia containing, as active principle, an effective amount of at least one aminoalkoxyphenyl compound according to claim 1 in combination with a pharmaceutical vehicle or a suitable excipient.

14. A method of treating angina pectoris, hypertension and arrhythmia in a host in need of such treatment comprising the administration of the host of an effective amount of an aminoalkoxyphenyl compound according to claim 1.

* * * * *